United States Patent
Garoff et al.

(10) Patent No.: US 6,207,607 B1
(45) Date of Patent: Mar. 27, 2001

(54) COMPOSITION CONTAINING MAGNESIUM, TITANIUM, HALOGEN AND AN INNER ELECTRON DONOR, ITS PREPARATION AND USE FOR THE POLYMERIZATION OF ALPHA-OLEFINS

(75) Inventors: Thomas Garoff, Helsinki; Timo Leinonen, Tolkkinen; Sirpa Ala-Huikku, Helsinki, all of (FI)

(73) Assignee: Borealis A/S, Lungby (DK)

( * ) Notice: Subject to any disclaimer, the term of this patent is extended or adjusted under 35 U.S.C. 154(b) by 0 days.

(21) Appl. No.: 09/155,437

(22) PCT Filed: Mar. 26, 1997

(86) PCT No.: PCT/FI97/00191
  § 371 Date: Dec. 23, 1998
  § 102(e) Date: Dec. 23, 1998

(87) PCT Pub. No.: WO97/36938
  PCT Pub. Date: Oct. 9, 1997

(30) Foreign Application Priority Data

Mar. 29, 1996 (FI) .......................................... 961457

(51) Int. Cl.[7] .............................. B01J 31/38; C08F 4/654; C07F 7/28
(52) U.S. Cl. ......................... 502/127; 502/125; 502/129; 502/133; 502/150; 502/107; 526/138
(58) Field of Search ................................ 502/125, 127, 502/129, 133, 150, 107; 526/138

(56) References Cited

U.S. PATENT DOCUMENTS

| | | |
|---|---|---|
| 4,439,540 | 3/1984 | Cecchin et al. . |
| 4,990,477 * | 2/1991 | Kioka et al. ........................... 502/107 |
| 5,494,872 * | 2/1996 | Hosaka et al. ........................ 502/115 |

FOREIGN PATENT DOCUMENTS

| | | |
|---|---|---|
| 0488537B1 | 6/1992 | (EP) . |
| 0 488 537 * | 6/1992 | (EP) . |
| 2049709 | 12/1980 | (GB) . |

OTHER PUBLICATIONS

Chemical Abstract, vol. 112 (1990), 236033v.
Chemical Abstract, vol. 120 (1994), 135220p.
Chemical Abstract, vol. 118 (1993), 83875a.
Chemical Abstract, vol. 112 (1990) 236033v.*

* cited by examiner

*Primary Examiner*—David W. Wu
*Assistant Examiner*—Ling-Siu Choi

(57) ABSTRACT

Disclosed is the homogenous reaction at 40–200° C. of $MgX^1_2-nR^1OH$ (where n=2.0–6.4) with $TiX^2_4$ and a higher ($C_6$–$C_{20}$) alkyl ester of a carboxylic acid, optionally in the presence of a solvent. In such a completely homogenous reaction, no carrier appears. In order to obtain a product in the liquid stage, the molar ratio between the ester and the $MgX^1_2.nR^1OH$ should be at least 0.8/j wherein j is the number of carboxyl groups in the ester. If the ester has two carboxyl groups, for instance, j is 2 and the molar ratio should be at least 0.8/2, that is, 0.4.

49 Claims, 35 Drawing Sheets

Schematic presentation of Examples 1 to 5

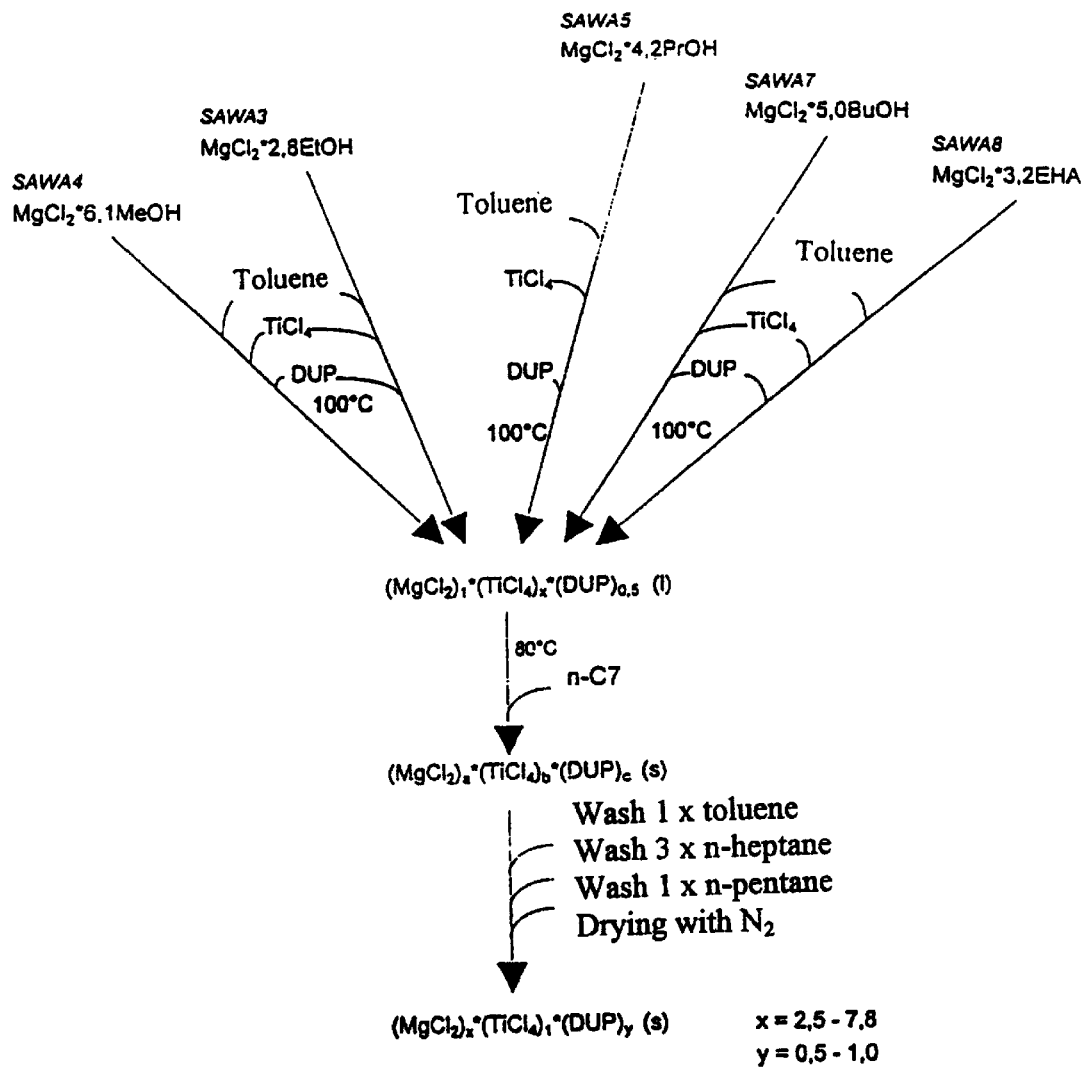
Figure 1. Schematic presentation of Examples 1 to 5

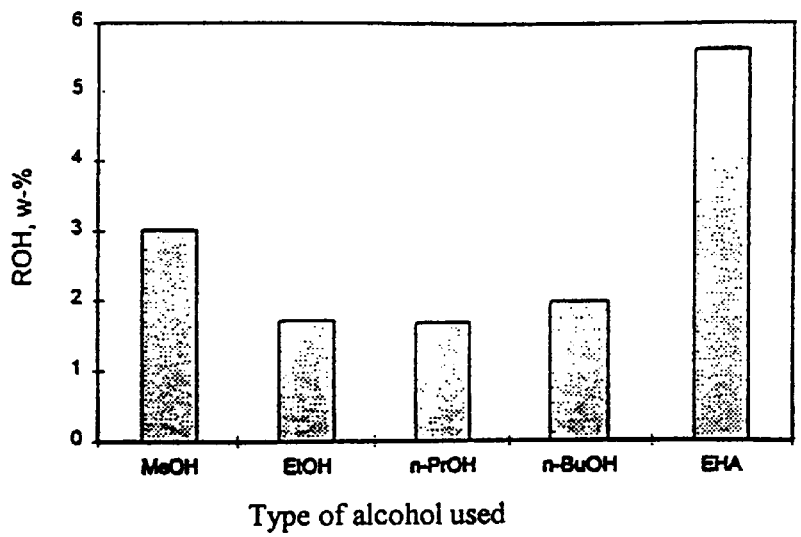
Figure 2. Alcohol concentrations of the compositions
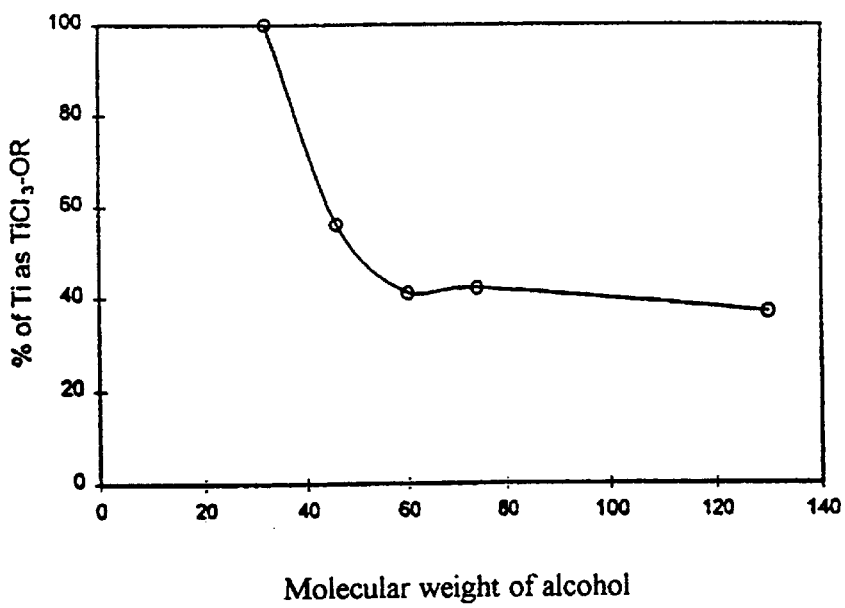
Figure 3. Proportion of Ti in the form of $TiCl_3OR$ as a function of the alcohol used in the $MgCl_2 \cdot nROH$ starting material

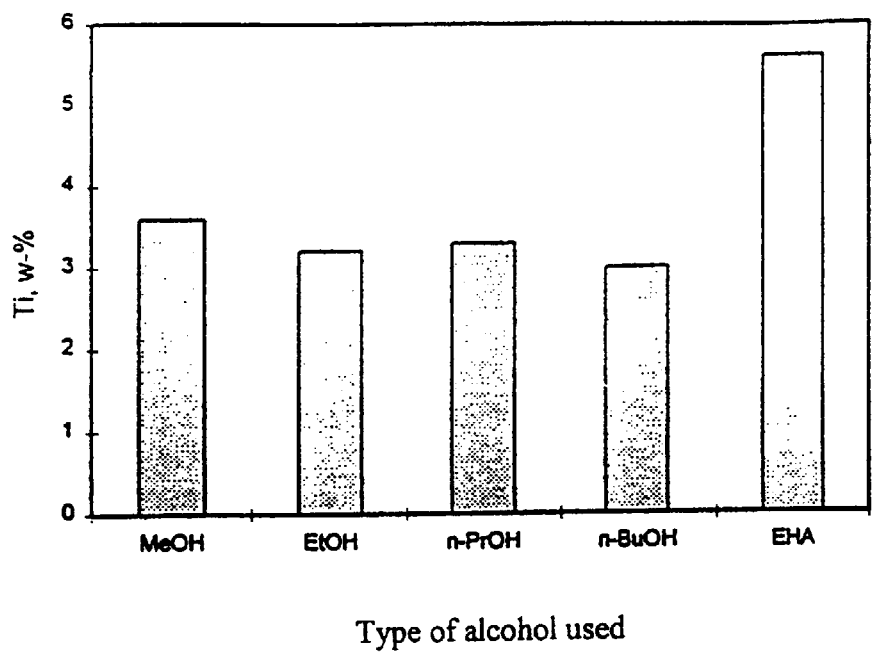
Figure 4. Titanium concentrations of the compositions
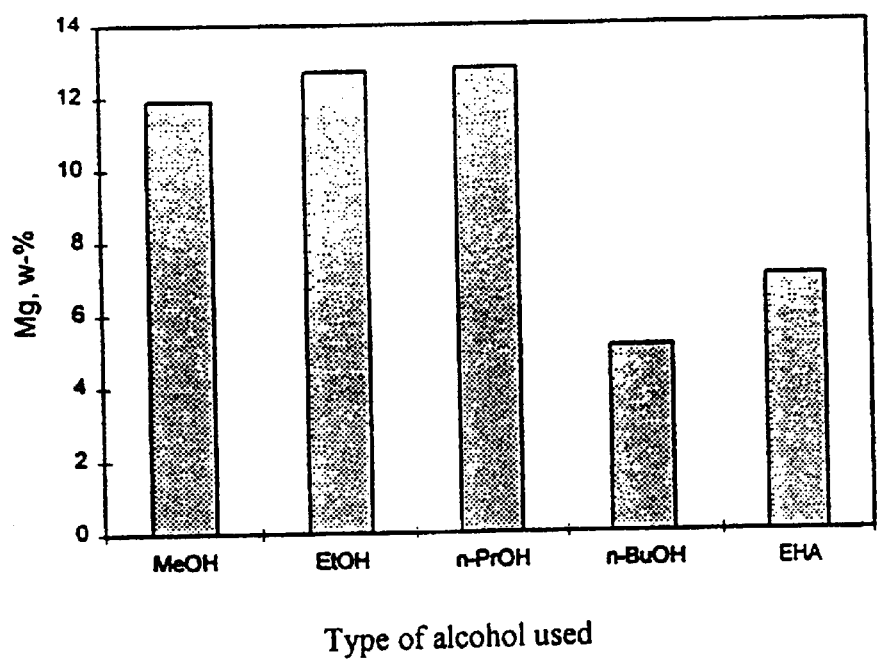
Figure 5. Mg concentrations of the compositions

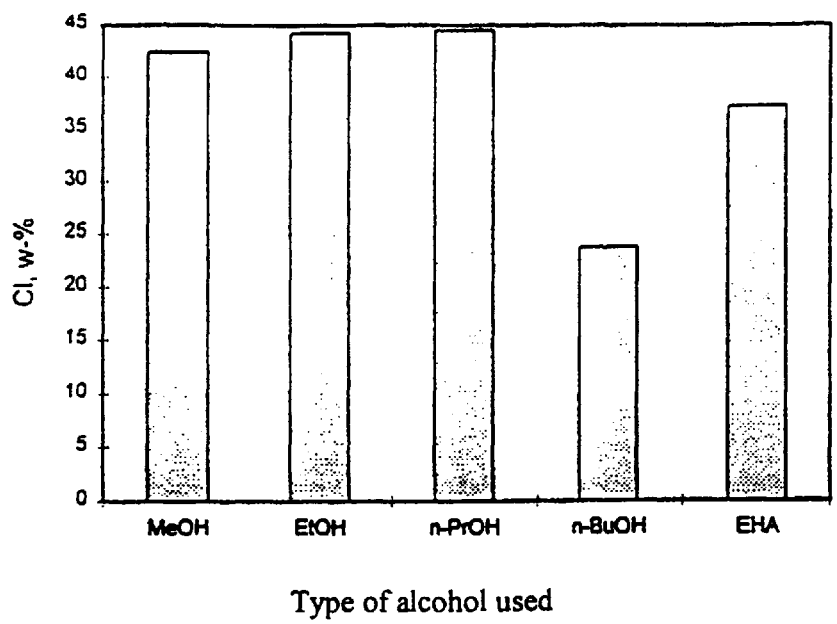
Figure 6. Cl concentrations of the compositions
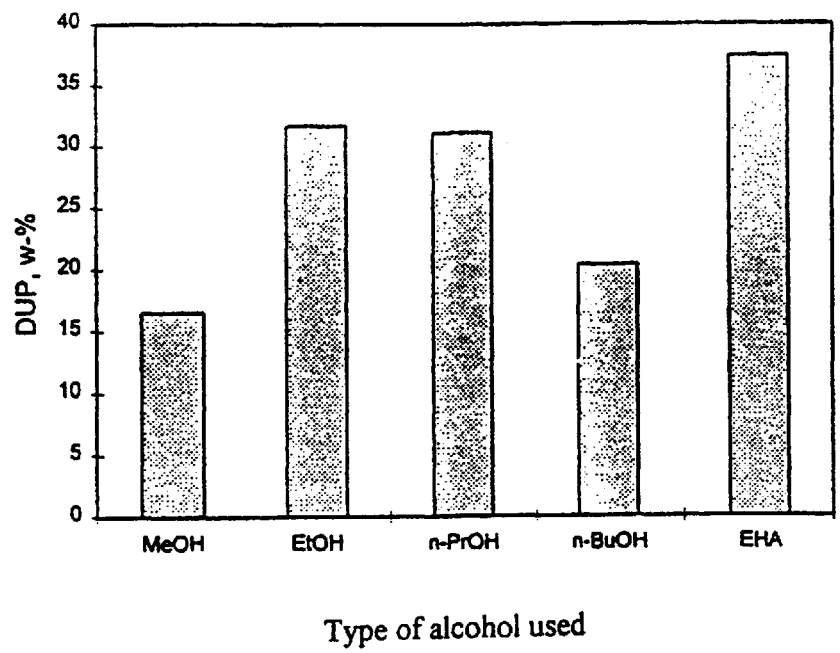
Figure 7. DUP concentrations of the compositions

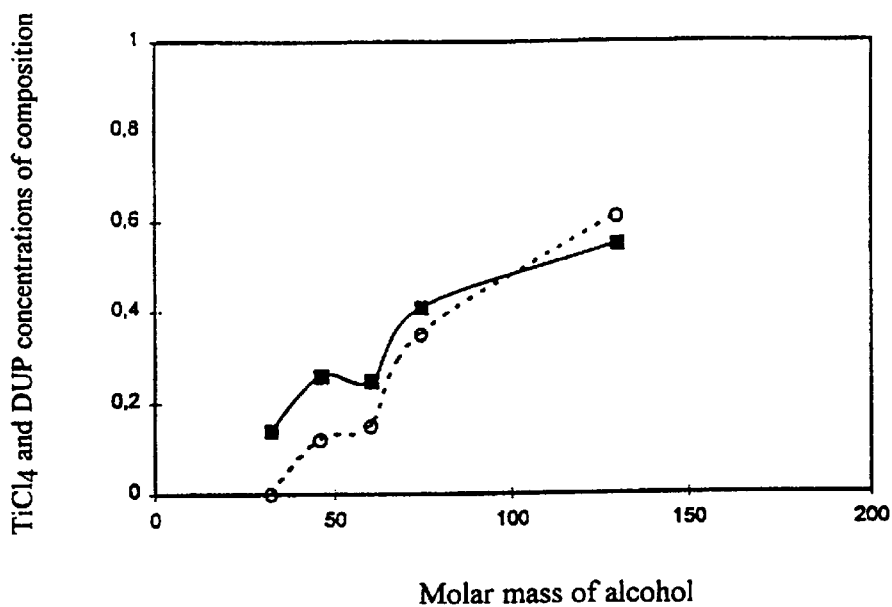
Figure 8. Comparable molar proportions of TiCl$_4$ and DUP in the (MgCl$_2$)$_v$(TiCl$_4$)$_x$(DUP)$_y$(TiCl$_3$OR)$_z$ composition as functions of the molar mass of alcohol
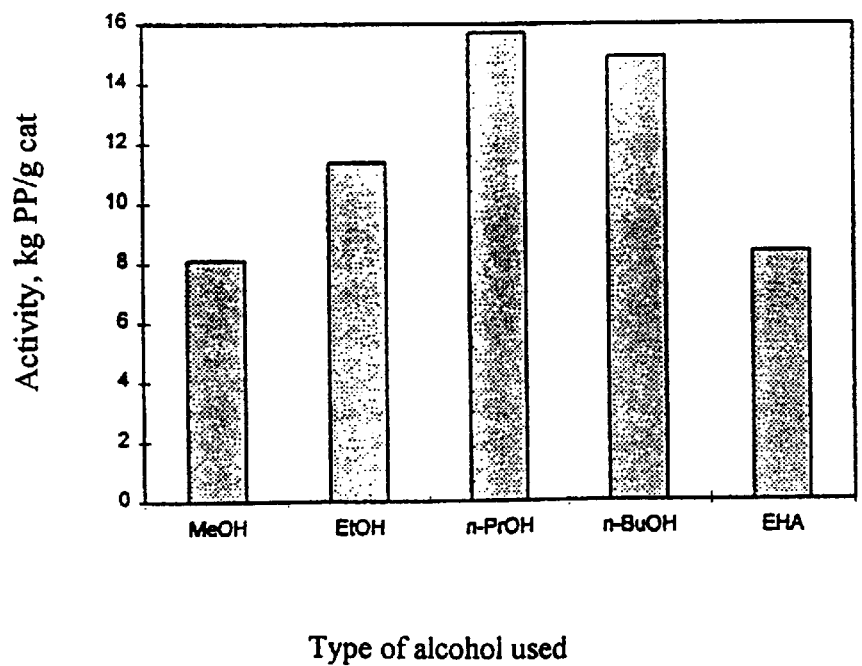
Figure 9. Activities (kg PP/g cat) of the compositions in bulk homopolymerisation

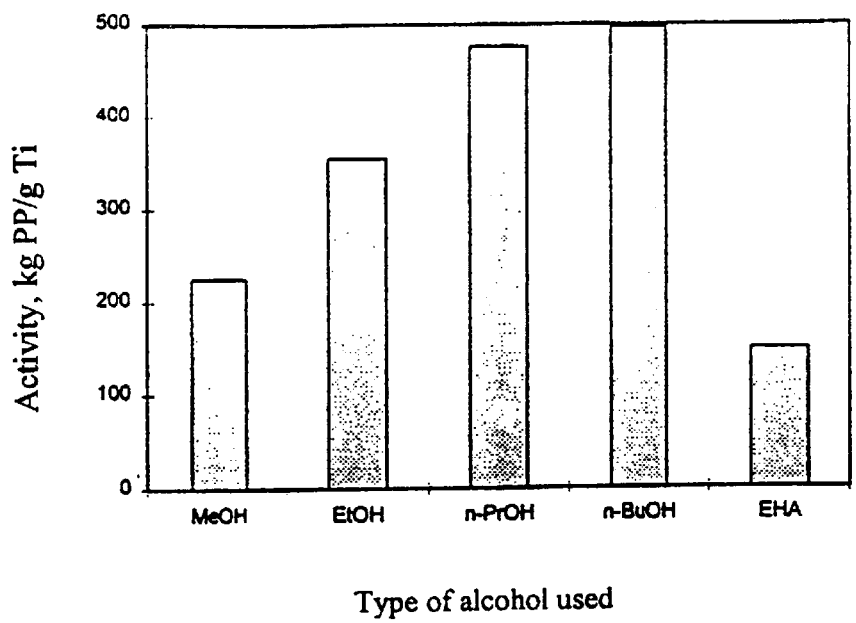
Figure 10. Activities (kg PP/g Ti) of the compositions in bulk homopolymerisation
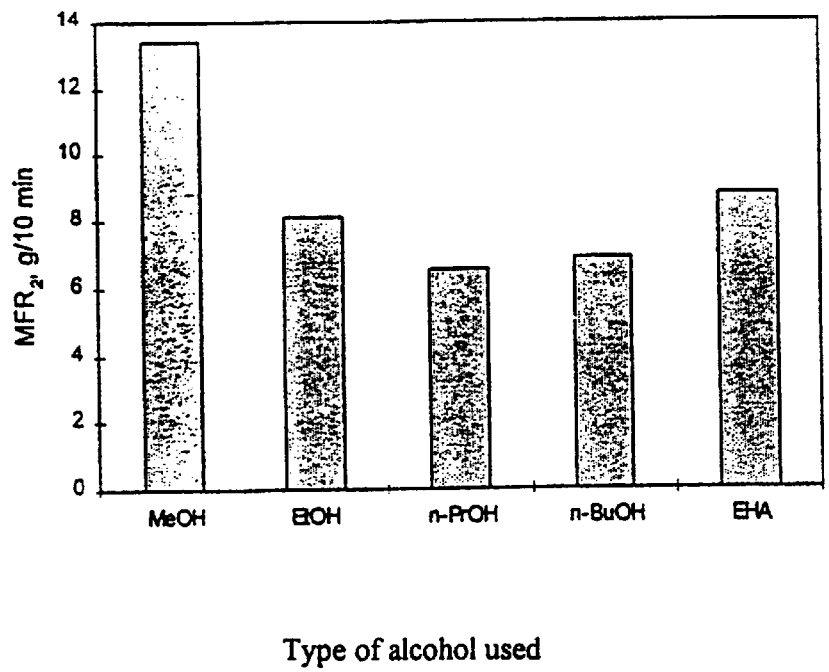
Figure 11. Melt flow rates (MFR) of bulk polypropenes

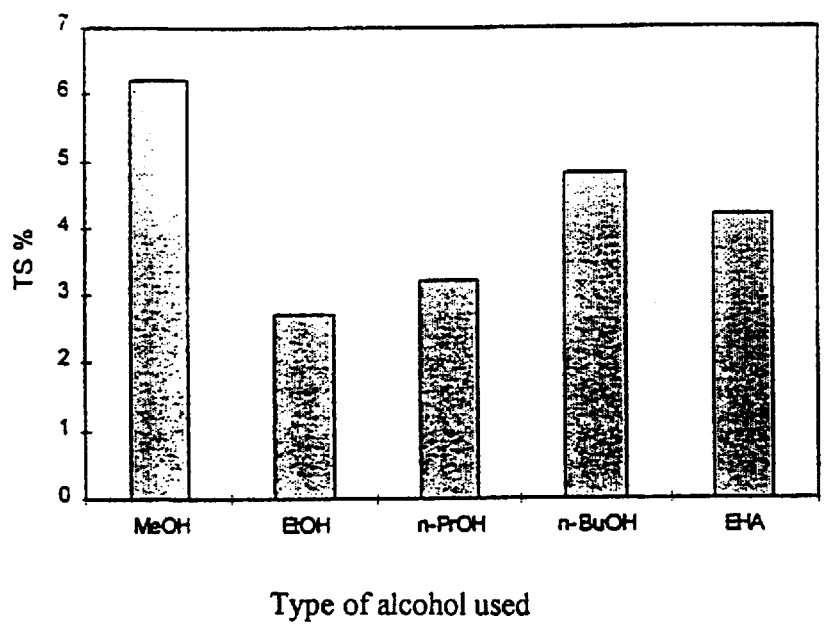
Figure 12. TS values of bulk homopolypropenes
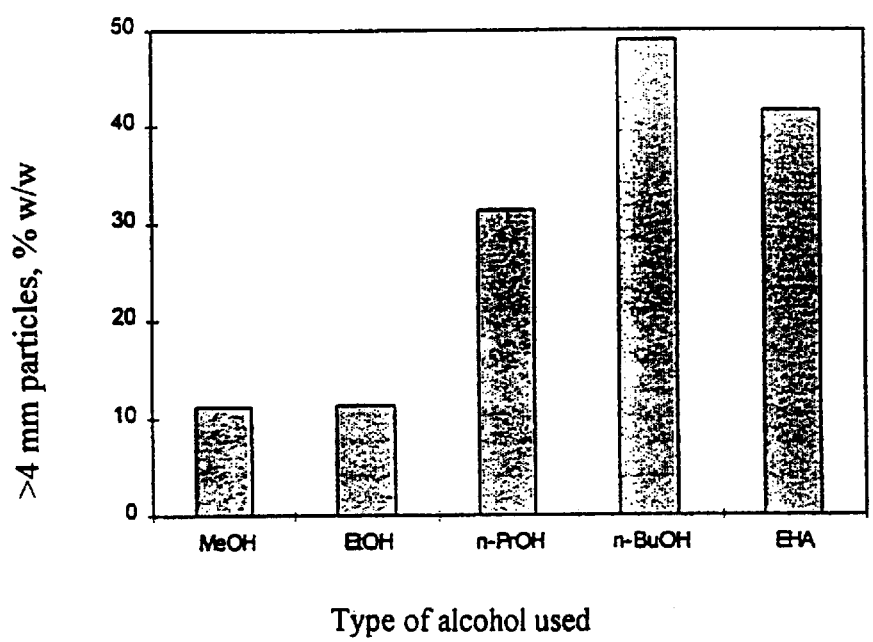
Figure 13. Proportions of >4 mm particles in bulk homopolymers

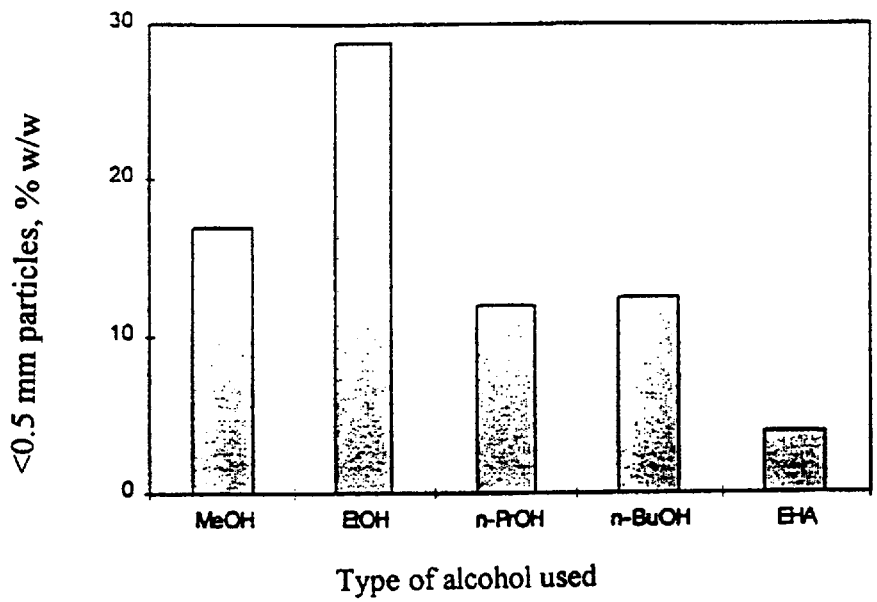
Figure 14. Proportions of <0.5 mm particles in polypropenes produced by bulk homopolymerisation
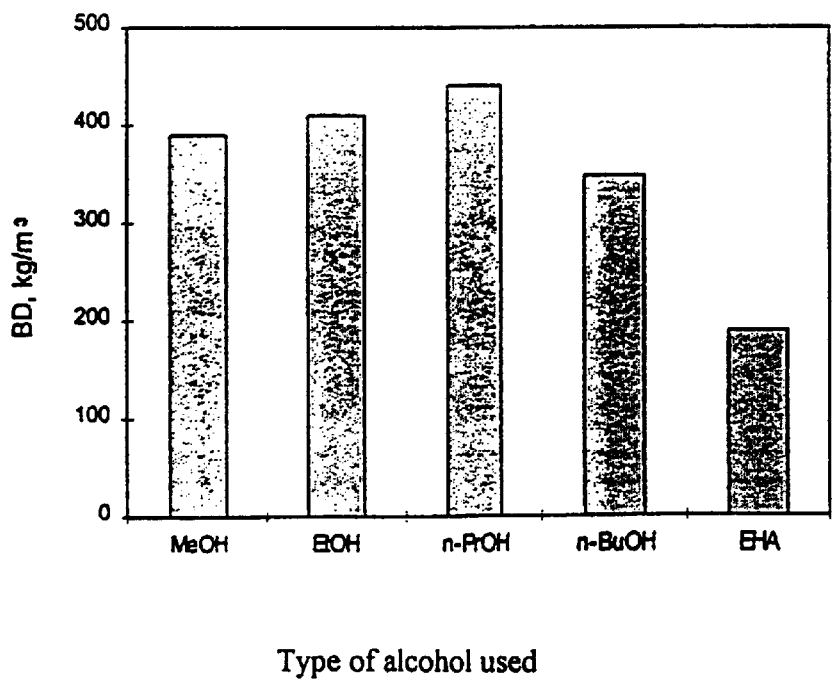
Figure 15. Bulk densities (BD) of bulk polypropenes

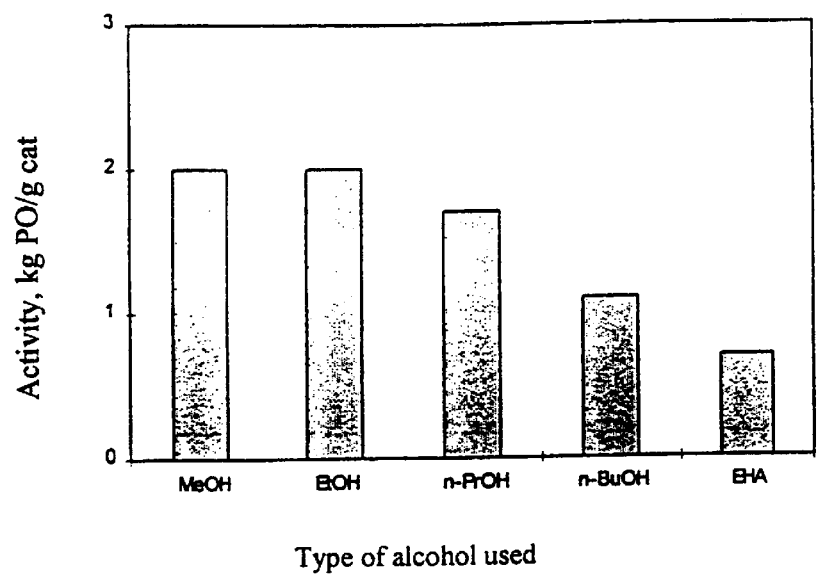
Figure 16. Activities (kg PO/g cat) of the compositions in gas-phase copolymerisation
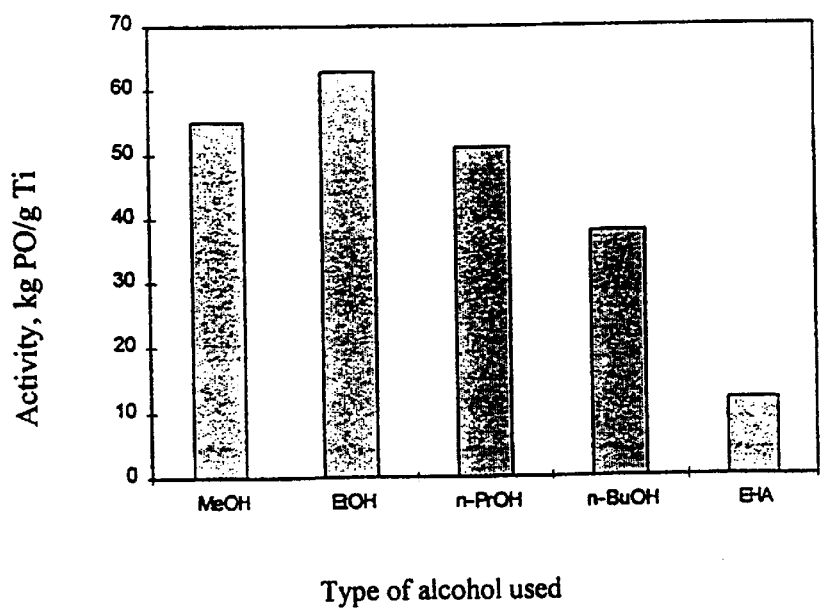
Figure 17. Activities (kg PO/g Ti) of the compositions in gas-phase copolymerisation

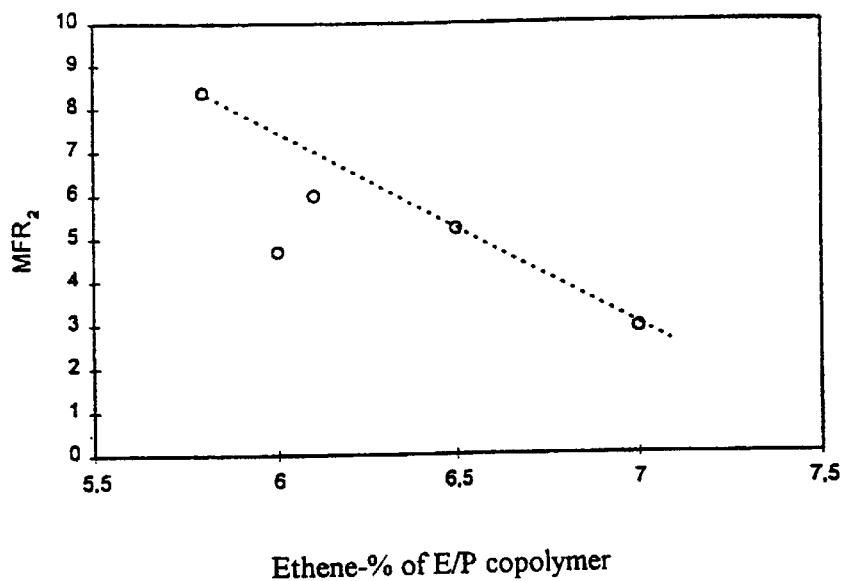
Figure 18. Correlation between MFR and ethene-% in E/P copolymers
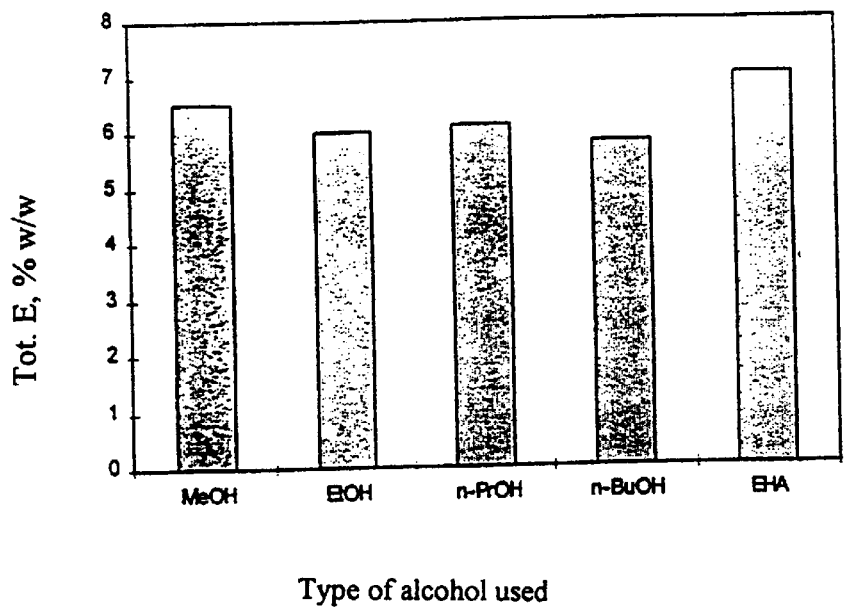
Figure 19. Total ethene concentrations in E/P gas-phase copolymers

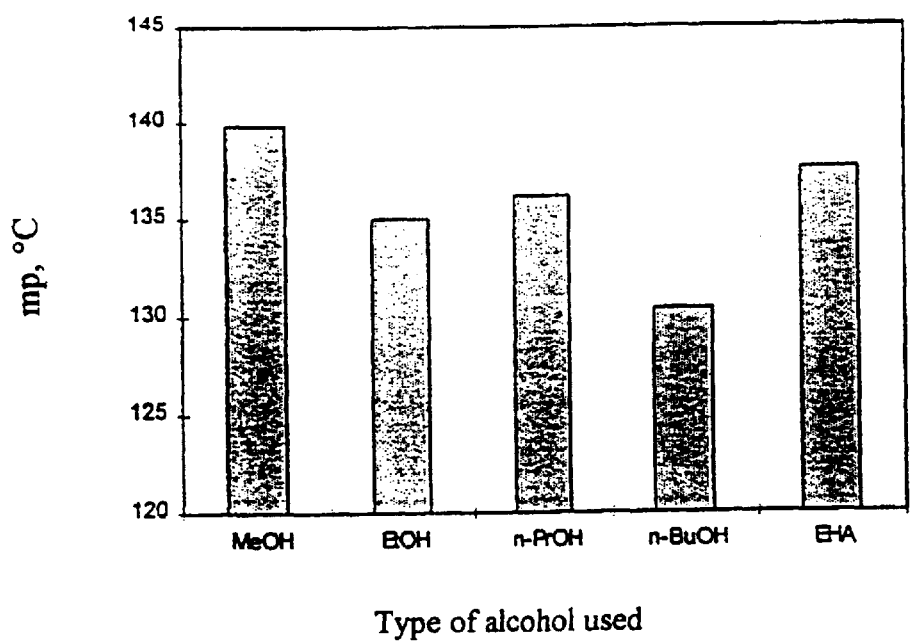
Figure 20. Melting points of gas-phase E/P copolymers
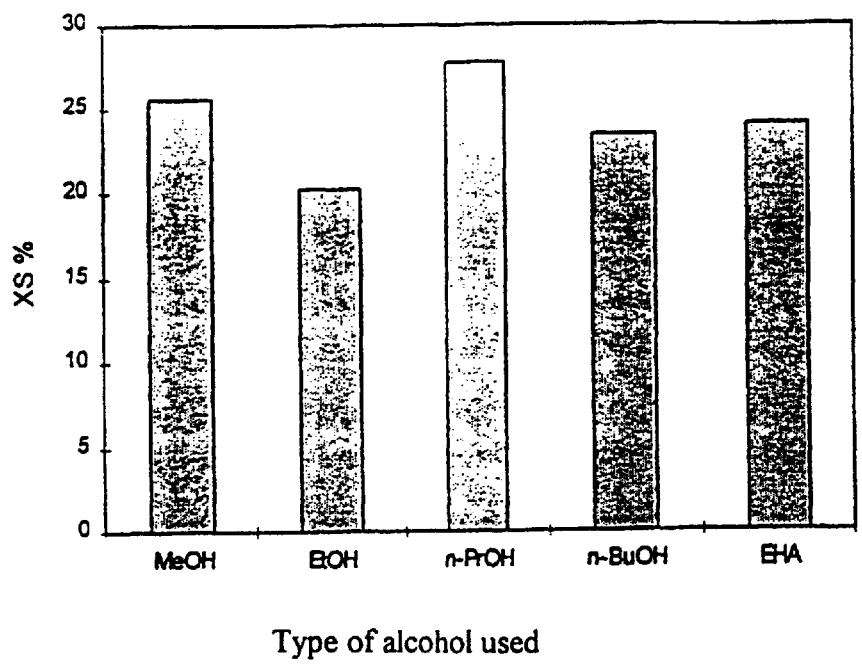
Figure 21. XS values of gas-phase E/P copolymers

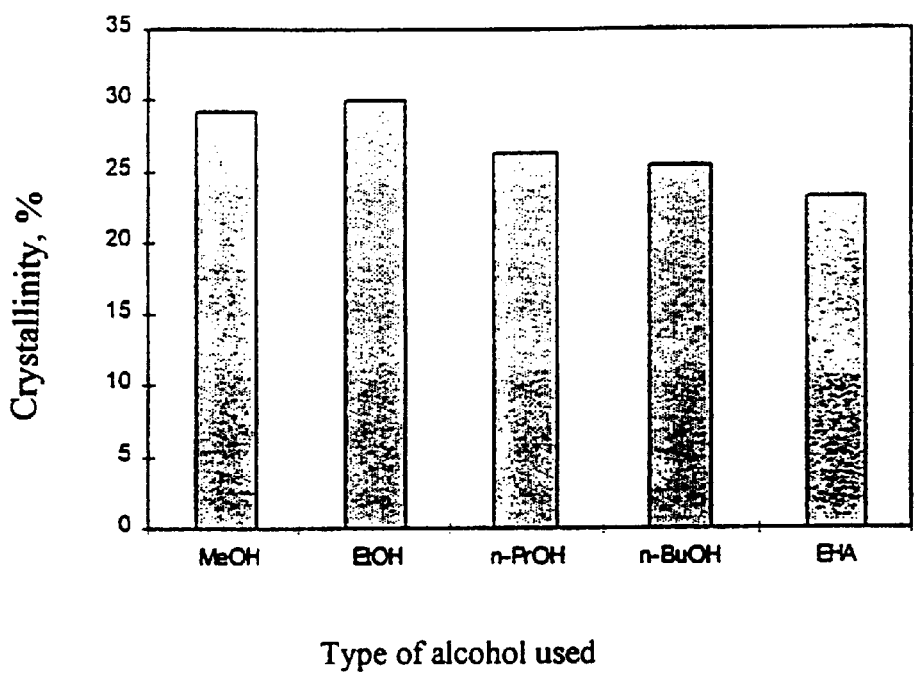
Figure 22. Crystallinities of gas-phase E/P copolymers
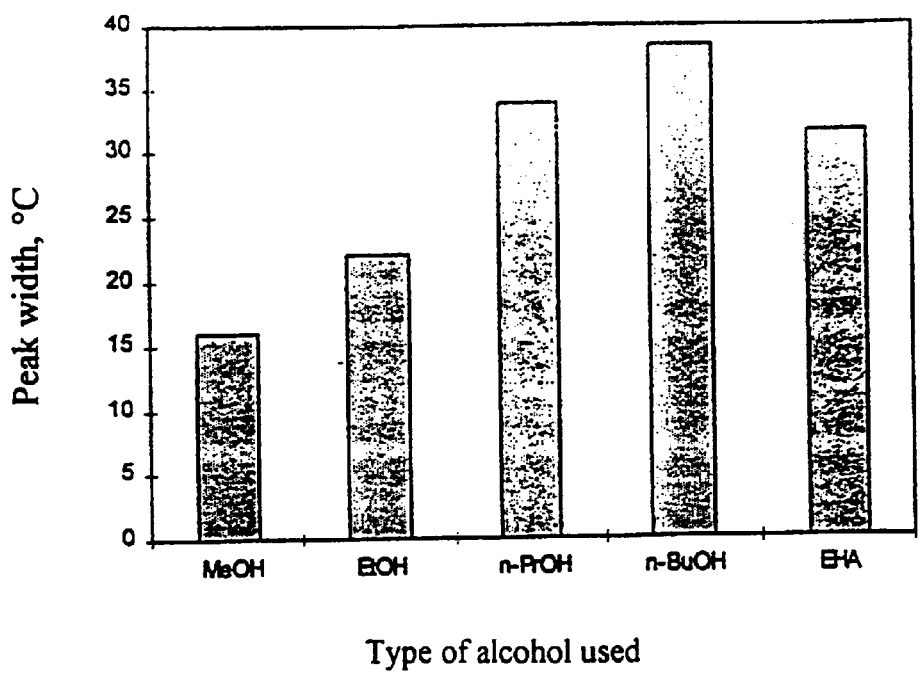
Figure 23. Widths of DSC peaks of gas-phase E/P copolymers Diagram 1.  Synthesis diagrams of Examples 6 to 9

APPENDIX 1

1. MgCl$_2$*6.1 MeOH, EK-3
Mg 8.3% w/w, MeOH 66.4% w/w

| MgCl$_2$*6.1 MeOH |
| --- |
| 5.05 g |

| Toluene |
| --- |
| 50 ml |

| TiCl$_4$ |
| --- |
| 100 ml |

| DUP |
| --- |
| 4.28 ml, DUP/Mg = 0.5 mol/mol |

Heating to 100°C
Mixing until clear solution
Cooling to 80°C

| n-Heptane |
| --- |
| 140 ml |

Precipitation, siphonation

| Wash 1 x 140 ml toluene |
| --- |

| Wash 3 x 70 ml heptane |
| --- |

| Wash 1 x 100 ml pentane |
| --- |

Drying with N$_2$ at 80°C

2. MgCl$_2$*2.8 EtOH, EK-1
Mg 10.9% w/w, EtOH 58.0% w/w

| MgCl$_2$*2.8 EtOH |
| --- |
| 8.3 g |

| Toluene |
| --- |
| 50 ml |

| TiCl$_4$ |
| --- |
| 100 ml |

| DUP |
| --- |
| 9.28 ml, DUP/Mg = 0.5 mol/mol |

Heating to 100°C
Mixing until clear solution
Cooling to 80°C

| n-Heptane |
| --- |
| 140 ml |

Precipitation, siphonation

| Wash 1 x 140 ml toluene |
| --- |

| Wash 4 x 140 ml heptane |
| --- |

| Wash 1 x 30 ml pentane |
| --- |

Drying with N$_2$ at 90°C

Figure 25a.

APPENDIX 2

3. MgCl$_2$*4.2 PrOH, EK-4
Mg 6.5% w/w, PrOH 68.0% w/w

| MgCl$_2$*4.2 PrOH |
| --- |
| 9.3 g |

| Toluene |
| --- |
| 50 ml |

| TiCl$_4$ |
| --- |
| 100 ml |

| DUP |
| --- |
| 6.2 ml, DUP/Mg = 0.5 mol/mol |

Heating to 100°C
Mixing until clear solution
Cooling to 80°C

| n-Heptane |
| --- |
| 140 ml |

Precipitation, siphonation

| Wash 1 x 140 ml toluene |
| --- |

| Wash 3 x 140 ml heptane |
| --- |

| Wash 1 x 50 ml pentane |
| --- |

Drying with N$_2$ at 80°C

4. MgCl$_2$*5.0 BuOH, EK-5
Mg 3.5% w/w, BuOH 52.9% w/w

| MgCl$_2$*5.0 BuOH |
| --- |
| 14.64 g |

| Toluene |
| --- |
| 50 ml |

| TiCl$_4$ |
| --- |
| 100 ml |

| DUP |
| --- |
| 5.26 ml, DUP/Mg = 0.5 mol/mol |

Heating to 100°C
Mixing until clear solution
Cooling to 80°C

| n-Heptane |
| --- |
| 140 ml |

Precipitation, siphonation

| Wash 1 x 140 ml toluene |
| --- |

| Wash 3 x 140 ml heptane |
| --- |

| Wash 1 x 100 ml pentane |
| --- |

Drying with N$_2$ at 80°C

Figure 25b.

APPENDIX 3

5. MgCl$_2$*3.24 EHA

| MgCl$_2$*3.07 g |
| --- |
| EHA 16.32 g |

Dissolution 4 h at 130°C
Cooling to 80°C

| Toluene |
| --- |
| 50 ml |

| TiCl$_4$ |
| --- |
| 100 ml |

| DUP |
| --- |
| 8.0 ml, DUP/Mg = 0.5 mol/mol |

Heating to 100°C
Mixing until clear solution
Cooling to 80°C

| n-Heptane |
| --- |
| 140 ml |

Precipitation, siphonation

| Wash 1 x 140 ml toluene |
| --- |

| Wash 3 x 140 ml heptane |
| --- |

| Wash 1 x 100 ml pentane |
| --- |

Drying with N$_2$ at 80°C

Figure 25c.

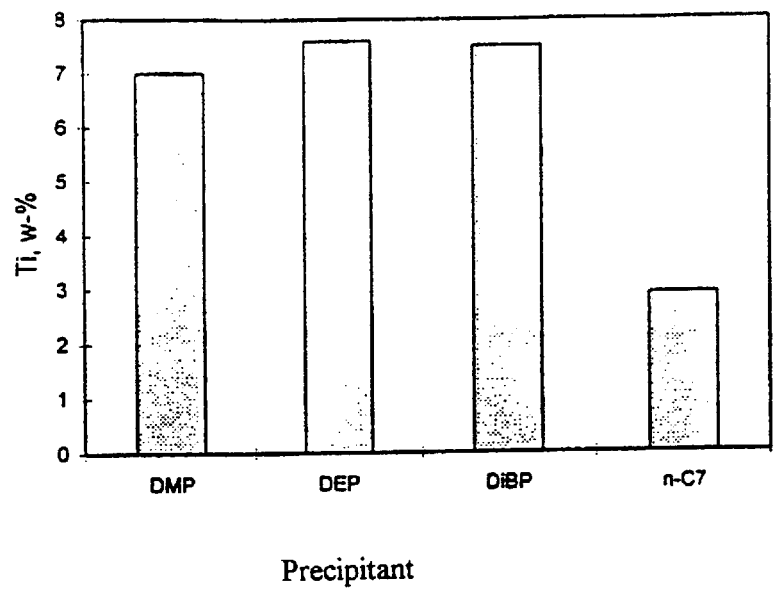
Figure 26. Titanium concentrations of the compositions
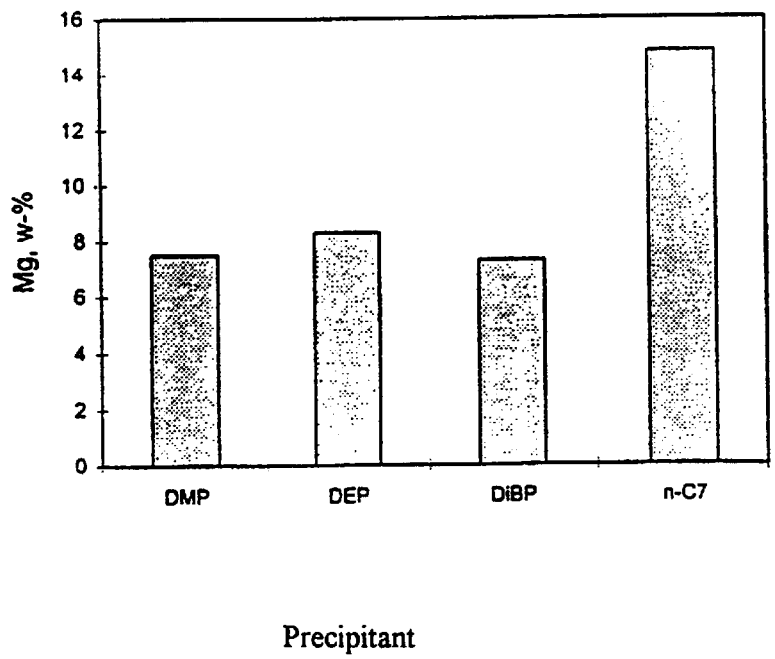
Figure 27. Magnesium concentrations of the compositions

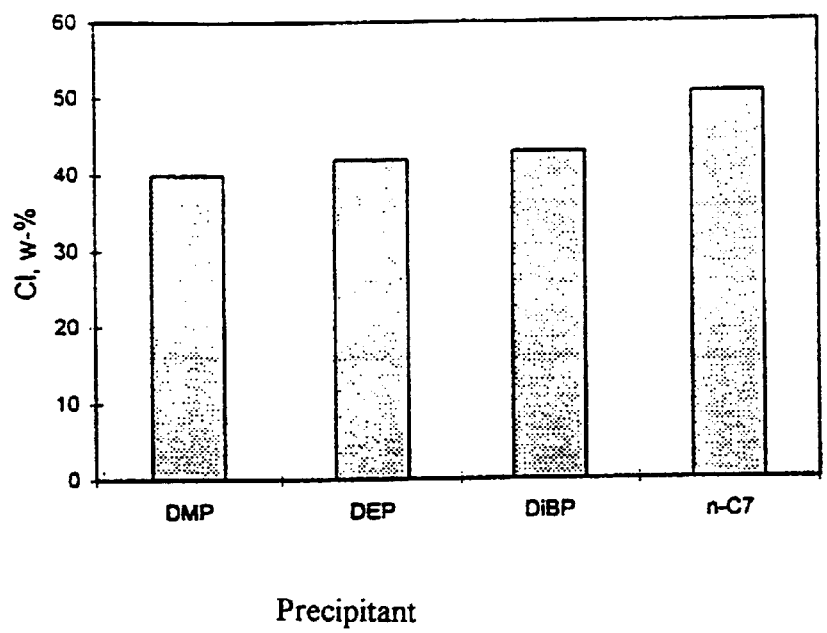
Figure 28. Cl concentrations of the compositions
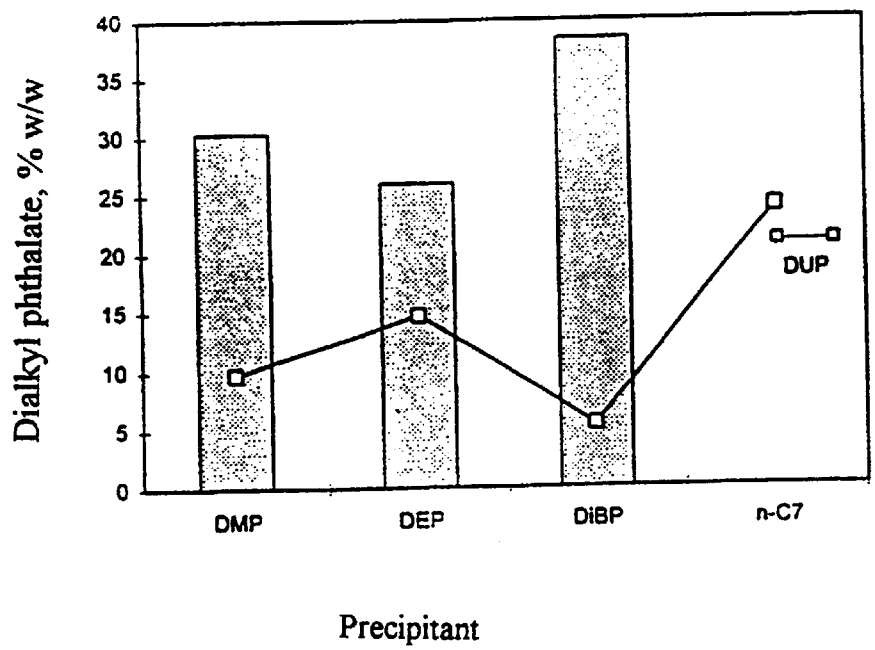
Figure 29. Donor concentrations of the compositions

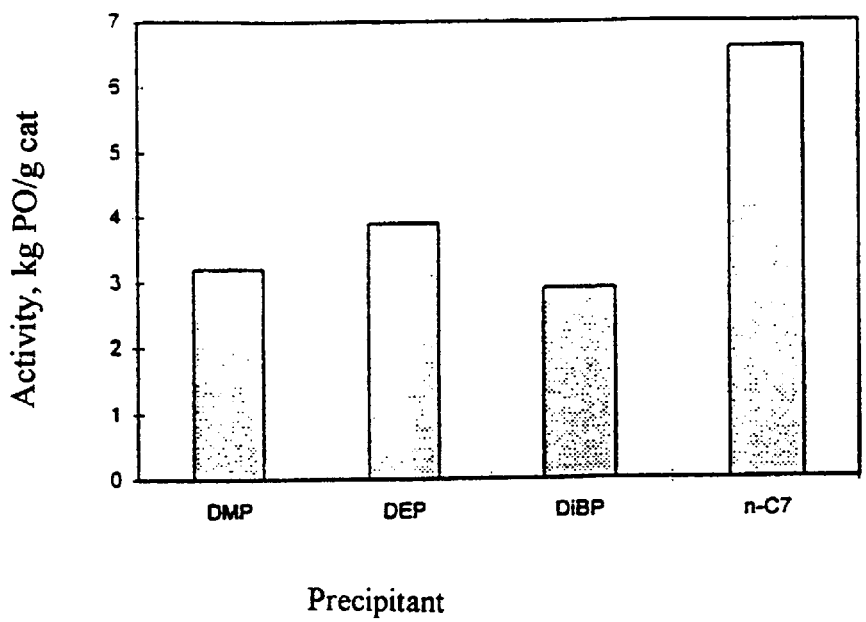
Figure 30. Catalytic activities (kg PP/g cat) of the compositions in bulk homopolymerisation
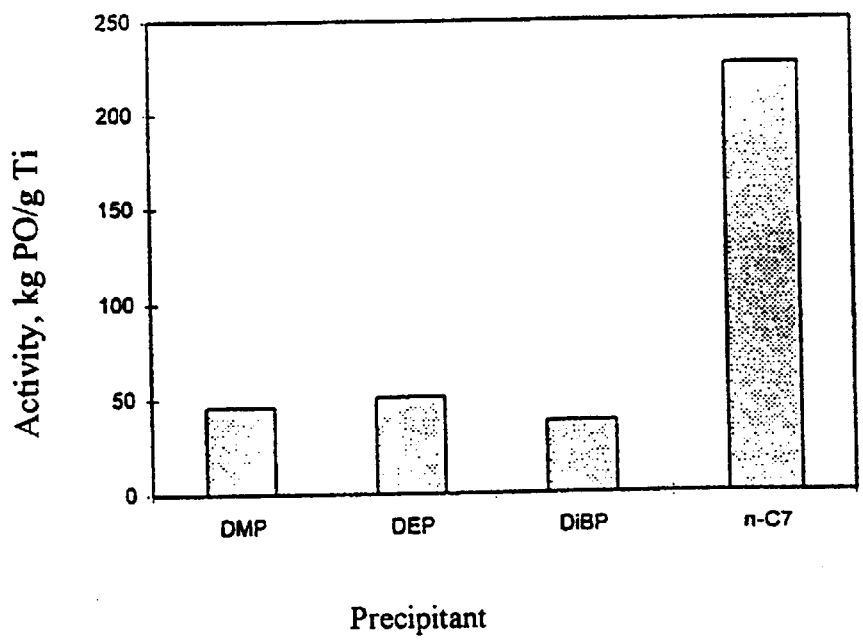
Figure 31. Catalytic activity (kg PP/g Ti) of the compositions in bulk homopolymerisation

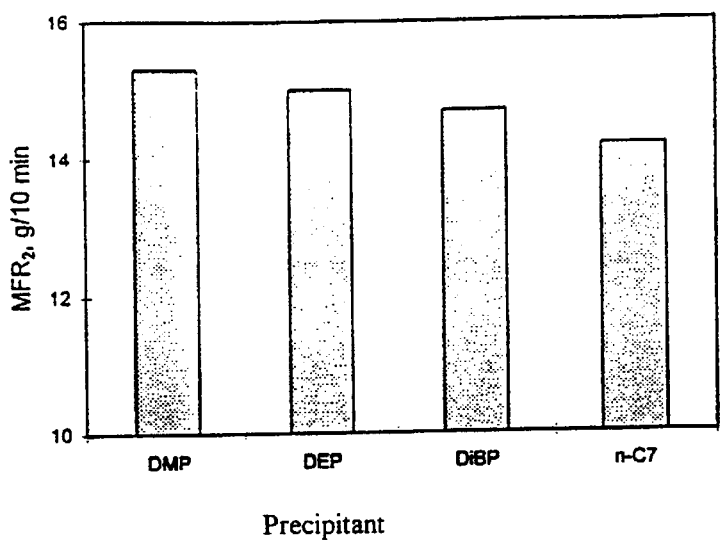
Figure 32. Melt flow rates (MFR) of bulk homopolymers
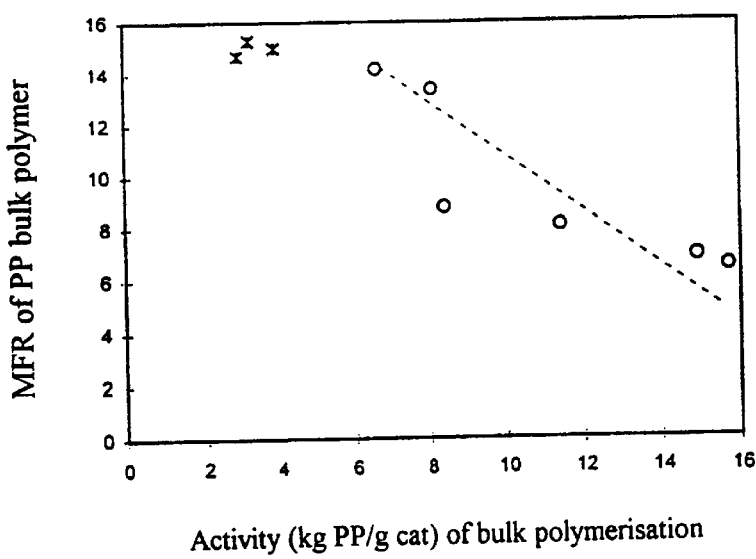
Figure 33. Correlation between melt flow rate of bulk homopolymer and activity of the catalytic composition used
o: catalyst precipitated with n-heptane and washed with toluene
*: catalyst precipitated with donor and washed with toluene

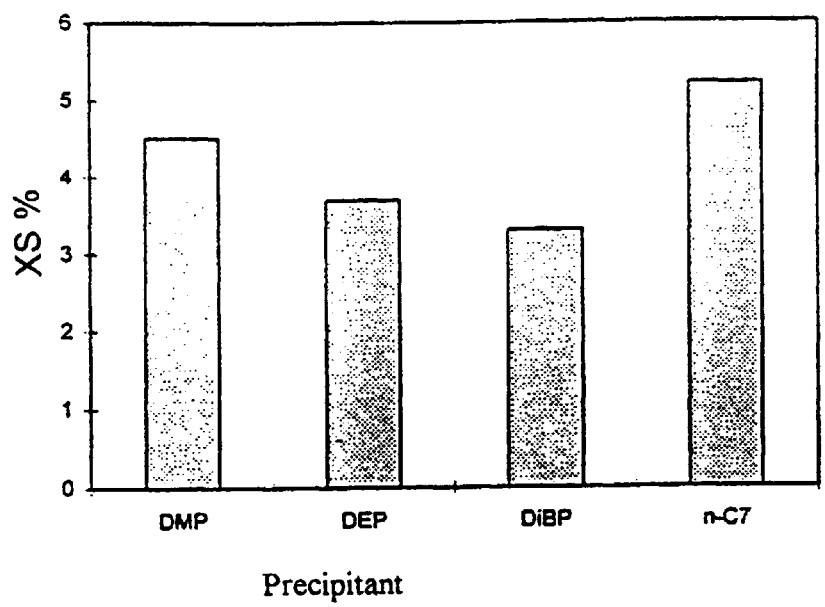
Figure 34. XS percentage values of bulk homopolymers
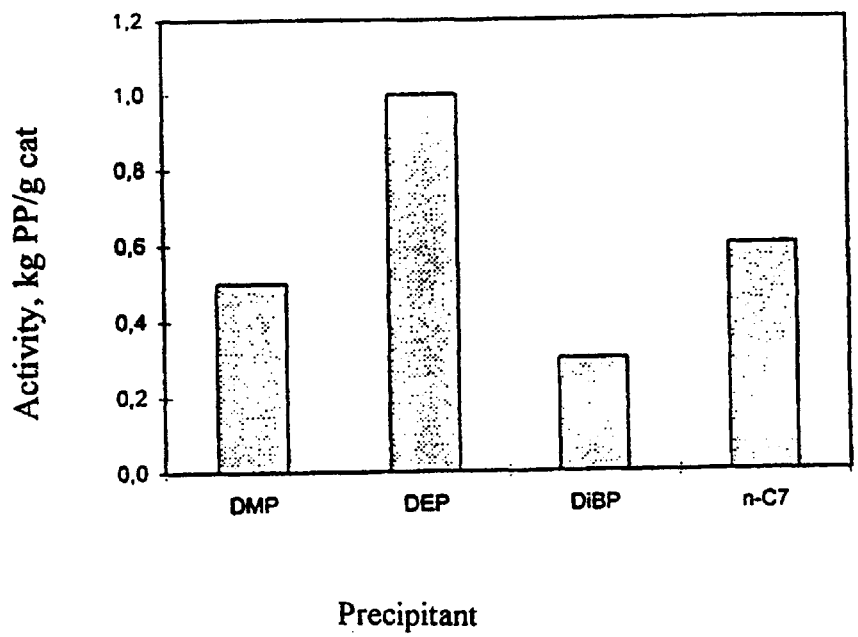
Figure 35. Activities (kg PO/g cat) of the compositions in gas-phase E/P copolymerisation

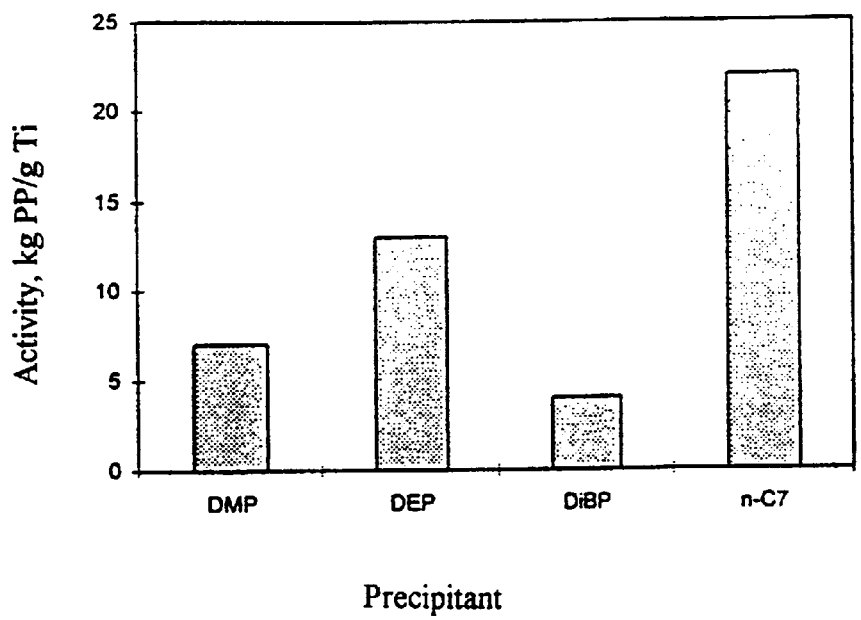
Figure 36. Activities (kg PO/g Ti) of the compositions in gas-phase E/P copolymerisation
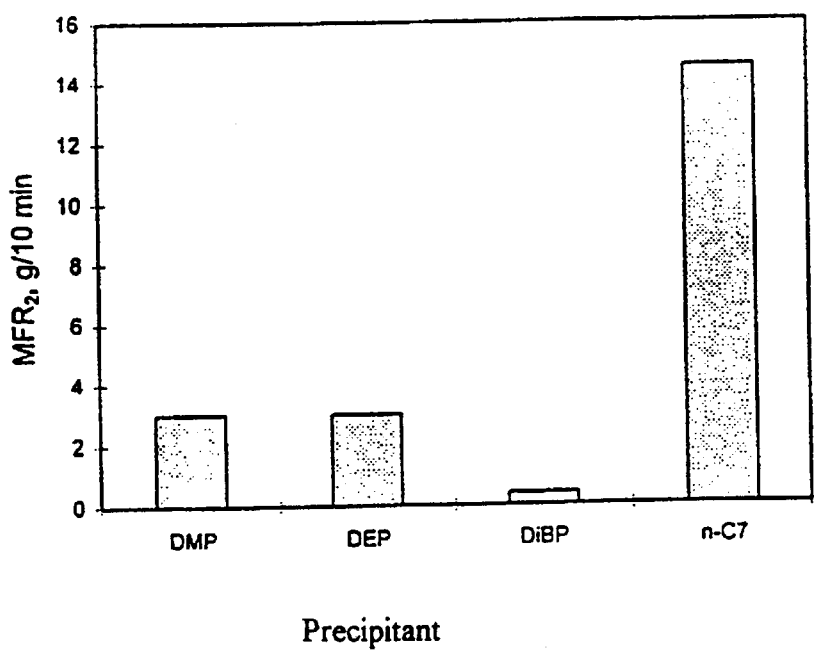
Figure 37. Melt flow rates (MFR) of gas-phase E/P copolymers

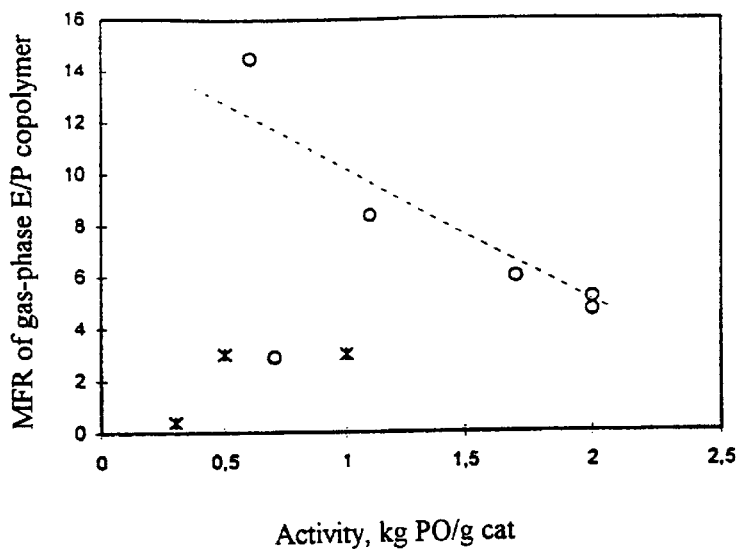
Figure 38. Correlation between melt flow rate of gas-phase E/P copolymer and activity of catalytic polymerisation composition in gas-phase copolymerisation
o: catalyst precipitated with n-heptane and washed with toluene
*: catalyst precipitated with donor and washed with heptane
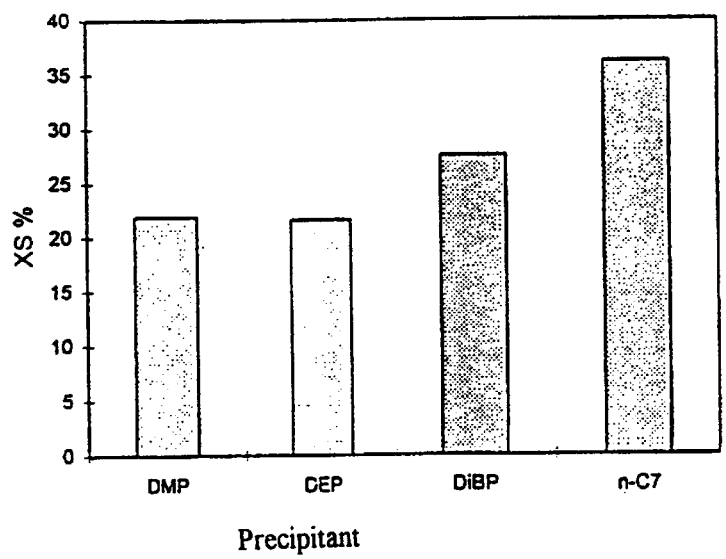
Figure 39. XS-values of gas-phase E/P copolymers

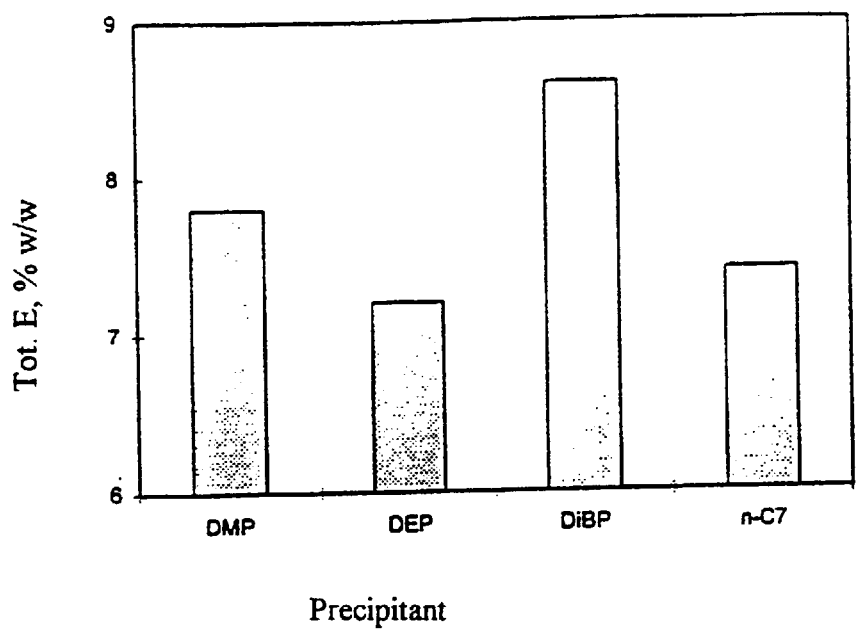
Figure 40. Ethene concentrations of gas-phase E/P copolymers
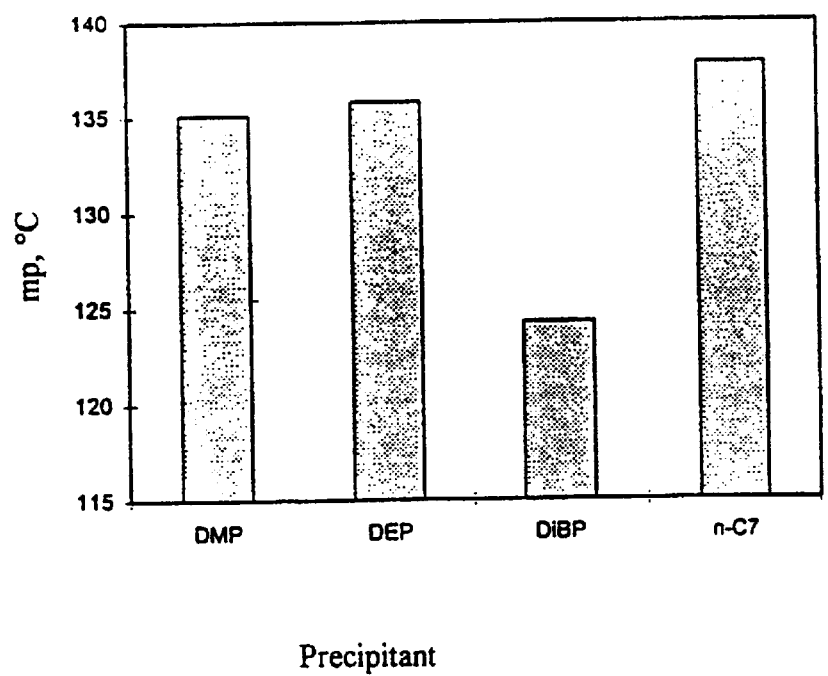
Figure 41. Melting points of gas-phase E/P copolymers

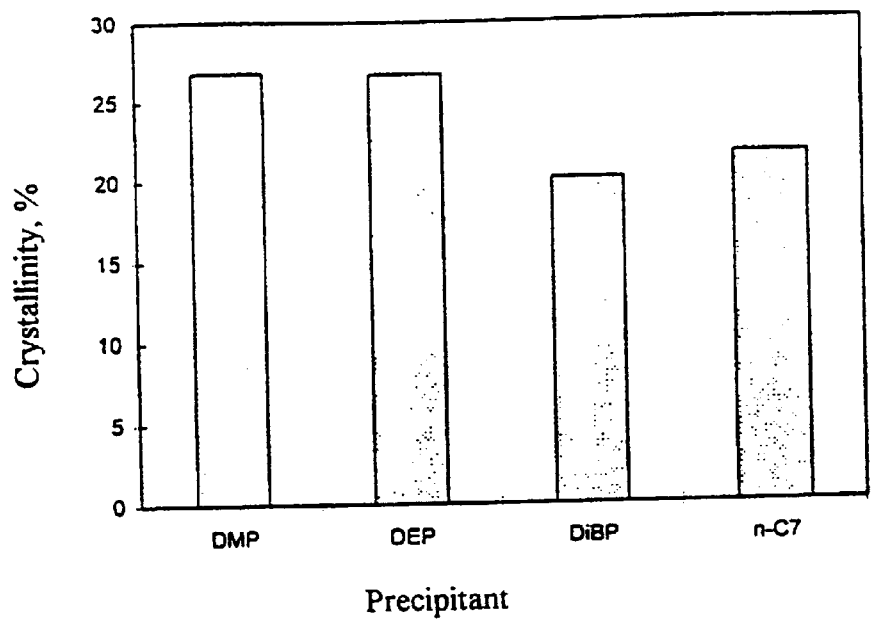
Figure 42. Crystallinities of gas-phase E/P copolymers
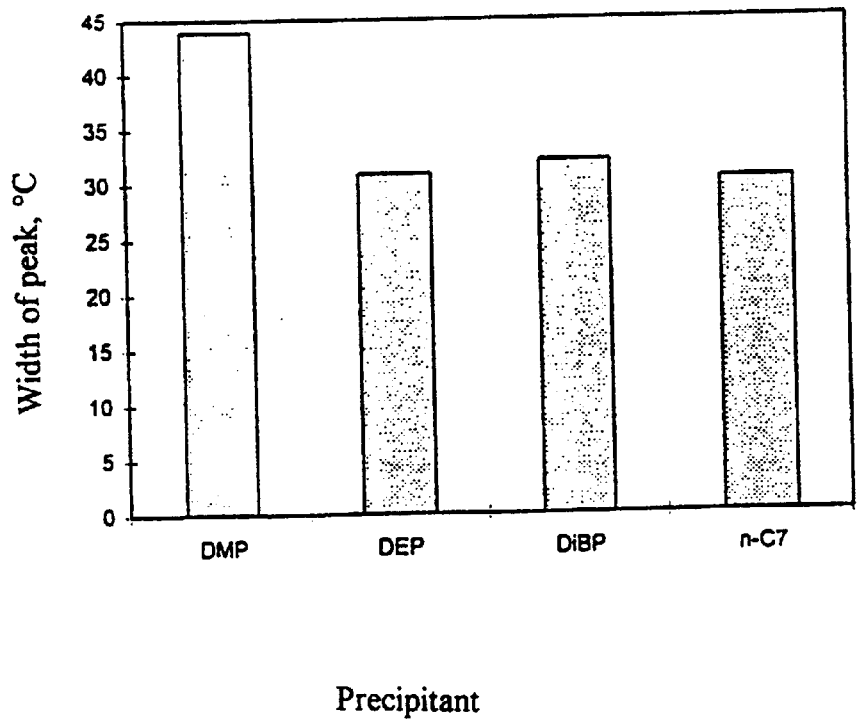
Figure 43a. Widths of DSC peaks of gas-phase E/P copolymers

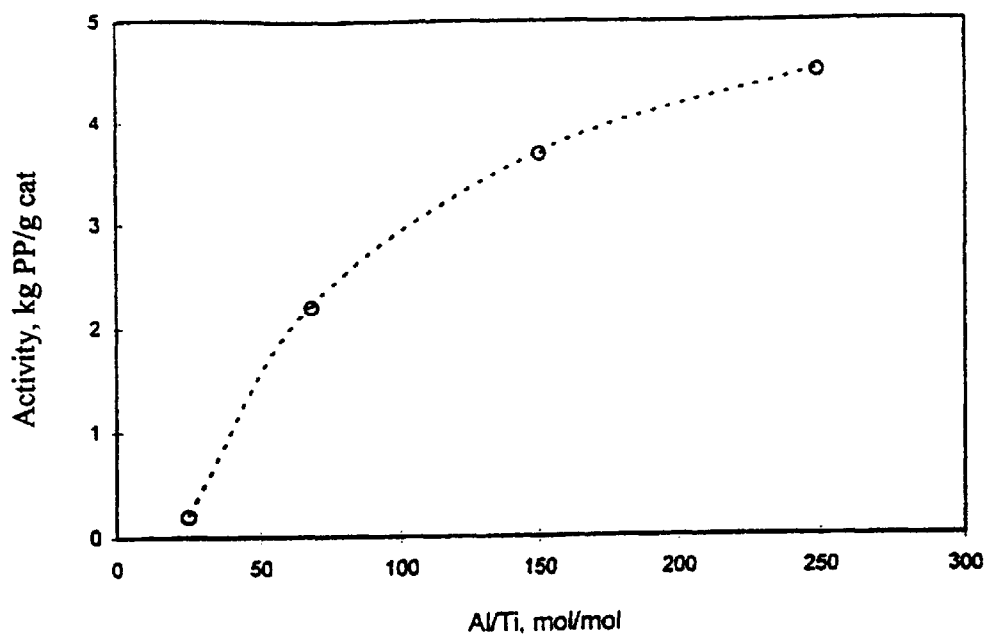
Figure 43b. Homopolymerisation activity of $(MgCl_2)_2TiCl_4DEP$ catalyst complex as function of amount of TEA when $D_2/Ti = 8—10$
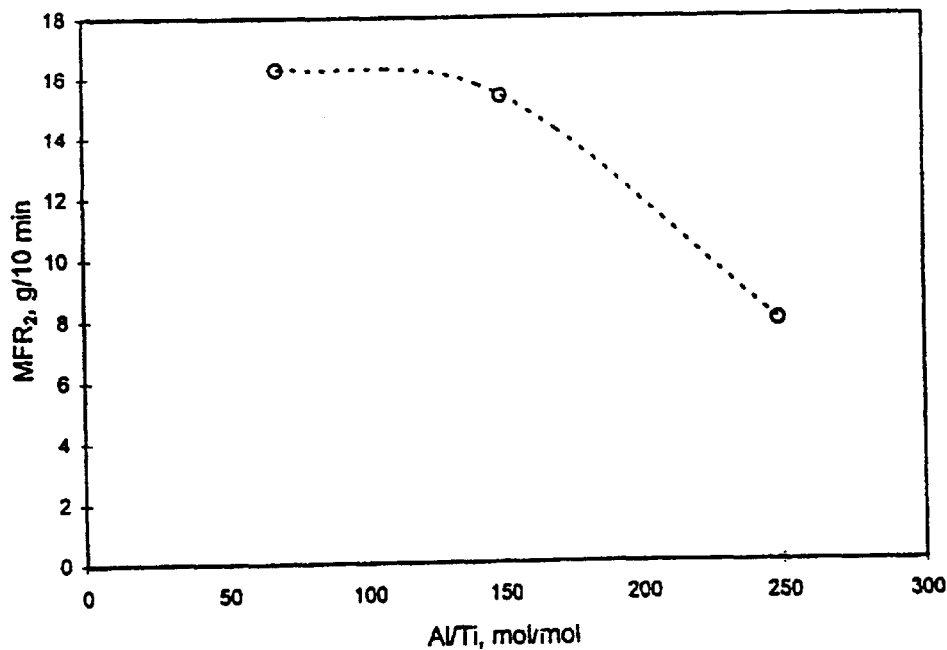
Figure 44. Melt flow rate (MFR) of homopolymer derived with $(MgCl_2)_2TiCl_4DEP$ catalyst complex, as function of amount of TEA, when $D_2/Ti = 8—10$

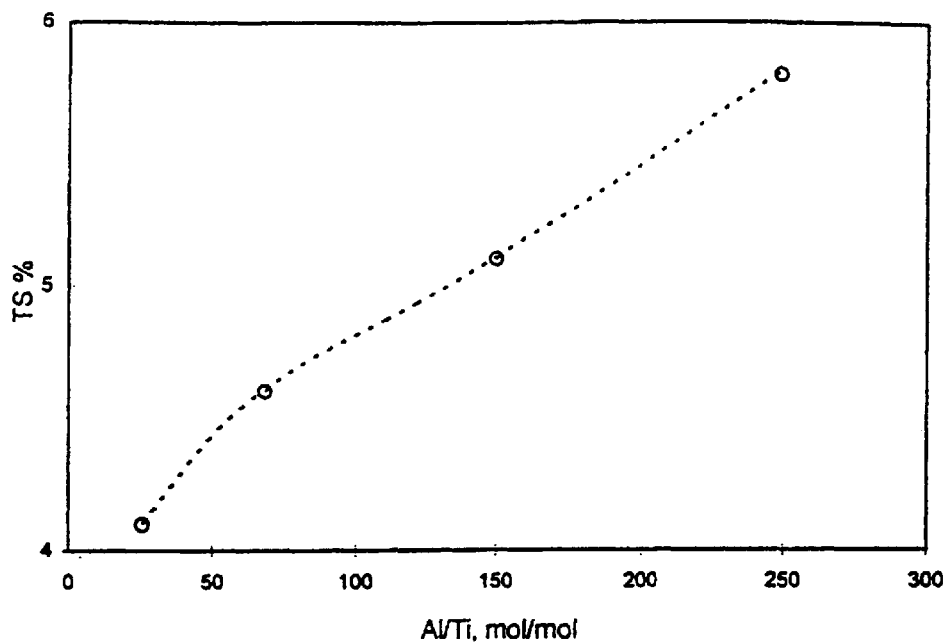
Figure 45. TS of homopolymer as function of molar ratio Al/Ti. Molar ratio $D_2/Ti$ was kept constant in the range 8—10.
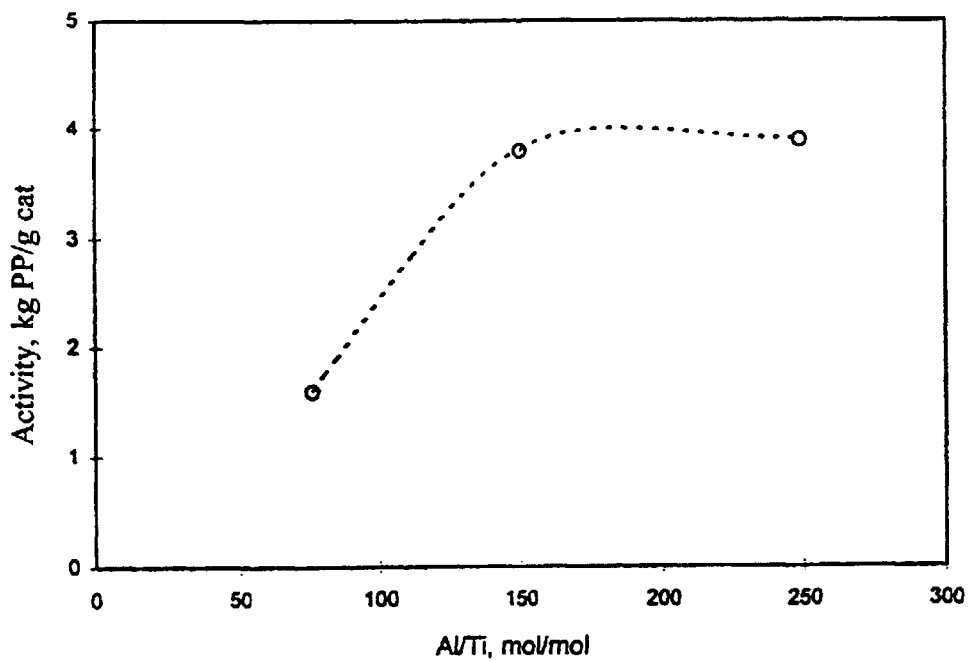
Figure 46. Activity of $(MgCl_2)_2TiCl_4DEP$ catalyst complex as function of amount of TEA used in homopolymerisation when $D_2/Ti$ = constant = 25

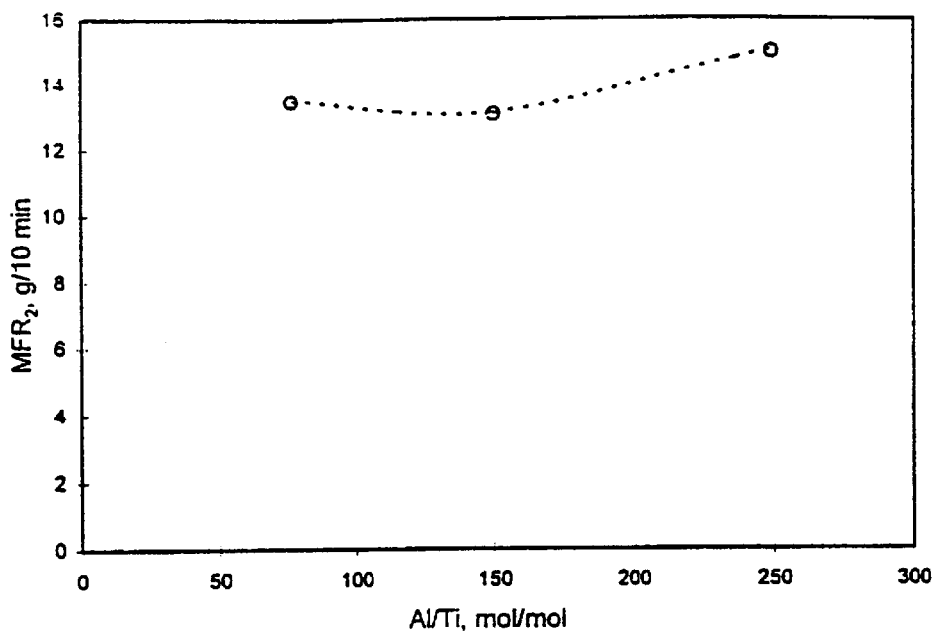
Figure 47. Melt flow rate of homopolymer as function of amount of TEA with use of $(MgCl_2)_2TiCl_4DEP$ catalyst complex. $D_2/Ti$ = constant = 25.
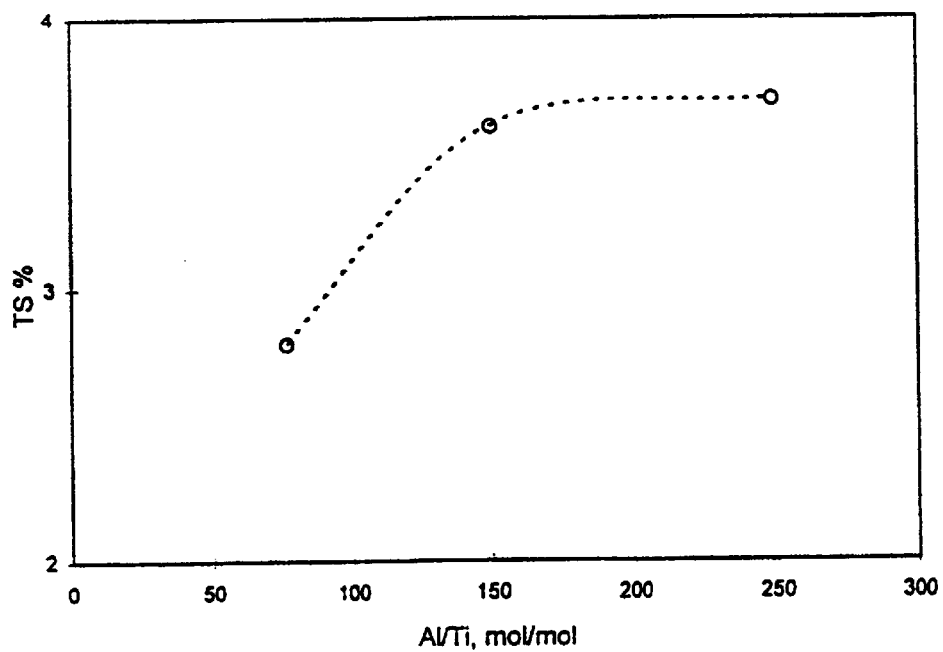
Figure 48. TS of homopolymer as function of molar ratio Al/Ti. $D_2/Ti$ = constant = 25.

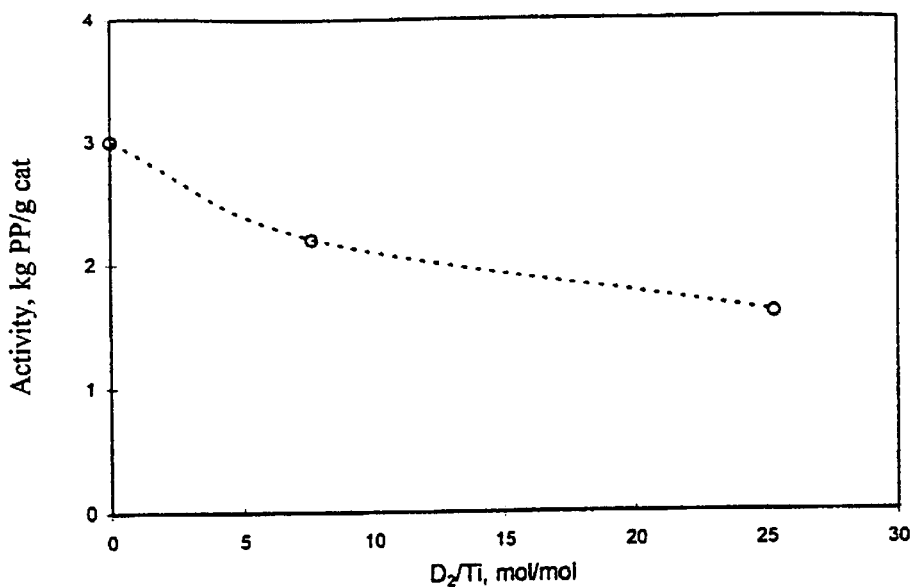
Figure 49. Activity of $(MgCl_2)_2TiCl_4DEP$ complex as function of external donor $D_2$. Al/Ti = constant = 68—76.
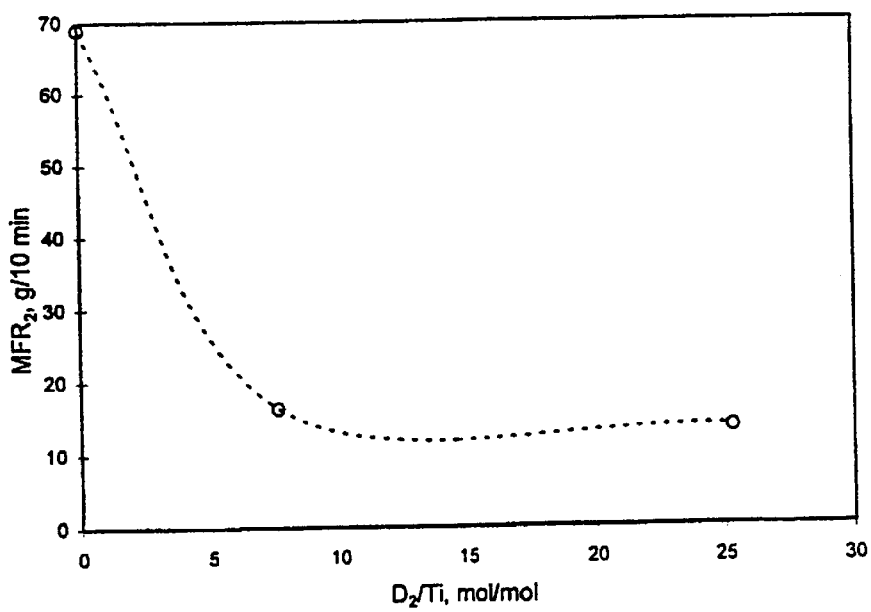
Figure 50. Melt flow rate of homopolymer as function of amount of external donor $D_2$. Al/Ti = constant = 68—76.

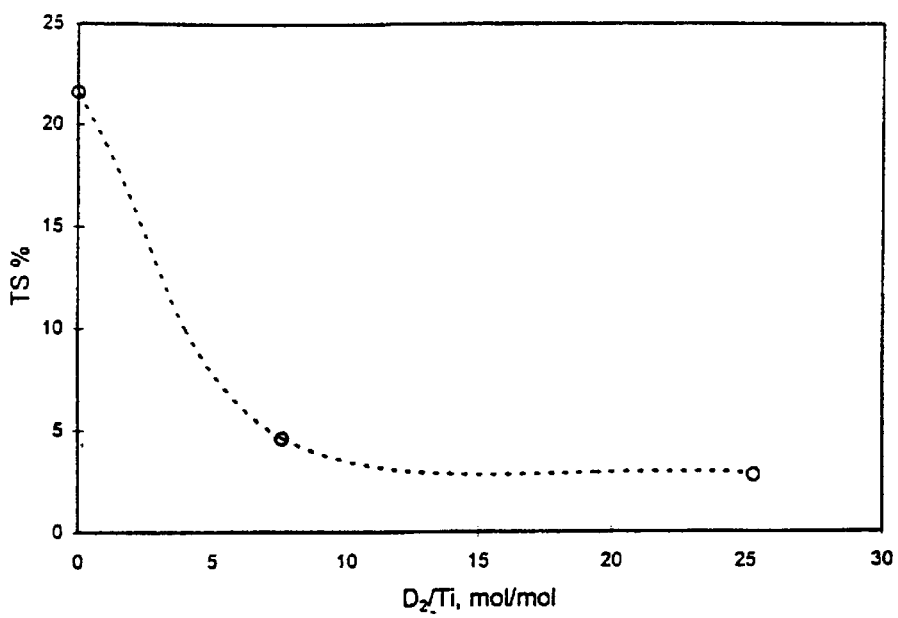
Figure 51. TS value of homopolymer as function of molar ratio $D_2/Ti$. TEA = constant = 68—76.
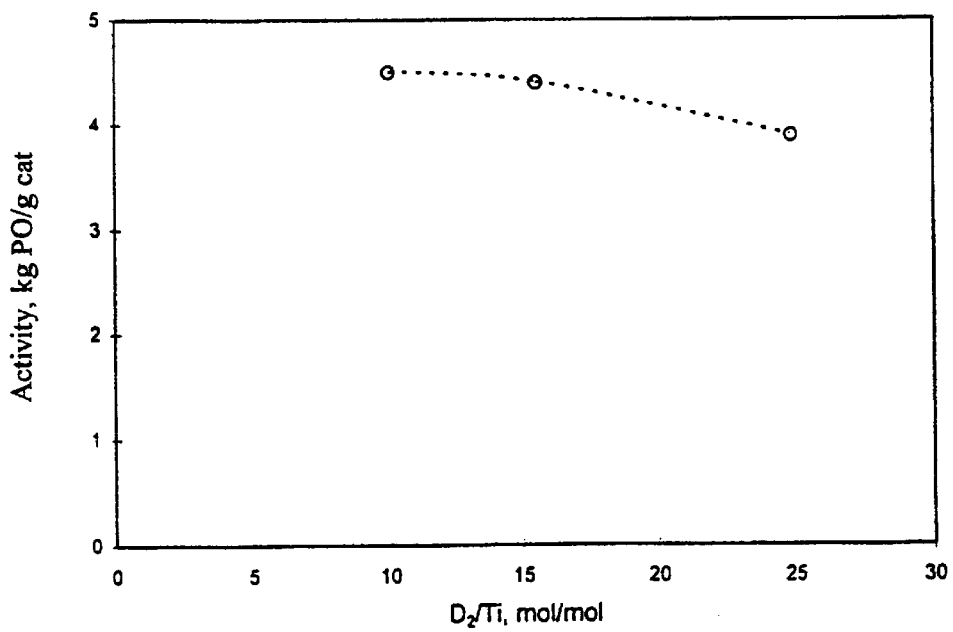
Figure 52. Activity of $(MgCl_2)_2TiCl_4DEP$ complex as function of amount of external donor $D_2$. Al/Ti = constant = 250.

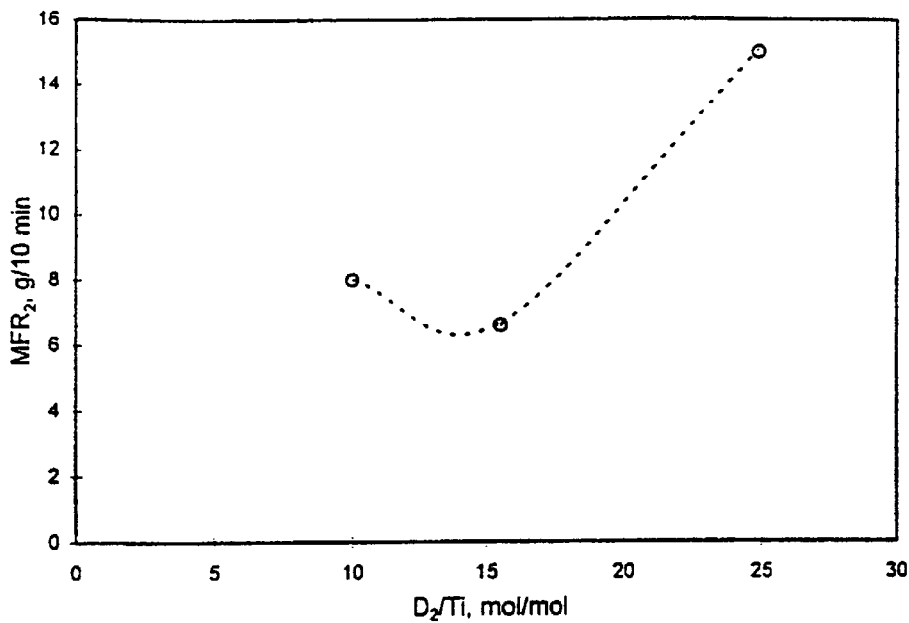
Figure 53. Melt flow rate (MFR) of homopolymer as function of amount of external donor $D_2$. Al/Ti = constant = 250.
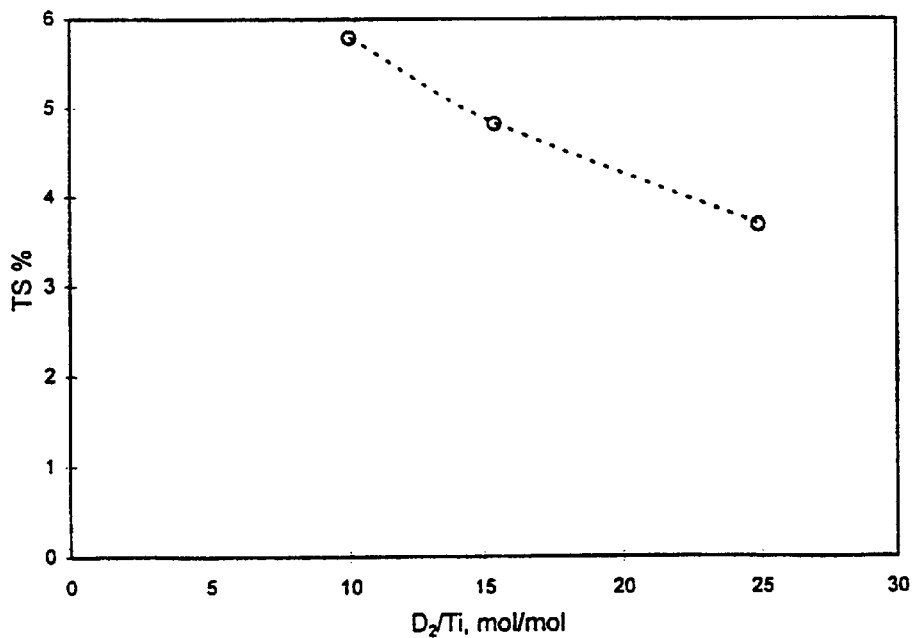
Figure 54. TS value of homopolymer as function of ratio $D_2$/Ti. Al/Ti = constant = 250.

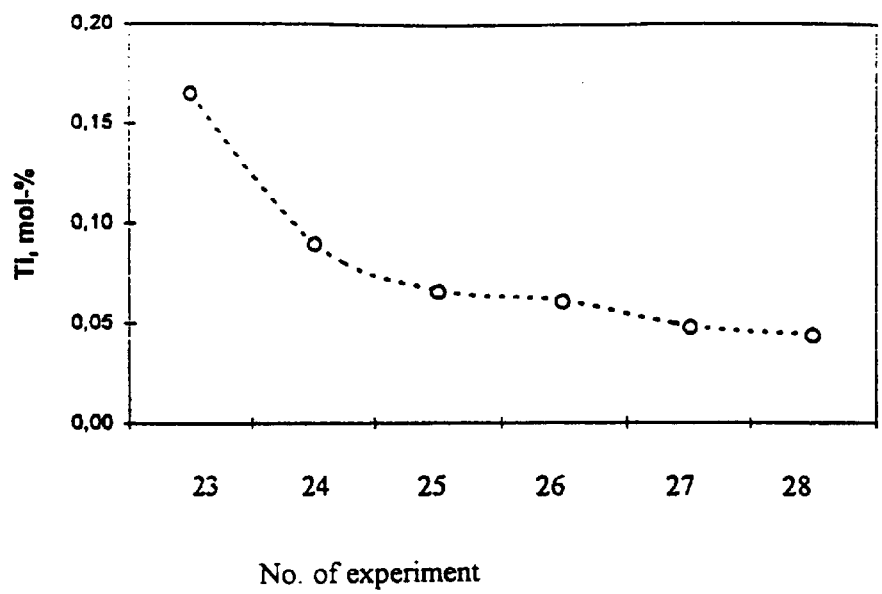
Figure 55. Reduction in molar-% of Ti of composition as function of increasing washing power
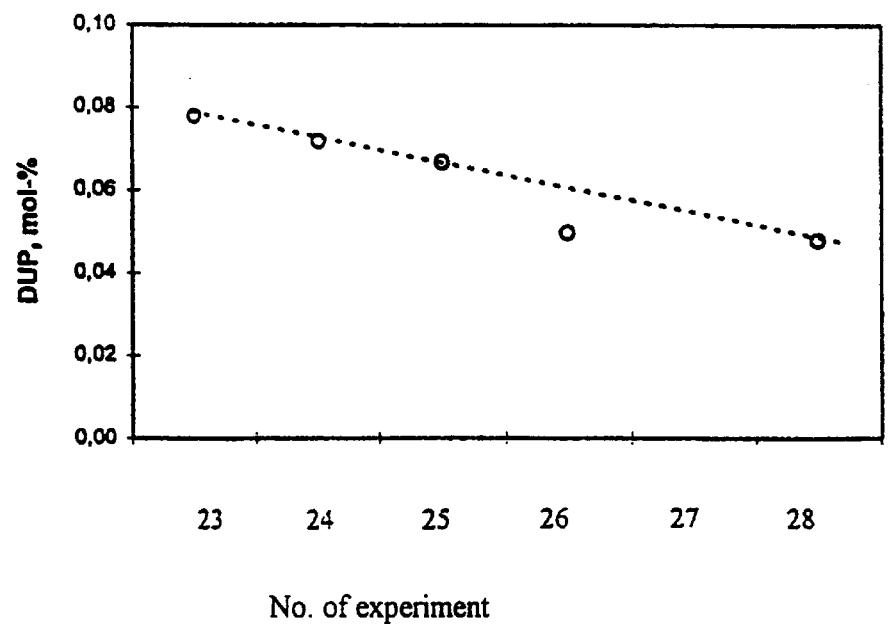
Figure 56. Reduction in molar-% of DUP of composition as function of increasing washing power

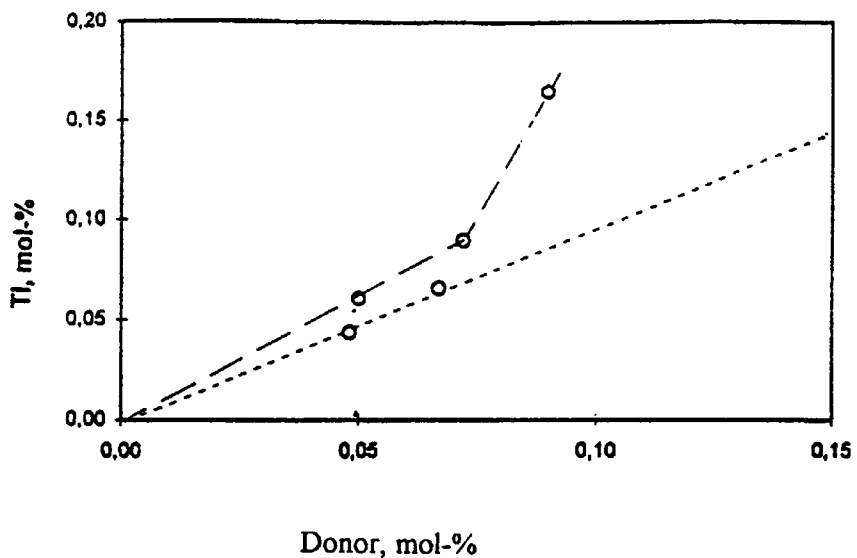
Figure 57. Correlation between molar-% of Ti and molar-% of donor. Dotted line refers to composition with Ti/D = 1:1.
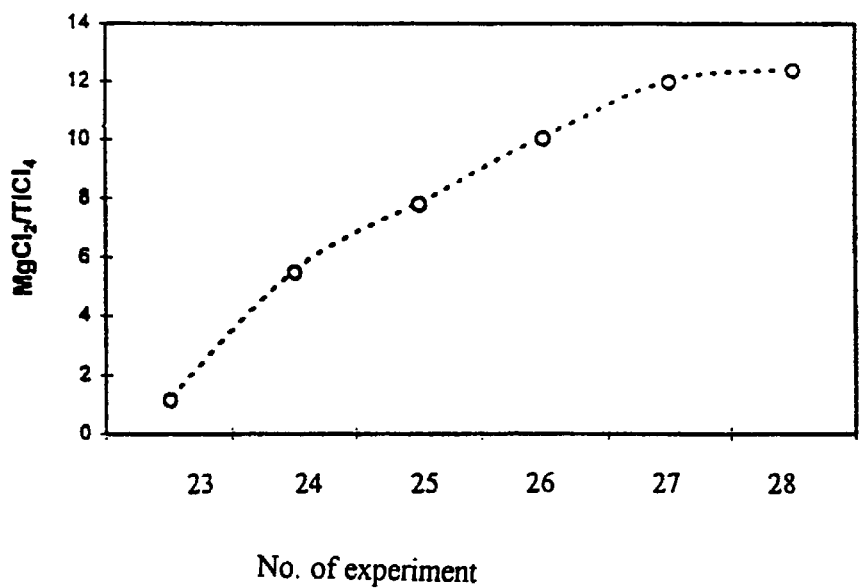
Figure 58. Increase in $MgCl_2$ concentration as function of washing power

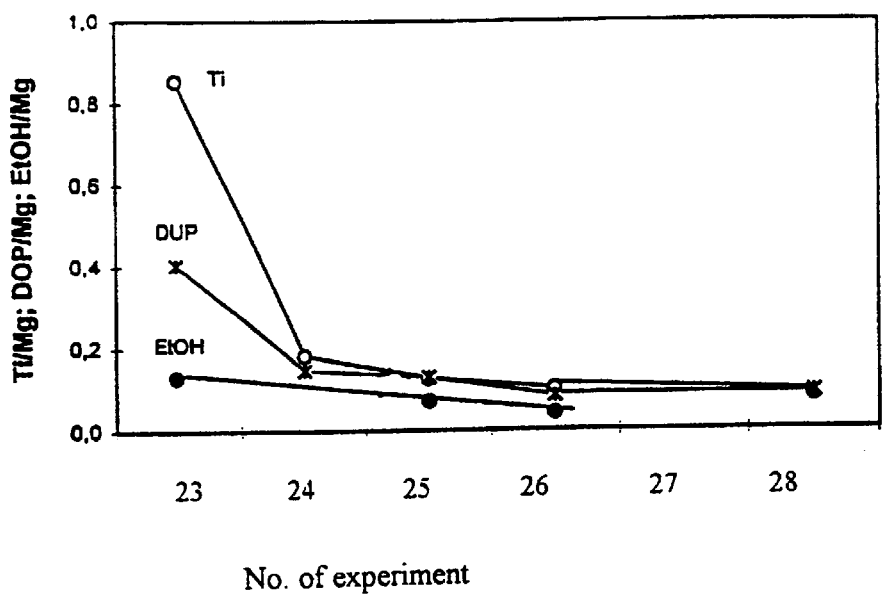
Figure 59. Molar ratios Ti/Mg, DUP/Mg and EtOH/Mg of the compositions
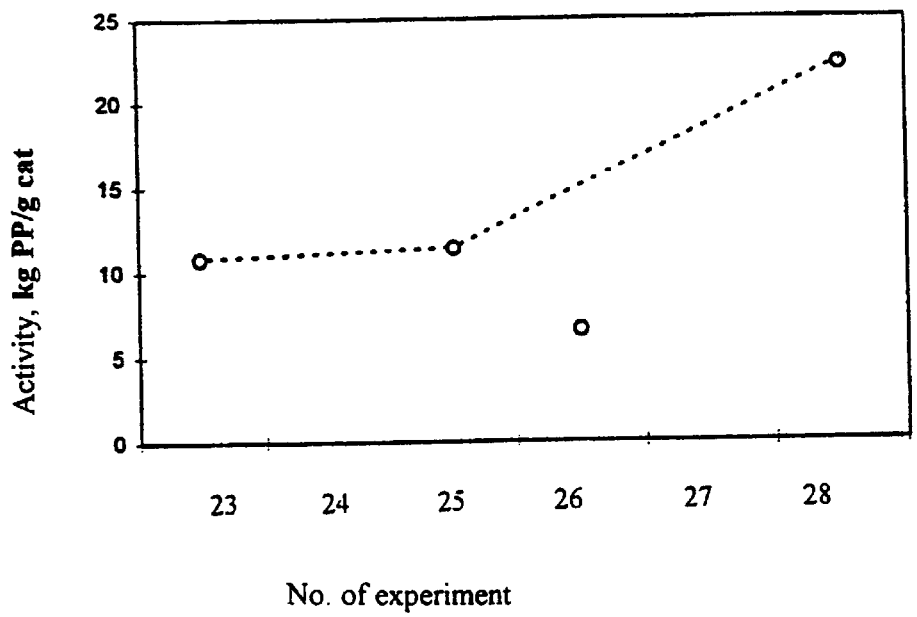
Figure 60. Activity of composition as function of washing power

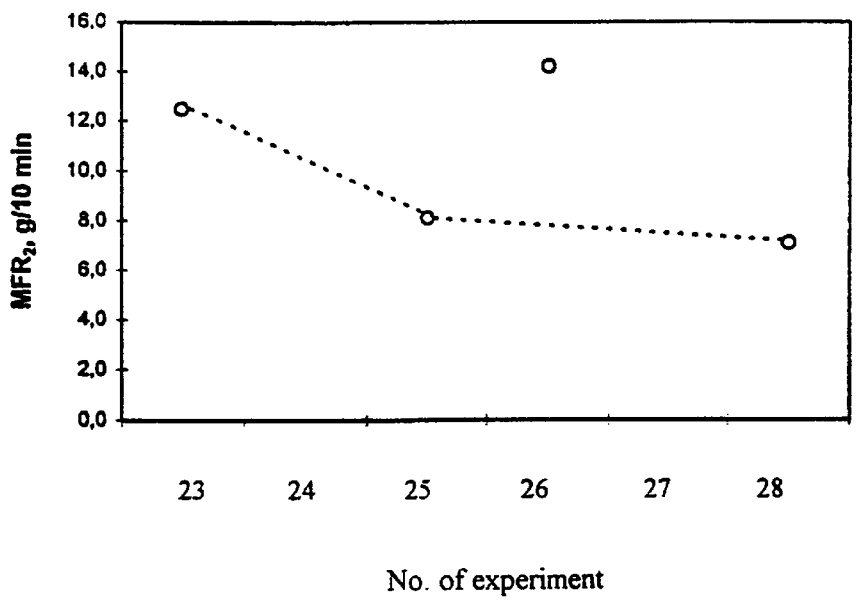
Figure 61. Melt flow rates (MFR) of polymers derived with the compositions
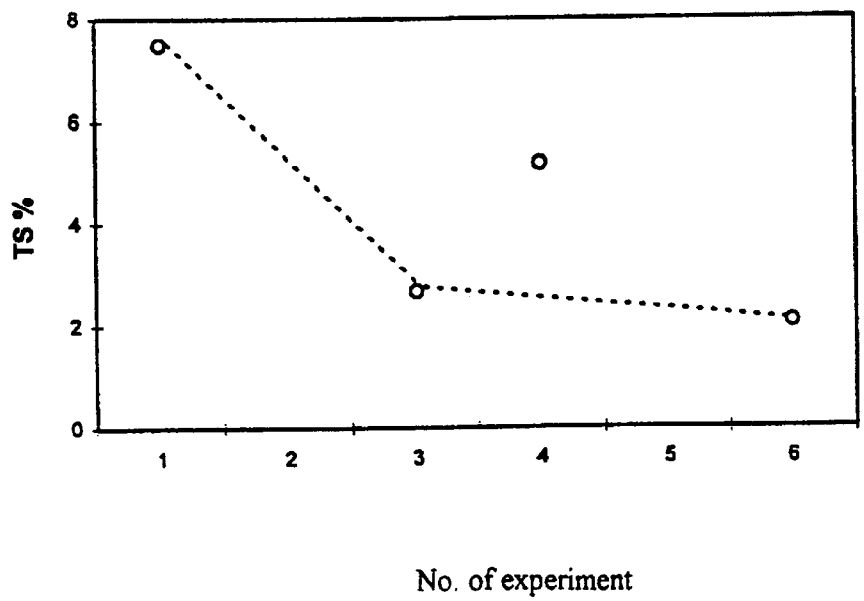
Figure 62. TS value of polymer derived with composition as function of washing power

COMPOSITION CONTAINING MAGNESIUM, TITANIUM, HALOGEN AND AN INNER ELECTRON DONOR, ITS PREPARATION AND USE FOR THE POLYMERIZATION OF ALPHA-OLEFINS

This application is the national phase under 35 U.S.C. §371 of prior PCT International Application No. PCT/FI97/00191 which has an International filing date of Mar. 26, 1997 which designated the United States of America, the entire contents of which are hereby incorporated by reference.

The present invention relates to compositions containing magnesium, titanium, halogen and a carboxylic acid ester. The invention also relates to such compositions prepared by bringing into contact with each other at a certain temperature and reacting the complex $MgX^1_2 \cdot nR^1OH$, where $X^1$ is a halogen, $R^1$ is a $C_1$–$C_{20}$ alkyl and n is in the range 2.0–6.4, a titanium tetrahalide, $TiX^2_4$, where $X^2$ is a halogen, and a carboxylic acid ester.

The invention further relates to the above-mentioned type of method for preparation of a composition containing magnesium, titanium, halogen and a carboxylic acid ester. Finally, the invention relates to a method for polymerisation of α-olefins by bringing into contact with each other and reacting a procatalyst, which is an above-mentioned type of composition containing magnesium, titanium, halogen and a carboxylic acid ester or which contains such a composition, a cocatalyst, which is an organometallic compound of a metal belonging to one of groups 1, 2 or 13 of the periodic system, preferably an external donor with at least one ligand atom capable of donating an electron, and one or more α-olefins.

Polymerisation catalysts, especially Ziegler-Natta type of polymerisation catalysts, nowadays typically comprise an inert solid carrier upon which the actual active catalyst component or a mixture or complex of catalytic compounds is layered. The chemical composition, surface structure, morphology, particle size and particle size distribution of such a heterogeneous catalytic system are very important for the activity of the catalyst and for the properties of the polymer obtained by means of the catalyst. As it is, a very active catalyst can yield a polymer and, in particular, a poly-α-olefin that is so pure as to require no removal of catalyst residues.

The above-mentioned type of heterogeneous catalytic systems nowadays often comprise a magnesium-based carrier treated with a transition-metal compound, such as a titanium halide, and often even with an electron-donating compound. It is also known that the carrier can be furnished with a favourable chemical composition, surface structure, morphology, particle size and particle size distribution by allowing it to crystallise as a complex of one of its crystal solvents.

In a method according to EP 65700 and U.S. Pat. No. 4,421,674, a titanium halide is made to react with a magnesium chloride catalyst carrier in microsphere form whereafter the particles of reaction product are recovered by physical means and mixed with an organometallic cocatalytic compound.

FI patent application 862459 presents a method for carrier preparation where a carrier complex consisting of a carrier substance, such as magnesium chloride, $MgCl_2$, and a crystal solvent, such as ethanol, $C_2H_5OH$, is melted into a clear liquid. When this liquid is conducted through a nozzle and an atomising chamber into a crystallisation chamber cooled with cold nitrogen gas, the carrier complex is crystallised into small spherical particles. When the carrier thus activated is brought into contact with a titanium halide, such as titanium tetrachloride, $TiCl_4$, and the crystal solvent is eliminated, a large amount of catalytically active complexes between the carrier substance, such as $MgCl_2$, and the titanium halide, such as titanium tetrachloride, $TiCl_4$, are formed on the surface of the solid carrier.

There is now invented a novel composition that consists of magnesium, titanium, halogen and a carboxylic acid ester and is in the liquid state and preferably soluble. There is also invented a method by which the said composition in the liquid state is brought about. The composition is prepared by bringing into contact with each other at a prescribed temperature and reacting the complex $MgX^1_2 \cdot nR^1OH$, where $X^1$ is a halogen, $R^1$ is a $C_1$–$C_{20}$ alkyl, and n is in the range 2.0–6.4, a titanium tetrahalide, $TiX^2_4$, where $X^2$ is a halogen, and a carboxylic acid ester, to yield a reaction product. In the course of the preparation, the composition is brought into the liquid state by using:

(a) as the said carboxylic acid ester, a compound that contains at least 8·j carbon atoms and is compatible with the following formula (I)

$$R^2(COOR^3)_j \qquad (I)$$

where $R^2$ is a j-valent substituted or unsubstituted $C_1$–$C_{34}$ hydrocarbon group, $R^3$ is a $C_6$–$C_{20}$ alkyl group, and j is an integer from 1 to 4;

(b) a molar ratio $R^2(COOR^3)_j/MgX^1 \cdot nR^1OH$ that is ≧approximately 0.8/j;

(c) a molar ratio $TiX^2_4/MgX^1_2 \cdot nR^1OH$ that is ≧approximately n;

(d) possibly an organic dissolvent substance S; and (e) a temperature that is in the range 40–200° C.

Thus, it has been realised that the previous heterogeneous reaction among the solid complex $MgX^1_2 \cdot nR^1OH$, a titanium tetrahalide, $TiX^2_4$, and an ester-like inner composition can be altered to a homogeneous reaction if the above-mentioned conditions (a)–(e) are met. By using a greater than usual amount of a more dissolvent carboxylic acid ester in combination with an excess amount of titanium tetrahalide and/or an organic dissolvent substance at a more or less elevated temperature, the composition is surprisingly obtained in the liquid state, usually in dissolved form.

An embodiment of the invention uses such a molar ratio $TiX^2_4/MgX^1_2 \cdot nR^1OH$ as yields the resultant composition as dissolved in the excess amount of titanium tetrahalide (in respect of the alcohol, $R^1OH$). As it is, the titanium tetrahalide reacts with the alcohol of the said complex so that an excess amount of titanium tetrahalide in respect of the alcohol in the complex is required to dissolve the said complex. Titanium tetrahalide and the said complex are brought into contact with each other at a molar ratio $TiX^2_4/MgX^1_2 \cdot nR^1OH$ that is preferably ≧1.7·n, and with n in the range 2.0–6.4 (see above), the said ratio is more preferably in the range 10–100 and most preferably in the range 20–50.

The molar ratio between the said carboxylic acid ester and the said complex may vary in a wide range, provided it is ≧approximately 0.8/j (see above). j is the number of carboxyl ester groups of the carboxylic acid ester. When the said carboxylic acid ester reacts with titanium tetrahalide and the said complex, the said carboxyl ester groups function as the electron-donating groups of the carboxylic acid ester. Since a limited number of coordination sites are formed in the mixture, a greater molar amount of the carboxylic acid ester is needed to fill these sites if there are few carboxyl ester groups, i.e., if j is small. Therefore, the above-presented minimum molar ratio depends on the number of carboxyl ester groups in the carboxylic acid ester. For instance, if a dicarboxylic acid is used, j=2 and the said molar ratio between the carboxylic acid ester and the complex is $\geq 0.8/2$, or $\geq 0.4$. The molar ratio between the said carboxylic acid ester and the complex is preferably $\geq$ approximately $1/j$ and most preferably in the range of approximately $1/j$–$20/j$.

As mentioned above, the said composition is obtained in the liquid state by heating the composition to a temperature of 40 to 200° C. The temperature to be applied depends on the identities and quantities of the carboxylic acid ester, titanium tetrahalide and possible organic dissolvent substance used, and therefore the scope of protection of the invention, with regard to the temperature applied, should in this context be interpreted according to the equivalence principle. The preferable temperature is 60° C. to approximately 140° C. and the most preferable temperature in the range 80–120° C.

Thus, a composition according to the invention is brought about by means of a carboxylic acid ester compatible with formula (I). It is preferable that the carboxylic acid ester, $R^2(COOR^3)_j$, containing at least 8·j carbon atoms has one or two carboxyl ester groups, i.e., j is 1 or 2. The potential alternatives then comprise saturated and unsaturated aliphatic, including cycloaliphatic, carboxylic acid esters and various aromatic carboxylic acid esters. In a preferable embodiment, the carboxylic acid ester, $R^2(COOR^3)_j$, is a carboxylic acid ester containing at least 12 carbon atoms, preferably an ester of an $\alpha,\beta$-unsaturated carboxylic acid, more preferably an ester of an aromatic carboxylic acid, even more preferably a di-$C_6$–$C_{20}$ alkyl ester of phthalic acid and most preferably a di- $C_8$–$C_{14}$ alkyl ester of phthalic acid. The alkyls may be branched or linear. Such preferable esters include di-2-ethylhexyl phthalate, dioctyl phthalate, dinonyl phthalate, didecyl phthalate, diundecyl phthalate, didodecyl phthalate, ditridecyl phthalate and ditetradecyl phthalate.

The $X^1$ and/or $X^2$ in formula (I) are/is preferably chlorines/chlorine. Thus, a composition according to the invention is preferably based on magnesium chloride, $MgCl_2$, and titanium tetrachloride, $TiCl_4$.

It is preferable that a composition according to the invention be prepared using a complex $MgX^1_2 \cdot nR^1OH$ where the $R^1$ group of the alcohol is a $C_1$–$C_2$ alkyl, preferably a $C_2C_8$ alkyl. In preparing the said complex from a magnesium halide and an alcohol, the alcohol used may be, for instance, methanol, ethanol, n-propanol, n-butanol or 2-ethyl-1-hexanol. The complex may be prepared using any customary method reported in the literature. Two practicable methods are the so-called spray crystallisation process where a magnesium halide, such as magnesium chloride, and an alcohol, such as ethanol, are reacted and melted into a clear liquid which is then sprayed into a cold crystallisation chamber to yield small spherical particles, and the emulsification method where a magnesium halide, such as magnesium chloride, and an alcohol, such as ethanol, are added together with an emulsifying agent to an inert heat-resistant oil, heated into a molten reaction product, stirred vigorously to create a fine dispersion and precipitated by pouring the dispersion into cold hydrocarbon.

Although a composition according to the present invention can be produced by dissolving the complex, the titanium tetrahalide and the carboxylic acid ester, or their reaction product, in excess titanium tetrahalide, it is nevertheless preferable to add to the reaction mixture at least a small amount of an organic substance enhancing the dissolution of the reaction product. Preferably, the complex, the titanium tetrahalide and the carboxylic acid ester are brought into contact with a chlorinated hydrocarbon, such as carbon tetrachloride or trichloroethylene, or an aromatic hydrocarbon, such as toluene. In these instances, smaller or larger amounts of an organic substance S dissolving the reaction product may be used but a preferable molar ratio $TiX^2_4/S$ is in the range 0.5–20 and the most preferable in the range 1–6.

In preparing a composition containing magnesium, titanium, halogen and a carboxylic acid ester according to the invention, the complex, titanium tetrahalide and the carboxylic acid ester can be introduced in any desired sequence. It is, nevertheless, preferable to use a sequence where the complex $MgX^1_2 \cdot nR^1OH$, a possible organic dissolvent substance and the titanium tetrahalide, $TiX^24$, are first added, preferably in this order, and then the carboxylic acid ester, $R^2(COOR^3)_j$, is added.

A composition according to the invention can be recovered in the liquid state, preferably in dissolved form, and used for the most varied purposes either as such or after re-dissolution. One of its uses is as a homogeneous (liquid) catalyst of $\alpha$-olefin polymerisation and another as a homogeneous (liquid) staring material for other catalysts or catalytic systems.

In a preferable embodiment, a composition according to the invention is prepared by recovering the said liquid composition in the solid state. This is preferably done by precipitating the dissolved composition. In an embodiment, the precipitation is done by cooling the liquid composition. In another embodiment, precipitation is done by bringing the dissolved composition into contact with a substance that will precipitate it but will not remain a part of the product, preferably with an aliphatic $C_5$–$C_{12}$ hydrocarbon, more preferably so that the molar ratio between the aliphatic $C_5$–$C_{12}$ hydrocarbon and the titanium tetrachloride of the dissolved composition is in the range 0.05–5, most preferably in the range 0.1–2. Typical precipitant hydrocarbons include pentane, hexane, heptane, octane, nonane and decane. Other precipitant hydrocarbons include mixtures of aliphatic hydrocarbons.

Precipitation using a hydrocarbon is typically done by lowering the temperature of the liquid composition and adding a sufficient amount of preferably aliphatic hydrocarbon, such as heptane. The composition will then precipitate whereafter any dissolved material, comprising e.g. titanium tetrachloride, $TiCl_4$, titanium trichloride alkoxide, $TiCl_3OR$, and toluene, that remains in the aliphatic hydrocarbon is decanted off with the solution. The solid obtained, known as the first composition, can then be washed, preferably several times, and finally dried and, if required, analysed and used.

In another embodiment of the invention, the composition (not the so-called first composition) can be recovered in the solid state by bringing the dissolved composition into contact with and making it to react with a reagent that precipitates it. This reagent is usually a second carboxylic acid ester which replaces the carboxylic acid ester of the said liquid composition, thus converting the first composition into an insoluble second composition. The precipitant agent thus remains a part of the product.

It is preferable that the second carboxylic acid ester be a compound compatible with the following formula (II)

$$R^4(COOR^5)_j \qquad (II)$$

where $R^4$ is a j-valent substituted or unsubstituted $C_1$–$C_{34}$ hydrocarbon group, $R^5$ is a $C_1$–$C_5$ alkyl group and j is an integer from 1 to 4. The second carboxylic acid ester is preferably a $C_1$–$C_5$ alkyl ester of an α,β-unsaturated carboxylic acid, more preferably a $C_1$–$C_5$ alkyl ester of an aromatic carboxylic acid, even more preferably a di- $C_1$–$C_5$ alkyl ester of phthalic acid and most preferably a di- $C_1$–$C_4$ alkyl ester of phthalic acid.

Such precipitant esters include dimethyl phthalate, diethyl phthalate and diisobutyl phthalate. Their reactive precipitant property is presumably based (an explanation not limiting the invention) on the poorer hydrocarbon affinity and solubility of the alkyl moiety of the replacing carboxylic acid ester with only 1 to 5 carbons in its alkyl, compared with the alkyl of 6 to 20 carbons of the original carboxylic acid ester.

The molar ratio between the second carboxylic acid ester and the complex, $R^4(COOR^5)_j/MgX^1_2.nR^1OH$, is preferably in the range 0.2/j–4/j and most preferably in the range 0.4/j–2/j. When the second carboxylic acid ester is a lower dialkyl phthalate (j=2), the ratio is thus in the range 0.1–2, preferably in the range 0.2–1. It is also preferable to apply the precipitant second carboxylic acid ester as a solution, e.g. in an aromatic hydrocarbon, with the concentration being preferably in the range 5–35% w/w and the aromatic hydrocarbon being preferably toluene.

Reactive precipitation is typically done by adding to the solution of the reaction product of the complex, titanium tetrahalide and the first carboxylic acid ester a precipitant, approximately 25% vol/vol solution of a lower dialkyl phthalate in toluene. In this case, the molar ratio between magnesium and the added lower dialkyl phthalate is in the order of approximately 2. Addition of the lower dialkyl phthalate precipitates the second composition. The solution to be decanted off usually consists of toluene, the reaction product, i.e. a higher dialkyl phthalate, such as diundecyl phthalate, detached from the dissolved composition, and titanium tetrachloride and titanium trichloride alkoxide. The precipitated solid second composition is usually washed e.g. with heptane and dried under a stream of nitrogen. Finally, the composition may be analysed, as required.

As mentioned above, nonreactive precipitation and reactive precipitation yield, respectively, a solid first composition and a solid second composition which can be subsequently recovered by filtration and/or decantation. Compositions in the solid state may be washed with a liquid such as a hydrocarbon, preferably many times.

As mentioned above, a composition in the liquid state, that is a composition with a carboxylic acid ester with an alkyl moiety comprising 6 to 20 alkyl groups, can be used as a liquid for the preparation of other products, such as catalysts. In an embodiment, it is precipitated using a hydrocarbon, such as an aliphatic hydrocarbon, in the above-presented way whereafter the first composition in the solid state is extracted using a solvent that enriches magnesium into the said product. Thus, the concentration of magnesium in the product can be increased by means of solvent extraction. In case a higher-magnesium composition, known as the third composition (i.e. not the same as the two previously mentioned compositions), is desired, it is advantageous to carry out the extraction with the magnesium-enriching solvent several times, preferably 2 to 10 times and most preferably 3 to 5 times.

If a composition according to the invention is a complex mixture or compound, extraction means that the magnesium halide, such as magnesium chloride, $MgCl_2$, remains in the mixture or compound, whereas other components, e.g. the titanium tetrahalide, such as titanium tetrachloride, $TiCl_4$, the (first) carboxylic acid ester, such as diundecyl phthalate (DUP), and the titanium trihalide alkoxide, such as titanium trichloroethoxide, dissolve in the enriching solvent and are removed from the reaction product. Aromatic hydrocarbons, such as toluene, have been found suitable for extraction purposes. Even chlorinated hydrocarbons, such as chloroform, carbon tetrachloride or trichloroethylene, are usable. Therefore, the invention also relates to a method whereby extraction is used to control the magnesium concentration of the above-mentioned first solid composition.

The extraction and washing can be combined so that the first composition precipitated with an aliphatic hydrocarbon is first washed a few times with an aliphatic hydrocarbon and then extracted, for instance, with an aromatic hydrocarbon, preferably several times, until the desired magnesium concentration is reached whereafter the third composition obtained may be rewashed, for instance, with an aliphatic hydrocarbon which will not enrich magnesium into the composition to the same extent.

The washing/extraction is typically done by recovering the nonreactively precipitated first composition either as such or after washing, for instance, three times with heptane and then going over to an extraction phase comprising 1 to 3 extractions, for instance, with toluene whereafter there are, for instance, 2 to 5 washes with heptane and finally 0 to 3 washes with pentane. The obtained magnesium-containing third composition is dried and analysed as required.

Below, compositions according to a particularly preferable embodiment of the invention and related particularly preferable precipitation, after-treatment and recovery methods will be presented. A liquid composition according to the invention is particularly preferably prepared a') by bringing the complex $MgCl_2.nR^6OH$, where $R^6$ is a $C_1$–$C_8$ alkyl and n is in the range 2.0–6.4, into contact with titanium tetrachloride, $TiCl_4$, at a molar ratio $TiCl_4/MgCl_2.nR^6OH$ that is in the range 20–60, with a di- $C_8$–$C_{14}$ alkyl ester of phthalic acid ($D^1$) at a molar ratio $D^1/Mg$ that is in the range of approximately 0.5–10, and preferably with toluene at a molar ratio $TiCl_4$/toluene that is in the range 1–6, and by heating the mixture to 80–120° C., to yield in dissolved form a composition of the said complex, titanium tetrachloride and a di- $C_7$–$C_{16}$ alkyl ester of phthalic acid.

According to the first variant of the particularly preferable embodiment, phase a') is followed by b') recovery of the said dissolved reaction product as the first solid composition by bringing it into contact with an essentially inert substance, preferably an aliphatic $C_5$–$C_{12}$ hydrocarbon, that precipitates it c') and separation of the first solid composition from the liquid and possibly washing of it.

According to the second variant of the particularly preferable embodiment, phase a') is followed by b") bringing of the said dissolved composition into contact with and making it to react with a di- $C_1$–$C_6$ alkyl ester of phthalic acid ($D^2$), such as dimethyl phthalate, diethyl phthalate or diisobutyl phthalate, at a molar ratio $D^2/MgCl_2.nR^6OH$ that is in the range 0.2–1, to yield in the liquid a second solid composition containing the said di- $C_1$–$C_6$ alkyl ester of phthalic acid ($D^2$), and c") separation of the said second solid composition from the liquid and preferably washing of it with a $C_5$–$C_{12}$ hydrocarbon.

According to the third variant of the particularly preferable embodiment, phase a') is followed first by phases b') and c'). Phase c') is followed by d') extraction of the said first solid composition at least once with a magnesium-enriching solvent, such as toluene, to yield a third solid composition with a magnesium concentration higher than that in the first solid composition, and possibly washing of the third solid composition.

There have been presented above various types of compositions according to the invention, of which the initial composition is a reaction product in the liquid state, preferably in dissolved form, that is usable as such in the liquid, preferably dissolved, state; the first solid composition according to the invention is obtained by nonreactively precipitating the said liquid or dissolved composition; the second solid composition is obtained by reactively precipitating the said liquid or dissolved composition; and the third solid composition is obtained by extracting the solid product of nonreactive precipitation (first solid composition) with a magnesium-enriching solvent.

It is generally appreciated in the field that the precise structure of complicated compositions such as Ziegler-Natta catalysts and their precursors is usually not known. Below, the proportions of complex-type of components in compositions according to the invention will be presented since it can be assumed that the complex $MgX^3{}_2 \cdot nR^7OH$ reacts with titanium tetrahalide, $TiX^4{}_4$, in such a way that the latter reacts quantitatively with the alcohol of the complex and forms titanium trihalide alkoxide, $TiX^4{}_3OR^7$, which is partly retained in the product, and, further, that the donor $D^3$, in this case a carboxylic acid ester, coordinates as such with the aforementioned other components and forms a liquid, preferably dissolved, product. We refer the reader to the experimental section of this publication. As it is, compositions according to the invention can also be expressed as proportions of the various molecular components, that is, as the complex composition.

We are, thus, dealing with a complex composition, since complexes refer to higher-order compounds composed of molecules, in distinction from first-order compounds composed of atoms. We refer the reader to Rompps Chemie-Lexicon, 7. Auflage, 1972, Teil 3, p. 1831. The formulas presented above and below refer either to a complex mixture, i.e. a mixture where the said molecules are present as such or in the form of various types of complexes, or to a complex compound, i.e. a substance where there are mainly a single type of stable complex molecules.

The invention, thus, refers to a composition containing magnesium, titanium, halogen and a composition, characterised in that it is soluble at least in liquid titanium tetrahalide, in a mixture of liquid titanium tetrahalide and a dissolvent organic substance $S^1$, or in a dissolvent organic substance $S^1$ and that it is a composition compatible with the following empirical formula (III):

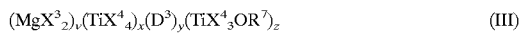

$$(MgX^3{}_2)_v (TiX^4{}_4)_x (D^3)_y (TiX^4{}_3OR^7)_z \qquad (III)$$

where $X^3$ is a halogen, $X^4$ is a halogen, $R^7$ is a $C_1$–$C_{20}$ alkyl, composition $D^3$ is a di- $C_6$–$C_{20}$ alkyl ester of phthalic acid, x+z is basically approximately 1, v is 1 to 8, x is 0 to 1, and y is 0.2 to 2.

A composition according to formula (III) is, as mentioned previously, soluble at least in liquid titanium tetrahalide, in a mixture of the latter and solvent $S^1$, or in plain solvent $S^1$. The liquid titanium tetrahalide is preferably titanium tetrachloride. The dissolvent organic substance $S^1$ is preferably an aromatic hydrocarbon, such as toluene. The said composition is preferably soluble at least in warm liquid titanium tetrahalide, in a mixture of liquid titanium tetrahalide and the dissolvent substance $S^1$, or in the dissolvent substance $S^1$, preferably at 60° C. to approximately 140° C., most preferably at 80–120° C.

The $X^3$ and/or $X^4$ according to formula (III) are/is preferably chlorines/chlorine. The composition is, thus, preferably based on magnesium chloride and titanium tetrachloride, as well as the reaction product of titanium tetrachloride and alcohol, the reaction product being titanium trichloride alkoxide.

The inner composition $D^3$, or a di- $C_6$–$C_{20}$ alkyl ester of phthalic acid, is preferably a di- $C_7$–$C_{16}$ alkyl ester of phthalic acid. It is important that there be enough carbon atoms in the alkyl moiety of the ester to make the composition soluble.

The alkyl $R^7$ of the titanium trihalide alkoxide is preferably a $C_1$–$C_8$ alkyl. Typical alkyls include methyl, ethyl, n-propyl, n-butyl and 2-ethyl-1-hexyl.

The makeup of empirical formula (III) is preferably such that, the total molar amount of titanium being 1, the molar amount, v, of magnesium halide, $MgX^3{}_2$, is 2 to 8, more preferably 3 to 8, the molar amount, x, of titanium halide, $TiX^4{}_4$, is 0.2 to approximately 1, more preferably 0.4 to approximately 1, the molar amount, y, of the inner electron donor $D^3$ is 0.6 to 1.4, more preferably 0.8 to 1.2, and the molar amount, z, of titanium trihalide alkoxide, $TiX^4{}_3OR^7$, is 0 to 0.8, preferably 0 to 0.6.

The composition according to empirical formula (III), containing magnesium, titanium, halogen and an electron donor, is preferably prepared by a method according to any of Patent Claims 12, 13 or 24. In the method, described in a previous section of this description, a complex of a magnesium halide and alcohol is reacted with a titanium tetrahalide and an inner electron donor under conditions where the reaction product obtained is in the liquid, preferably dissolved, state. The liquid, preferably dissolved, reaction product is then precipitated using a solvent that will not remain a part of the product.

In another embodiment of the invention, the composition containing magnesium, titanium, halogen and an electron donor is a composition compatible with the following empirical formula (IV):

$$(MgX^5{}_2)_{v'} (TiX^6{}_4)_{x'} (D^4)_{y'} (TiX^6{}_3OR^8)_{z'} \qquad (IV)$$

where $X^5$ is a halogen, $X^6$ is a halogen, $R^8$ is a $C_1$–$C_{20}$ alkyl, the inner electron donor $D^4$ is a di- $C_6$–$C_{20}$ alkyl ester of phthalic acid, x'+z' is basically approximately 1, v' is 9 to 16, x' is 0.2 to 1, and y' is 0.2 to approximately 1.

This composition differs from the composition according formula (III) essentially in having a substantially higher concentration of magnesium halide. A higher concentration of magnesium halide yields a higher activity when the composition is used for polymerisation of α-olefins. Thus, the invention also relates to the use of a composition, especially according to formula (IV), for homopolymerisation and copolymerisation of α-olefins, such as propene and ethene.

The halogens $X^5$ and $X^6$ in formula (IV) are, independently of each other, preferably chlorine atoms. The composition is preferably such that, the total molar amount, x'+z', of titanium being basically 1, the molar amount, v', of magnesium halide, $MgX^5{}_2$, is 7 to 14, the molar amount, x', of titanium halide, $TiX^6{}_4$, is 0.4 to 0.8, the molar amount, y', of the inner electron donor $D^4$ is approximately 0.8 to 1.2, and the molar amount, z', of titanium halide alkoxide, $TiX^6{}_3OR^8$, is 0.2 to 0.6. A particularly preferable composition is compatible with the approximate formula (V):

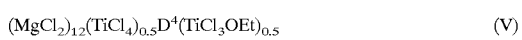

$$(MgCl_2)_{12} (TiCl_4)_{0.5} D^4 (TiCl_3OEt)_{0.5} \qquad (V)$$

where $D^4$ is the same as above.

The compositions according to formulas (IV) and (V) are preferably prepared by a method according to any of Patent Claims 20, 21, 22 or 25. Thus, they are prepared by reacting a complex of magnesium halide and alcohol, titanium tetrahalide and an inner electron donor under conditions conducive to dissolution of the product, precipitating the product and extracting the product with a magnesium-enriching solvent. The higher-magnesium composition obtained is not as soluble as the unextracted, lower-magnesium composition.

The invention also relates to a composition containing magnesium, titanium, halogen and an electron donor, compatible with the following empirical formula (VI):

$$(MgX^7_2)_{v''}(TiX^8_4)_{x''}(D^5)_{y''}(TiX^8_3OR^9)_{z''} \qquad (VI)$$

where $X^7$ is a halogen, $X^8$ is a halogen, $R^9$ is a $C_1$–$C_{20}$ alkyl, the inner electron donor $D^5$ is a di- $C_1$–$C_6$ alkyl ester of phthalic acid, x''+z'' is basically approximately 1.2, v'' is 1.5 to 10.5, x'' is 0.2 to 1.2, and y'' is 0.2 to 1.2.

This composition differs from compositions according to formulas (III) to (V) mainly in that the ester alkyl of the electron donor $D^5$ has only 1 to 6 carbon atoms, compared with the 5 to 20 carbon atoms in ester alkyls of the electron donors $D^3$ and $D^4$ of the compositions according to formulas (III) to (V). The second difference is that there is preferably less titanium trihalide alkoxide, $TiX^8_3OR^9$, in the composition according to formula (VI), i.e. z'' is smaller.

The halogens $X^7$ and $X^8$ in formula (VI) are preferably, albeit independently of each other, chlorine atoms. The inner electron donor $D^5$ is preferably a di- $C_1$–$C_4$ alkyl ester of phthalic acid. The total molar amount, x''+z'', of titanium being basically 1.2, the molar amount, v'', of magnesium halide, $MgX^7_2$, is preferably 1.6 to 2.4, the molar amount, x'', of titanium tetrahalide, $TiX^8_4$, is preferably 0.8 to 1,2, the molar amount, y'', of the electron donor $D^5$ is preferably 0.8 to 1.2, and the molar amount, z'', of titanium trichloride alkoxide is preferably 0 to 0.4. A complex composition compatible with formula (VII) is particularly preferable:

$$(MgCl_2)_2TiCl_4D^5 \qquad (VII)$$

A composition according to formulas (VI) and (VII) is preferably prepared by a method according to any of Patent Claims 14, 15, 16, 17 or 25, i.e. a method whereby the reaction product prepared in solution is reactively precipitated by adding an electron donor with 1 to 5 carbon atoms in its ester alkyl moiety.

The compositions according to the invention have been described above both with methods and formulas. The present invention also relates to the above-described methods for preparation of the compositions containing magnesium, titanium, halogen and an electron donor.

The above-described compositions are catalytically active in conjunction with polymerisation of α-olefins. The invention also relates to a method for polymerisation of α-olefins by bringing into contact with each other and reacting a procatalyst, which is a composition containing magnesium, titanium, halogen and an inner electron donor, a cocatalyst, which is an organometallic compound of a metal belonging to one of groups 1, 2 or 13 of the periodic system, preferably an external donor ED with at least one ligand atom capable of donating electrons, and one or more α-olefins. The polymerisation method according to the invention is characterised in that a composition according to any of Patent Claims 1 to 41, i.e. the above-described composition, is used as procatalyst. Typical α-olefins include ethene, propene, 1-butene, isobutene, 3-methyl-1-butene, 1-hexene, 4-methyl-1-pentene, 4,4-dimethyl-1-pentene, 1-octene and vinyl cyclohexane. Particularly preferable α-olefins for polymerisation include propene and a mixture of propene and another α-olefin, such as ethene. The polymerisation method, thus, relates to both homopolymerisation and copolymerisation.

As cocatalyst, there is usually used an organoaluminium compound, preferably a compound according to formula (VIII)

$$(R^{10}_mAlX^9_{3-m})_p \qquad (VIII)$$

where $R^{10}$ is a $C_1$–$C_{10}$ alkyl, $X^9$ is an atom or organic group containing a free electron pair, preferably a halogen such as chlorine, m is 2 or 3, and p is 1 or 2.

The molar ratio Al/Ti between the aluminium of the cocatalyst and the titanium of the said composition, or procatalyst, is preferably in the range 50–500 and most preferably in the range 200–350.

It is also preferable to use an external donor ED which may, in principle, be any external electron donor well recognised in the field. Silanes, which are organic silicon compounds, constitute one preferable group of donors since silanes often carry various substituents some of which are capable of donating electrons. The external donor ED is preferably a silane compound compatible with formula (IX)

$$R^{11}_qSi(OR^{12})_{4-q} \qquad (IX)$$

where group $R^{11}$ is one type or several types of $C_1$–$C_{20}$ alkyl or $C_6$–$C_{32}$ aryl, group $R^{12}$ is one type or several types of $C_1$–$C_{10}$ alkyl, and q is 1, 2 or 3.

The molar ratio, Al/ED, between the aluminium of the cocatalyst and the external electron donor ED is preferably in the range 5–20, most preferably in the range 6–15. The molar ratio, ED/Ti, between the external electron donor ED and the titanium of the said composition is preferably in the range 5–50, more preferably in the range 10–40 and most preferably in the range 20–30.

BRIEF DESCRIPTION OF THE DRAWINGS

FIG. 1 is a schematic presentation of a preparation of compositions of this invention.

FIG. 2 shows alcohol concentrations of compositions of the invention.

FIG. 3 shows proportions of titanium as a function of the molecular weight of the alcohols used in compositions of the invention.

FIGS. 4, 5, 6, and 7 present the titanium, maesium, chlorine, and DUP concentrations of compositions of the invention.

FIG. 8 depicts comparable molar proportions of certain components of compositions of the invention as functions of the molar mass of alcohol.

FIGS. 9 and 10 show the activities of compositions of this invention in bulk polymerization.

FIG. 11 shows the MFRs of homopolymers as functions of the chain length of the alcohols.

FIG. 12 shows the TSs of the polymers.

FIG. 13 presents the amounts of large particles of the polymer products.

FIG. 14 presents the amounts of fine particle fractions of the polymer products.

FIG. 15 presents the bulk densities of the homopolymers obtained.

FIGS. 16 and 17 present the activities of the catalytic compositions.

FIG. 18 shows the correlation between MFR value and ethene concentration in various E/P polymers.

FIG. 19 demonstrates that the type of alcohol starting material has little effect on the concentration of ethene.

FIG. 20 shows the melting points of the copolymers.

FIG. 21 shows the XSs of the copolymers obtained.

FIG. 22 shows the crystallinities of the copolymers.

FIG. 23 shows the peak widths of the DSC melting curves of the copolymers.

FIGS. 25A, 25B, and 25C provide details of synthetic pathways used to prepare compositions of this invention.

FIG. 26 presents the titanium concentrations of various compositions of the invention.

FIG. 27 presents the magnesium concentrations of various compositions of the invention.

FIG. 28 presents the chlorine concentrations of various compositions of the invention.

FIG. 29 presents the donor concentrations of various compositions of the invention.

FIGS. 30 and 31 show activities of catalyst complexes.

FIG. 32 presents the MFRs of the homopolymers.

FIG. 33 presents MFR as a function of catalyst complex activity.

FIG. 34 shows the total xylene-soluble proportions of the homopolymers in percent.

FIGS. 35 and 36 show activities of the compositions in gas-phase E/P copolymerization.

FIG. 37 shows the MFR values of the copolymers of propene and ethene.

FIG. 38 shows the MFR values of certain copolymers as functions of activity.

FIG. 39 present the SX values of the copolymers obtained.

FIG. 40 shows the ethene comonomer concentration of the copolymers.

FIG. 41 shows the melting points of the copolymers.

FIG. 42 shows the DSC crystallinities of the copolymers.

FIG. 43A shows the peak widths of the melting curves of the copolymers.

FIG. 43B shows activity of a catalyst complex as a function of the molar ratio Al/Ti.

FIG. 44 depicts melt flow rate of homopolymer as a function of amount of TEA.

FIG. 45 shows TS as a function of the molar ratio Al/Ti.

FIG. 46 depicts activity of a catalyst complex as a function of amount of TEA.

FIG. 47 shows MFR as a function of the molar ratio Al/Ti.

FIG. 48 shows TS values as functions of the molar ratio Al/Ti.

FIG. 49 depicts activity of a complex as a function of an external donor.

FIG. 50 depicts melt flow rate of a homopolymer as a function of amount of external donor.

FIG. 51 illustrates TS values of a homopolymer as a function of the molar ratio of a donor to titanium.

FIG. 52 depicts activity of a complex as a function of amount of external donor.

FIG. 53 shows that melt flow rate increases with increasing concentration of external donor.

FIG. 54 shows that TS value decreases with increasing concentration of external donor.

FIG. 55 depicts reduction in titanium molar-% as a function of increasing washing power.

FIG. 56 depicts reduction in DUP molar-% as a function of increasing washing power.

FIG. 57 shows the correlation between molar-% of titanium and molar-% of donor.

FIG. 58 depicts magnesium chloride concentration as a function of washing power.

FIG. 59 present molar ratios of various compositional components as functions of increasing washing power.

FIG. 60 shows activities of washed catalytic composition as functions of washing power.

FIG. 61 shows the MFRs of certain polymers as functions of washing power.

FIG. 62 shows Ts values as functions of washing power.

Figure 24:
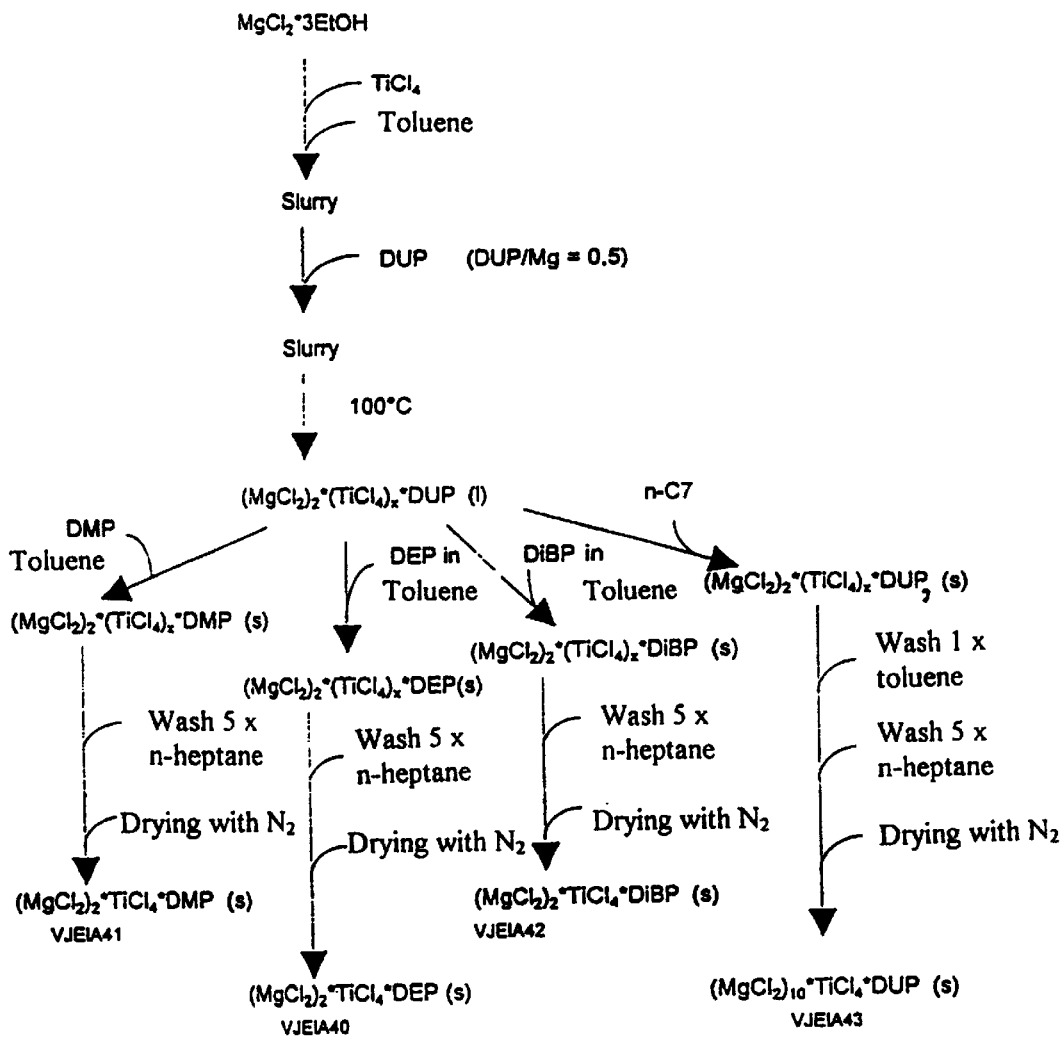
FIG. 24 is a schematic presentation of a preparation of compositions of this invention.

The invention will be illustrated with examples below.

EXAMPLES K1 TO K5, 1 TO 5, H1 TO H5 AND C1 TO C5

Examples will be presented below of the preparation of $MgCl_2 \cdot nROH$ carriers from various alcohols. The codes of the carriers are K1 to K5. These carriers are used to prepare the catalytic compositions 1 to 5. These compositions are used for homopolymerisation of propene, yielding homopolymers of propene (Examples H1 to H5), and finally for ethene/propene gas-phase copolymerisation, yielding E/P copolymers (Examples C1 to C5).

The preparation from various types of $MgCl_2 \cdot nROH$ complexes of a composition with the formula $(MgX2)_v (TiX_4)_x (D)_y (TiX_3OR)_z$ will be described. The alcohols, ROH, used in the preparation are methanol (MeOH), n-propanol (n-PrOH), n-butanol (n-BuOH) and 2-ethyl-1-hexanol (EHA). The compositions obtained are analysed and tested in bulk homopolymerisation of propene and in gas-phase copolymerisation of propene and ethene.

Experimental Section

The study was started by preparing various $MgCl_2 \cdot nROH$ complexes by the so-called emulsification method. These complexes were then made to react with titanium tetrachloride, $TiCl_4$, and diundecyl phthalate (DUP) to obtain a soluble reaction product. The reaction product was precipitated, washed and dried after which the solid product was characterised using chemical analysis. All precipitated reaction products were tested as catalysts by using them for bulk homopolymerisation of propene and for gas-phase copolymerisation with ethene. The polymers obtained were characterised using normal polymer analysis. Both the magnesium-alcohol complex and the soluble reaction product were prepared in completely inert conditions, using a nitrogen atmosphere.

Preparation of the $MgCl_2 \cdot nROH$ Complex

A 1 l volume of silicone oil (Dow Corning 200/100 CS) was introduced into a 5 l thermostated glass reactor. Then 100 g (1.01 mol) anhydrous magnesium chloride together with 2 g emulsifying agent (SPAN 65) was added. The mixer speed was 300 r/min, and a flash mixer was used to improve the mixing efficiency. Then the temperature was raised. As the temperature was being raised, the said alcohol was added in a dropwise manner. The temperature was raised until the added alcohol started to boil under reflux (70–130° C.). The said alcohol was added until its reaction product with the magnesium chloride, $MgCl_2$, melted. The flash mixer dispersed the melt into small droplets. The mixing was continued for 1.5 h to ensure even distribution of the melt droplets. Then 1.5 l heptane was added to another 5 l glass reactor. The heptane was cooled to −20° C. by means of a cooling bath. When the emulsified magnesium chloride-alcohol complex was in the form of melt droplets, the entire emulsion was siphoned into the said other glass reactor. The emulsion droplets solidified in the cold heptane, and the solid $MgCl_2 \cdot nROH$ complex could be recovered as an easily manageable powder. The complex was washed 4 times with heptane and once with pentane. Finally the complex substance was dried under a stream of nitrogen. The makeup of the complex was analysed by determining its concentrations of Mg, Cl and ROH.

Preparation of the $(MgCl_2)_x(TiCl_4)_x(DUP)_y(TiCl_3OR)_z$ Product

About 0.03 mol of the said $MgCl_2 \cdot nROH$ complex was added to a thermostated glass reactor. Then 50 ml (0.47 mol) toluene was added, followed by 100 ml (0.9 mol) titanium tetrachloride, $TiCl_4$. The molar ratio $TiCl_4$/toluene was 2:1. Finally the Lewis base DUP was added. The molar ratio DUP/Mg was 0.5, and the molar ratio Ti/Mg was 30. The temperature was raised to 100° C., and the reaction solution was held at this temperature to obtain a clear solution.

The temperature was then lowered to 80° C., and 140 ml heptane was added. The reaction product precipitated as a result of the addition of heptane. Here, the molar ratio $TiCl_4$/reaction product was 60. After the solution containing toluene, titanium tetrachloride and titanium trichloride alkoxide had been decanted off, the solid reaction product was washed once with 140 ml toluene and 3 times with 70 ml heptane and finally once with 100 ml pentane. The reaction product was dried under a stream of nitrogen. The product was analysed by determining its concentrations of Ti, Mg, Cl and DUP; additionally any concentrations of phthalic anhydride and dialkyl phthalate were analysed, the latter in respect of phthalates with alkyl moieties composed of the alkyls of the alcohols in the complex. The reaction product was also analysed for the concentration of the alcohol, ROH, in order to obtain the amount of titanium trichloride alkoxide ($TiCl_3OR$) since any measured alcohol was assumed to originate quantitatively from the titanium trichloride alkoxide of the solid reaction product. Details of the preparation of the composition according to the invention are compiled in Appendices 1 to 3 and in FIG. 1.

Bulk Polymerisation

Propene was polymerised in a tank reactor fitted with a mixer and having a volume of 5 l. Approximately 0.5 ml triethylaluminium cocatalyst (TEA), approximately 0.3 ml of a 25% vol/vol solution of cyclohexylmethyl dimethoxysilane in n-heptane (external donor ED), and 30 ml n-pentane were mixed together and allowed to react for 5 min. Half the mixture obtained was introduced into the polymerisation reactor, and half was mixed with 20 mg of the said composition. In the present context, the composition will be called the procatalyst or catalyst. After another 5 min, the catalyst/TEA/ED/n-heptane mixture was added to the reactor. The molar ratio Al/Ti was 250, and the molar ratio Al/ED was 10. A 70 mmol amount of hydrogen and 1400 g propene were added to the reactor, and the temperature was raised to the polymerisation temperature of +70° C. over 15–30 min. The polymerisation period was 60 min after which the polymer formed was removed from the reactor. The polymer was analysed for melt flow rate (MFR), bulk density (BD), total xylene-soluble mass (TS) and particle size distribution (PSD).

Copolymerisation of Propene and Ethene in Gas Phase

Propene was copolymerised with ethene in a tank reactor fitted with a mixer and having a volume of 2 l. An 80 g amount of dry sodium chloride, NaCl, was introduced into the polymerisation reactor to form the fluidised bed. Approximately 1.0 ml triisobutylaluminium cocatalyst (TIBA), approximately 0.4 ml of a 25% vol/vol solution of cyclohexylmethyl dimethoxysilane (CMMS) in n-heptane (external donor ED), and 30 ml n-pentane were mixed together and allowed to react for 5 min. Half the mixture obtained was added to the polymerisation reactor, immediately after which the pressure in the reactor was lowered to below 0.1 bar, thus allowing the added pentane to evaporate. The other half of the mixture was mixed with approximately 30 mg catalyst. After another 5 min the catalyst/TIBA/ED/n-pentane mixture was added to the reactor, and the added pentane was evaporated off by lowering the pressure in the reactor to 0.05 bar. The molar ratio Al/Ti was 200, and the molar ratio Al/ED was 10. A 4 mmol amount of hydrogen was fed into the reactor. A gaseous mixture of propene and ethene, containing 4.76% w/w ethene, was continuously fed into the reactor. The polymerisation period was 2 h, the pressure 7 bar and the temperature 70° C. The copolymers obtained were analysed for MFR, xylene-soluble mass (XS), total ethene concentration (Tot E % w/w), melting point (mp), width of DSC melting curve, and crystallinity.

Results

Composition of the $MgCl_2 \cdot nROH$ Complex

No difficulty was encountered in preparing the magnesium chloride-alcohol complexes that functioned as starting material. The compositions of the various $MgCl_2 \cdot nROH$ complexes are summarised in Table 1. It was easy to dry the materials except in the case of $MgCl_2 \cdot$n-BuOH where the product was sticky and thus retained some hydrocarbon. As seen in Table 1, the alcohol concentrations of the various materials ranged from a molar ratio $ROH/MgCl_2$ of 2.8 for ethanol, EtOH, to one of 6.1 for methanol, MeOH. $C_2$–$C_4$ alcohols have a systematic tendency to stronger binding to the complex but not all of the alcohols in the test series conform to this general trend.

TABLE 1

Results of analysis of the $MgCl_2 \cdot nROH$ complexes K1–K5 used in the synthesis. EHA = 2-ethylhexyl alcohol.

| Example | ROH | Mg % w/w | Cl % w/w | ROH % w/w | $ROH/MgCl_2$ mol/mol |
|---------|--------|------|------|------|------|
| K1 | MeOH | 8.3 | 24.7 | 66.4 | 6.1 |
| K2 | EtOH | 10.9 | 31.3 | 58.0 | 2.8 |
| K3 | n-PrOH | 6.5 | 18.6 | 68.0 | 4.2 |
| K4 | n-BuOH | 3.5 | 10.9 | 52.9 | 5.0 |
| K5 | EHA | 4.7 | 13.7 | 81.6 | 3.2 |

TABLE 2

Results of analysis of the catalytic composition

| Example | ROH | Ti % w/w | Mg % w/w | Cl % w/w | DUP % w/w | ROH % w/w | PA % w/w | DOP % w/w |
|---------|--------|-----|------|------|------|------|---|---|
| Exp. 1 | MeOH | 3.6 | 11.9 | 4.24 | 16.5 | 3.01 | 0 | 0 |
| Exp. 2 | EtOH | 3.2 | 12.7 | 44.3 | 31.7 | 1.71 | 0 | 0 |
| Exp. 3 | n-PrOH | 3.3 | 12.8 | 44.5 | 31.1 | 1.68 | 0 | 0 |

TABLE 2-continued

Results of analysis of the catalytic composition

| Example | ROH | Ti % w/w | Mg % w/w | Cl % w/w | DUP % w/w | ROH % w/w | PA % w/w | DOP % w/w |
|---|---|---|---|---|---|---|---|---|
| Exp. 4 | n-BuOH | 3.0 | 5.1 | 23.8 | 20.4 | 1.97 | 0 | 0 |
| Exp. 5 | EHA | 5.6 | 7.0 | 37.2 | 37.4 | 5.60 | 0.2 | 0.3 |

TABLE 3

Composition expressed in equivalents

| Example | Ti | Mg | Cl | DUP | ROH |
|---|---|---|---|---|---|
| Exp. 1 | 1 | 6.51 | 15.9 | 0.46 | 1.25 |
| Exp. 2 | 1 | 7.82 | 18.7 | 1.00 | 0.56 |
| Exp. 3 | 1 | 7.64 | 18.2 | 0.95 | 0.41 |
| Exp. 4 | 1 | 3.35 | 10.7 | 0.69 | 0.42 |
| Exp. 5 | 1 | 2.46 | 9.0 | 0.67 | 0.37 |

Titanium trichloride alkoxide concentration of the $(MgCl_2)_v(TiCl_4)_x(D)_y(TiCl_3OR)_z$ composition The final $(MgCl_2)_v(TiCl_4)_x(D)_y(TiCl_3OR)_z$ product was prepared as described in the experimental section. There were no problems. The reaction products produced were analysed, and the results are presented in Table 2. The equivalent molar proportions of all the components of the reaction product in relation to the molar amount of titanium are presented in Table 3.

The amount of titanium trichloride alkoxide, $TiCl_3OR$, in the composition obtained was measured by determining the alcohol concentration of the precipitated product. This is based on the assumption that the amount of alcohol detected in the analysis originates quantitatively from the said titanium trichloride alkoxide. On the other hand, it was interesting to see to what extent the different alcohols affected the amounts of the other components of the products.

The results presented in Table 3 indicate that the larger the allyl group of the alcohol, the less titanium trichloride alkoxide the final product contained in relation to titanium. Use of shorter-chain aliphatic alcohols yielded products with more titanium trichloride alkoxide in relation to titanium. In the product derived with the $MgCl_2.6MeOH$ complex, thus, practically all of the titanium was in the form of titanium trichloride alkoxide, $TiCl_3OMe$. When the $MgCl_3.3EtOH$ complex is used as starting material, approximately 50% of the titanium is in the form of titanium trichloride alkoxide; when higher alcohols are used in the starting material, approximately 30% of titanium in the final product is in the form of titanium trichloride alkoxide (see FIGS. 2 and 3).

FIGS. 4, 5, 6 and 7 present the titanium, magnesium, chlorine and DUP concentrations of the compositions obtained. No systematic trends were observed in these concentrations.

Molar Proportions in the $(MgCl_2)_v(TiCl_4)_x(DUP)_y(TiCl_3OR)_z$ Composition

The results in Table 2 indicate that all the compositions contain some alcohol, i.e. originally titanium trichloride alkoxide, upon analysis. Table 4 presents the molar proportions in the product, with the total amount of titanium being set at one mole. Table 4 also presents the amount of titanium tetrachloride in the composition, derived by subtracting the molar amount of titanium trichloride alkoxide from the total molar amount of titanium (1 mol).

TABLE 4

Molar proportions based on the total amount of titanium (= 1) in the catalytic composition

| Example | Alcohol | Ti | $MgCl_2$ | $TiCl_4$ | DUP | $TiCl_3OR$ |
|---|---|---|---|---|---|---|
| 1 | MeOH | 1 | 6.5 | 0 | 0.46 | 1.25 |
| 2 | EtOH | 1 | 7.82 | 0.46 | 1.00 | 0.56 |
| 3 | n-PrOH | 1 | 7.64 | 0.58 | 0.95 | 0.41 |
| 4 | n-BuOH | 1 | 3.35 | 0.58 | 0.69 | 0.42 |
| 5 | 2-Et-HexOH | 1 | 2.46 | 0.75 | 0.67 | 0.37 |

Comparison of the data in Table 4 shows that the amount of titanium in the form of titanium tetrachloride increases with the chain length of the alkyl of the alcohol used. In this respect, the molar ratio $TiCl_4$/total-Ti can be seen to increase from 0 to 0.75. At the same time, the amount of the inner donor DUP increases from 0.46 to 0.67; all alcohols do not follow this trend, however. FIG. 8 presents the relative titanium tetrachloride and DUP values of the composition as functions of the molar mass of the alcohol used. Extrapolation from the curves produces the complex $MgCl_2:TiCl_4:DUP$ which is theoretically obtainable with an alcohol having a molecular weight of approximately 270 g/mol and corresponding to the formula $C_{18}H_{37}OH$. The results indicate that the longer the alkyl chain of the alcohol, ROH, the smaller is the proportion of titanium in the form of $TiCl_3OR$ and the better can the $(MgCl_2)_2TiCl_4DUP$ complex be achieved.

Bulk Homopolymerisation of Propene

All the catalytic compositions were used for bulk polymerisation of propene as presented in the experimental section. The polymerisations came out well. The results of these polymerisations are presented in Tables 5 and 6.

TABLE 5

Bulk homopolymerisation of propene

| Example | ROH | Activity kg PP/g cat | Activity kg PP/g Ti | $MFR_2$ g/10 min | BD kg/m3 | TS % | >4 mm % w/w | <0.5 mm % w/w |
|---|---|---|---|---|---|---|---|---|
| H1 | MeOH | 8.1 | 225 | 13.4 | 390 | 6.2 | 11.1 | 16.9 |
| H2 | EtOH | 11.4 | 355 | 8.1 | 410 | 2.7 | 11.3 | 28.8 |
| H3 | n-PrOH | 15.7 | 477 | 6.5 | 440 | 3.2 | 31.4 | 11.9 |
| H4 | n-BuOH | 14.9 | 497 | 6.9 | 350 | 4.8 | 49.0 | 12.5 |
| H5 | EHA | 8.4 | 149 | 8.8 | 190 | 4.2 | 41.7 | 3.8 |

TABLE 6

Particle size distribution in polypropene

| ROH mm | MeOH % w/w | EtOH % w/w | n-PrOH % w/w | n-BuOH % w/w | EHA % w/w |
|---|---|---|---|---|---|
| 5.0 | 7.0 | 6.3 | 22.4 | 42.2 | 32.9 |
| 4.0 | 4.1 | 4.5 | 9.0 | 6.8 | 8.8 |
| 2.0 | 21.7 | 15.7 | 26.4 | 15.3 | 26.9 |
| 1.0 | 29.9 | 22.0 | 16.8 | 12.7 | 19.6 |
| 0.5 | 20.3 | 22.1 | 13.5 | 10.5 | 8.0 |
| 0.18 | 14.3 | 22.4 | 9.7 | 9.6 | 3.6 |
| 0.1 | 2.3 | 5.3 | 1.6 | 2.3 | 0.2 |
| 0.056 | 0.3 | 1.0 | 0.6 | 0.5 | 0 |
| 0.036 | 0 | 0.1 | 0 | 0.1 | 0 |
| PAN | 0 | 0 | 0 | 0 | 0 |

Activities of the Catalyst Complexes used for Bulk Polymerisation

FIG. 9 shows the activities of the catalyst complexes used for bulk polymerisation. The activities are expressed in kg PP/g cat in FIG. 9 and in kg PP/g Ti in Table 10. Both the figure and the table indicate that the highest activity is obtained when propanol, PrOH, or butanol, ButOH, is used as the alcohol in the starting material, $MgCl_2 \cdot nROH$. Use of these alcohols yielded activities as high as 16 kg PP/g cat.

MFRs of Homopolymers

FIG. 11 shows the MFRs of homopolymers as functions of the chain length of the alcohol. The values were in the range 6–14, i.e. 2 to 4 times higher than those normally achieved with heterogeneous catalysts.

TSs of Homopolymers

FIG. 12 shows the TSs of the polymers. No systematic trend can be discerned when going over from short-chain alcohols to long-chain ones.

Particle Size Distributions and Bulk Densities of Homopolymers

The particle size distributions of all the homopolymers are presented in Table 6, the amounts of large particles (d>4 mm) of the polymer products in FIG. 13 and the amounts of fine particle fractions (d<0.5 mm) in FIG. 14. The results indicate that the longer the chain of the alcohol used in the starting material, the larger the particles of the final product. FIG. 15 presents the bulk densities of the homopolymers obtained. A bulk density exceeding 0.4 was recorded only in two cases (EtOH and n-PrOH).

Results of Copolymerisation of Propene and Ethene (=E/P)

E/P copolymerisation was carried out as described in the experimental section. No difficulty was encountered in the copolymerisation. The results of the copolymerisations are presented in Table 7.

Activity of E/P Copolymerisation

The activities of the catalytic compositions are presented in kg PO/g cat in FIG. 16 and in kg PO/g Ti in FIG. 17, as functions of the alcoholic starting material. In both cases, the activity decreases with increasing chain length of the alcohol. Thus, an opposite trend appears to exist in E/P copolymerisations compared with homopolymerisations. The highest activities were obtained with catalytic compositions derived with methanol and ethanol, yielding activities of approximately 2 kg EP/g cat.

Incorporation of Ethene into E/P Copolymer

FIG. 18 shows the correlation between MFR value and ethene concentration in various E/P copolymers. FIG. 19 indicates that the type of alcoholic starting material has little effect on the concentration of ethene.

Results of Analysis of E/P Copolymers

FIG. 20 shows the melting points of the copolymers. FIG. 21 shows the XSs of the copolymers obtained, FIG. 22 shows the crystallinities of the copolymers, and FIG. 23 shows the peak widths of the DSC melting curves of the copolymers. Since MFR and ethene concentration are variable in these polymers, the results of analysis do not allow any systematic conclusions.

SUMMARY

In Examples 1 to 5, H1 to H5 and C1 to C5, we have prepared and analysed the composition $(MgCl_2)_v(TiCl_4)_x(DUP)_y(TiCl_3OR)_z$ and tested its catalytic polymerisation activity as a function of the chain length of the alcoholic starting material contained in the magnesium chloride-alcohol complex. The following observations were made:

1. All the compositions obtained contain some titanium trichloride alkoxide, $TiCl_3OR$, appearing as alcohol in the analysis (Table 2). The best way of expressing the composition according to the invention is the formula:

$$(MgCl_2)_v(TiCl_4)_x(DUP)_y(TiCl_3OR)_z$$

2. The longer the chain of the alcohol of the $MgCl_2 \cdot nROH$ complex is, the more titanium tetrachloride, $TiCl_4$, and diundecyl phthalate donor, DUP, the composition contains (FIG. 8).
3. The longer the chain of the alcohol of the $MgCl_2 \cdot nROH$ complex is, the higher is the activity of bulk homopolymerisation (FIGS. 9 and 10) (EHA being an exception).
4. The longer the chain of the alcohol of the $MgCl_2 \cdot nROH$ complex is, the lower is the activity of gas-phase copolymerisation (FIGS. 16 and 17).

EXAMPLES 6 TO 9, H6 TO H9 AND C6 TO C9

Preparation of the $(MgCl_2)_2(TiCl_4)D$ Complex and Related Complexes by Means of Donor Precipitation

TABLE 7

Gas-phase copolymerisation of propene and ethene

| Example | ROH | Activity kg PO/ g cat | Activity kg PO/ g Ti | MFR 2 g/10 min | XS % | Tot. E % w/w | mp °C. | DSC peak width °C. | Cryst. % |
|---|---|---|---|---|---|---|---|---|---|
| C1 | MeOH | 2.0 | 55 | 5.2 | 25.5 | 6.5 | 139.9 | 15.9 | 29.2 |
| C2 | EtOH | 2.0 | 63 | 4.7 | 20.3 | 6.0 | 135.0 | 22.1 | 30.1 |
| C3 | n-PrOH | 1.7 | 51 | 6.0 | 27.7 | 6.1 | 136.2 | 33.8 | 26.3 |
| C4 | n-BuOH | 1.1 | 38 | 8.4 | 23.4 | 5.8 | 130.4 | 38.4 | 25.4 |
| C5 | EHA | 0.7 | 12 | 2.9 | 24.0 | 7.0 | 137.6 | 31.5 | 23.3 |

Examples 1 to 5, H1 to H5 and C1 to C5 described the preparation of the soluble catalytic composition $(MgCl_2)_{v'}(TiCl_4)_{x'}(DUP)_{y'}(TiCl_3OR)_{z'}$ with use of various $MgCl_2 \cdot nROH$ complexes as starting materials. The following examples describe the preparation of catalytic compositions and complexes compatible with the empirical formula $$(MgX^a{}_2)_{v''}(TiX^b{}_4)_{x''}(D^2)_{y''}(TiX_3OR)_{z''} \qquad (VI)$$

where $X^a$ is a halogen, $X^b$ is a halogen, R is a $C_1$–$C_{20}$ alkyl, the inner electron donor $D^2$ is a di- $C_1$–$C_6$ alkyl ester of phthalic acid, x''+z'' is basically 1.2, v'' is 1.5 to 10.5, x'' is 0.2 to 1.2, and y'' is 0.2 to 1.2, using donor precipitation. First, a soluble composition in titanium tetrachloride-toluene solvent is prepared using diundecyl phthalate (DUP) as an inner electron donor. This soluble composition is then precipitated using a short-chain phthalate D which is dimethyl phthalate (DMP), diethyl phthalate (DEP) or diisobutyl phthalate (DEBP). The precipitated compositions are analysed and their catalytic powers tested in both bulk polymerisation of propene and gas-phase copolymerisation of propene and ethene.

Experimental Section

Preparation of the $(MgCl_2)_2TiCl_4D^2$ Complex

About 0.05 mol of $MgCl_2 \cdot 3EtOH$ complex prepared according to Example 2 above was introduced into a thermostated glass reactor. Then, 75 ml (0.70 mol) toluene was added, followed by 150 ml (1.37 mol) titanium tetrachloride, $TiCl_4$. The molar ratio $TiCl_4$/toluene was 2:1. Finally, the inner donor DUP was added. The molar ratio DUP/Mg was 0.5. The temperature was raised to 100° C., and the reaction mixture was kept at this temperature until a clear solution was obtained. The result was the composition $(MgCl_2)_{v'}(TiCl_4)_{x'}(DUP)_{y'}(TiCl_3OR)_{z'}$ in solution.

Then, 0.025 mol DMP, DEP or DIBP was added as a 25% vol/vol solution in toluene. The molar ratio, Mg/$D^2$, between magnesium and the donors added was 2.0. As a result of this addition, a product with the approximate formula $(MgCl_2)_2(TiCl_4)D^2$ was precipitated. In reality, the product contained some titanium trichloride alkoxide but its proportion was smaller than in the soluble composition into which the said donors were added for precipitation. The molar ratio $TiCl_4$/composition in the precipitate was 60. After the solution consisting of toluene, DUP, titanium tetrachloride and titanium trichloride alkoxide had been removed by decanting, the solid composition was washed 5 times with 200 ml heptane. The product was dried under a stream of nitrogen. It was analysed for titanium, magnesium, chlorine and donors, as well as for a potential hybrid product, ethylundecyl phthalate (EUP). The product was also analysed for ethanol concentration which was considered to originate quantitatively from the titanium trichloride ethoxide, $TiCl_3OEt$, of the composition. For comparison, the soluble composition was also precipitated with heptane as described in Examples 1 to 5. The details of the synthesis are presented in Diagram 1.

Bulk Polymerisation

Propene was polymerised a in a tank reactor fitted with a mixer and having a volume of 5 l. Approximately 0.9 ml triethylaluminium cocatalyst (TEA), approximately 0.5 ml of a 25% vol/vol solution of cyclohexylmethyl dimethoxysilane (CMMS) in n-heptane (external donor ED), and 30 ml n-heptane were mixed together and reacted for 5 min. Half the mixture was introduced into the polymerisation reactor, and half was mixed with approximately 25 mg of the aforementioned catalytic composition. After another 5 min, the catalytic mixture/TEA/ED/n-heptane mixture was added to the reactor. The molar ratio Al/Ti was 250, and the molar ratio Al/ED was 10. A 70 mmol amount of hydrogen and 1400 g propene were added to the reactor, and the temperature was raised to 70° C. over 15–30 min. The polymerisation period was 60 min after which the polymer formed was removed from the reactor. The polymers were analysed for melt flow rate ($MFR_2$), BD and TS.

Gas-phase Copolymerisation of Propene and Ethene

Propene was copolymerised with ethene in a tank reactor fitted with a mixer and having a volume of 2 l. An 80 g amount of dry sodium chloride, NaCl, was introduced into the polymerisation reactor to form the fluidised material. Approximately 1.7 ml triisobutylaluminium cocatalyst (TIBA), approximately 0.5 ml of a 25% vol/vol solution of cyclohexylmethyl dimethoxysilane (CMMS) in n-heptane (external donor ED), and 30 ml n-pentane were mixed together and allowed to react for 5 min. Half the mixture was added to the polymerisation reactor, immediately after which the pressure inside the reactor was lowered to below 0.1 bar by evaporating the added pentane. The other half of the mixture was mixed with approximately 30 mg of one of the aforementioned catalytic compositions. After another 5 min, the catalytic composition/TIBA/ED/n-pentane mixture was added to the reactor, and the added pentane was evaporated off to lower the pressure inside the reactor to 0.05 bar. The molar ratio Al/Ti was 200, and the molar ratio Al/ED was 10. A 4 mmol amount of hydrogen was added to the reactor. A gaseous mixture of propene and ethene, containing 4.76% w/w ethene, was continuously fed into the reactor. The polymerisation period was 2 h, the pressure 7 bar and the temperature 70° C. The copolymers formed were analysed for MFR, XS, Tot. E (% w/w), mp, peak width of DSC melting curve, and crystallinity.

Results

Preparation of Catalytic Compositions (Examples 6 to 9)

No difficulty was encountered in preparing the precipitated catalytic compositions. The chemical makeups of these compositions are presented in Table 8, and the equivalent amounts of the various components in relation to titanium are presented in Table 9.

TABLE 8

| | | Results of analysis of the catalytic compositions | | | | | | | | |
|---|---|---|---|---|---|---|---|---|---|---|
| Exp. | Precipitation donor | Ti % w/w | Mg % w/w | Cl % w/w | EtOH % w/w | DUP % w/w | DMP % w/w | DEP % w/w | DiBP % w/w | EUP % w/w |
| 6 | DMP | 7.0 | 7.5 | 39.9 | 0.31 | 9.7 | 30.3 | | | |
| 7 | DEP | 7.6 | 8.3 | 42.0 | 0.72 | 14.7 | | 26.0 | | 1.2 |

TABLE 8-continued

Results of analysis of the catalytic compositions

| Exp. | Precipitation donor | Ti % w/w | Mg % w/w | Cl % w/w | EtOH % w/w | DUP % w/w | DMP % w/w | DEP % w/w | DiBP % w/w | EUP % w/w |
|---|---|---|---|---|---|---|---|---|---|---|
| 8 | DiBP | 7.5 | 7.3 | 43.0 | 1.28 | 5.4 | | | 38.4 | |
| 9 | n-C7 | 2.9 | 14.8 | 50.7 | 1.14 | 23.9 | | | | |

TABLE 9

Equivalent composition of the product

| Exp. | Precipitation donor | Ti | Mg | Cl | EtOH | DUP | DMP | DEP | DiBP | EUP |
|---|---|---|---|---|---|---|---|---|---|---|
| 6 | DMP | 1 | 2.11 | 7.7 | 0.05 | 0.14 | 1.07 | | | |
| 7 | DEP | 1 | 2.15 | 7.5 | 0.10 | 0.20 | | 0.7 | | 0.02 |
| 8 | DiBP | 1 | 1.92 | 7.7 | 0.18 | 0.07 | | | 0.88 | |
| 9 | n-C7 | 1 | 10.06 | 23.6 | 0.41 | 0.83 | | | | |

The titanium and magnesium concentrations of the various compositions are presented in FIGS. 26 and 27, respectively. The chloride and donor concentrations of the various compositions are presented in FIGS. 28 and 29, respectively. All the results indicate that precipitation of the solution of catalytic composition with a donor containing a small number of carbon atoms in its ester alkyl moiety yields an insoluble composition with an almost constant molecular structure. This affords the conclusion that the composition consists of identical molecular groups, in order words, that we are dealing with a complex compound comprising two molecules of $MgCl_2$, one molecule of $TiCl_4$ and one molecule of donor; i.e. its composition is:

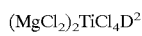

$$(MgCl_2)_2 TiCl_4 D^2$$

The above complex may contain small amounts of titanium trichloride alkoxide, $TiCl_3OR$. It is important to note that the same composition is obtained irrespective of what lower donor is used for the precipitation. DMP, DEP and DiBP all yield a more or less similar composition. The said donors, however, albeit precipitating the complex, did not completely displace the original longer-chain alkyl phthalate, DUP. Studies on reactive precipitation showed plausibly that a uniform chemical complex compound is produced. In contrast, nonreactive heptane precipitation according to Examples 1 to 5 produces a less definable composition. Thus, major parts of the titanium tetrachloride, $TiCl_4$, and the donor were extracted from the composition, and the $TiCl_3OR$ component constituted 41% of the total titanium present. In complexes produced in Examples 6 to 8, Mg/Ti was very close to 2:1 (Table 9).

Activity of Bulk Homopolymerisation of Propene (Examples H6 to H9)

All the catalyst complexes produced were tested in bulk polymerisation of propene, and the polymers were analysed for the properties presented in the experimental section. The results are presented in Table 10.

TABLE 10

Bulk homopolymerisation of propene

| Example | Precipitation donor | Activity kg PP/g cat | Activity kg PP/g Ti | MFR$_2$ g/10 mm | TS % |
|---|---|---|---|---|---|
| H6 | DMP | 3.2 | 46 | 15.3 | 4.5 |
| H7 | DEP | 3.9 | 51 | 15.0 | 3.7 |
| H8 | DiBP | 2.9 | 38 | 14.7 | 3.3 |
| H9 | n-C7 | 6.6 | 226 | 14.2 | 5.2 |

FIG. 30 presents the activities of the catalyst complexes in kg PP/g cat and FIG. 31 in kg PP/g Ti. The results showed that all stoichiometric complexes had approximately the same activity, i.e. approximately 3–4 kg PP/g cat. In contrast, complexes prepared using hydrocarbon precipitation exhibited activities ranging from 8 to 16 kg PP/g cat. No clear correlation between the activity of the catalyst and the magnesium concentration of the catalyst complex was observed.

MFRs of Homopolymers

FIG. 32 presents the MFRs of the homopolymers. Overall, the MFR values are high compared with those obtained with ordinary Ziegler-Natta catalysts. A slight reduction in MFR can be observed when going over from dimethyl ester of phthalic acid to diisobutyl ester of phthalic acid. FIG. 33 presents MFR as a function of catalyst complex activity. In this figure, the results for Examples H1 to H5 are included to provide a better picture of the correlation between activity and MFR. This reveals a clear correlation, i.e. the higher the activity, the lower the MFR and the lower the hydrogen sensitivity of the catalyst.

TSs of Homopolymers

FIG. 34 shows the total xylene-soluble proportions of the homopolymers in percent. The entire soluble proportion constitutes 3–4%, and it decreases slightly with increasing length of the ester alkyl moiety of the precipitation donor. These values are relatively good.

Activities of Gas-phase Copolymerisation of Propene and Ethene (Examples C6 to 9)

Table 11 presents all the results on gas-phase polymerisation of propene and ethene, as well as the properties of the copolymers obtained.

TABLE 11

Copolymerisation of propene and ethene in gas phase

| Example | Precipitation donor $D^2$ | Activity kg PO/g cat | Activity kg PO/g Ti | MFR$_2$ g/10 min | XS % | Tot. E % w/w | mp ° C. | DSC peak width ° C. | Cryst. % |
|---|---|---|---|---|---|---|---|---|---|
| C6 | DMP  | 0.5 | 7  | 3.0  | 21.9 | 7.8 | 135.1 | 43.9 | 26.8 |
| C7 | DEP  | 1.0 | 13 | 3.0  | 21.6 | 7.2 | 135.8 | 30.9 | 26.7 |
| C8 | DiBP | 0.3 | 4  | 0.4  | 27.5 | 8.6 | 124.3 | 32.0 | 20.1 |
| C9 | n-C7 | 0.6 | 22 | 14.5 | 36.2 | 7.4 | 137.8 | 30.3 | 21.6 |

FIG. 35 presents the activities in kg PO/g cat and FIG. 36 in kg PO/g Ti. According to the results, the activities range from 0.5 to 1.0 kg PO/g cat. There was no systematic trend between the activities and the precipitation donors used. Nor was there any systematic trend regarding activity when the results of homopolymerisation and those of copolymerisation were compared.

MFRs of Copolymers of Propene and Ethene

FIG. 37 shows the MFR values of the copolymers of propene and ethene. The MFR values were low for all three donor-precipitated catalyst complexes. FIG. 38 shows the MFR values of both $C_1$–$C_5$ donor-derived and $C_6$–$C_9$ donor-derived copolymers as functions of activity. The general trend with heptane-precipitated $C_6$–$C_9$ compositions is a decrease in hydrogen sensitivity and MFR value with increasing activity. The donor-precipitated compositions deviate from this trend, yielding low MFR values even at low activities.

XS Values of Copolymers of Propene and Ethene

FIG. 39 presents the XS values of the copolymers obtained. The values are in the range 20–30%, and the values tend to increase with the use of higher alkyl phthalates for precipitation. This indicates a decreasing ability of the catalyst complexes to achieve a random distribution of comonomers in the copolymer. On the other hand, in the case of copolymers of propene and ethene only those copolymers having the same MFR value and the same ethene concentration can be compared with each other. It should be noted, therefore, that on the basis of the same ethene concentrations only Examples C6 (DMP precipitation), C7 (DEP precipitation) and C9 (n-C7 precipitation) are comparable.

Ethene Concentrations of Copolymers

FIG. 40 shows the ethene comonomer concentrations of the copolymers. The comonomer concentrations are high, considering that the input monomer gas only contains 4.76% w/w ethene. The ethene concentrations tend to be twice those expected.

Properties of Copolymers

FIG. 41 shows the melting points of the copolymers. A slight correlation exists between the melting points and the ethene concentrations of the copolymers. The melting points range from 125° C. to 135° C. FIG. 42 shows the DSC crystallinities and FIG. 43 the peak widths of the melting curves of the copolymers.

Abstract

Examples 6 to 9, H6 to H9 and C6 to C9 have investigated the possibility of precipitating a soluble composition according to Examples 1 to 5 by replacing the donor of the soluble composition. Thus, the diundecyl phthalate donor (DUP) was replaced with phthalate esters having smaller alkyl moieties. Thus, dimethyl phthalate, diethyl phthalate and diisobutyl phthalate were used for precipitation. The study allows the following conclusions to be made:

1. The reactively precipitated complex is stoichiometric, and its composition is $(MgCl_2)_2TiCl_4D^2$ where $D^2$ is a dialkyl phthalate with a short alkyl chain.
2. All $(MgCl_2)_2TiCl_4D^2$ complexes were catalytically active in homopolymerisation of propene.
3. The MFRs of all homopolymers derived with $(MgCl_2)_2TiCl_4D^2$ complexes were high, ranging from 14 to 15.
4. $(MgCl_2)_2TiCl_4D^2$ complexes were catalytically active in gas-phase copolymerisations of propene and ethene.
5. There is a negative correlation between activity and MFR in both homopolymerisation and copolymerisation. This suggests that propene polymerisation and hydrogen termination are competitive reactions in homopolymerisation.
6. When $(MgCl_2)_2TiCl_4D^2$ complexes were used for ethene/propene copolymerisation, the incorporation of ethene into the polymer chain was as high as 7–8% although the ethene concentration of the input gas mixture was only 4.76%.
7. Ethene polymerisation and hydrogen termination are competitive reactions in copolymerisation of propene and ethene.
8. The equilibrium of the product $TiCl_3OR/D^2$ depends on the size of the precipitation donor $D^2$, with a larger donor $D^2$ producing a higher share of $TiCl_3OR$ in the composition.

EXAMPLES H10 TO H22

These examples investigated the conditions of propene homopolymerisation.

Experimental Section

Preparation of the $(MgCl_2)_2TiCl_4DEP$ Complex

The above complex was prepared according to Example 7 presented above.

Bulk Homopolymerisation of Propene

Propene was polymerised in a tank reactor fitted with a mixer and having a volume of 5 l. A suitable amount of triethylaluminium cocatalyst (TEA), a suitable amount of a 25% vol/vol solution of cyclohexyl dimethoxysilane (CMMS) in n-heptane (external donor ED), and 30 ml of n-pentane were mixed together, and the mixture was allowed to react for 5 min. Half the mixture was introduced into the polymerisation reactor, and half was mixed with 20 mg of the said $(MgCl_2)_2TiCl_4DEP$ complex. After another 5 min, the complex/TEA/ED/n-pentane mixture was added to the reactor. A 70 mmol amount of hydrogen and 1400 g propene were added to the reactor, and the temperature was raised to 70° C. over 15–30 min. The polymerisation period was 60 min after which the polymer formed was removed from the reactor. The polymers were analysed for MFR$_2$, BD and TS.

Four Series of Experiments

Four series of experiments were carried out to determine the polymerisation behaviour of the $(MgCl_2)_2TiCl_4DEP$ catalyst complex. The external donor CMMS will be referred to by the symbol ED below. In the first series, the molar ratio ED/Ti was kept constant at approximately 9 and the molar ratio Al/Ti was gradually altered from the value of 25 to approximately 250. In the second series of experiments, the molar ratio ED/Ti was kept constant at approximately 25 and the molar ratio Al/Ti was gradually altered from the value of 75 to 250. In the third series of experiments, the molar ratio Al/Ti was kept constant at approximately 70 and the molar ratio ED/Ti was gradually altered from the value of 0 to 25. In the fourth series of experiments, Al/Ti was kept constant at approximately 250 and the molar ratio ED/Ti was gradually altered from the value of 10 to approximately 25.

The values of the molar ratios ED/Ti and Al/Ti are presented in detail in Tables 12 to 15.

Results

First Series of Experiments (Examples H10 to H13)

Table 12 presents the results of the first series of experiments where the molar ratio ED/Ti was kept constant at approximately 9 and the molar ratio Al/Ti was gradually altered from a value of approximately 25 to approximately 250.

lation between activity and said molar ratio whereby the activity increases with increasing molar ratio as the aluminium compound reduces $Ti^{4+}$ to $Ti^{3+}$ and removes unnecessary donor from the vicinity of active titanium sites. The highest activity was approximately 4.5 kg PP/g cat.

Hydrogen Sensitivity

Theoretically, the highest amounts of an aluminium compound in relation to the amount of titanium should liberate donor and thus expose active sites whereby greater amounts of hydrogen should have a chance to break the chain. This would cause an increase in MFR. FIG. 44 unexpectedly shows that the opposite happened in the series of experiments, with MFR decreasing from 16 to 8 at the higher molar ratios of Al/Ti.

Effect of Molar Ratio Al/Ti on TS

FIG. 45 shows TS as a function of the molar ratio Al/Ti. In this series of experiments, the values of TS increase from approximately 4 to approximately 6.

Second Series of Experiments (Examples H14 to H16)

In the second series of experiments, the molar ratio ED/Ti was kept at approximately 25 and the molar ratio Al/Ti was

TABLE 12

Effect of amount of triethylaluminium (TEA) cocatalyst on propene homopolymerisation using the $(MgCl_2)_2TiCl_4DEP$ procatalyst at a constant molar ratio ED/Ti of 8–10

| Exp. | $D_2$/Ti mol/mol | Al/Ti mol/mol | Al/ED mol/mol | Activity kg PP/g cat | Activity kg PP/g Ti | $MFR_2$ g/10 min | BD kg/m³ | TS % w/w |
|---|---|---|---|---|---|---|---|---|
| H10 | 8.3 | 25 | 3 | 0.2 | 3 | | | 4.1 |
| H11 | 7.6 | 68 | 9 | 2.2 | 29 | 16.3 | | 4.6 |
| H12 | 10 | 150 | 15 | 3.7 | 49 | 15.4 | | 5.1 |
| H13 | 10 | 249 | 25 | 4.5 | 59 | 8 | 370 | 5.8 |

Activity

FIG. 43b shows the activity of the catalyst complex as a function of the molar ratio Al/Ti. There is a distinct correincreased from approximately 75 to approximately 250. The results of this series of experiments are presented in Table 13.

TABLE 13

Effect of molar ratio Al/Ti on propene polymerisation using the $(MgCl_2)_2TiCl_4DEP$ procatalyst at a constant molar ratio ED/Ti of approximately 25

| Exp. | ED/Ti mol/mol | Al/Ti mol/mol | Al/ED mol/mol | Activity kg PP/g cat | Activity kg PP/g Ti | $MFR_2$ g/10 min | BD kg/m³ | TS % w/w |
|---|---|---|---|---|---|---|---|---|
| H14 | 25.3 | 76 | 3 | 1.6 | 21 | 13.5 | | 2.8 |
| H15 | 25.0 | 150 | 6 | 3.8 | 50 | 13.1 | 400 | 3.6 |
| H16 | 24.9 | 249 | 10 | 3.9 | 51 | 15 | | 3.7 |

Activity

As in the first series of experiments, activity increases with an increasing molar ratio Al/Ti although the increase in activity levels off at the highest molar ratios. The highest activity obtained was 4.0 kg PP/g cat at the highest molar ratio Al/Ti, 250 (see FIG. 46).

Hydrogen Sensitivity

FIG. 47 shows MFR as a function of the molar ratio Al/Ti. In this series of experiments, a slight increase in MFR was observed. All MFR values were high, indicating good hydrogen sensitivity in all polymerisations.

TS as a Function of Molar Ratio Al/Ti

FIG. 48 shows TS values as functions of the molar ratio Al/Ti. These results, too, indicate that TS values clearly increase as the said molar ratio increases. Lower molar ratios Al/Ti yield TS values less than 3, whereas TS values of approximately 4 are obtained at higher molar ratios Al/Ti.

Third Series of Experiments (Examples H17 to H19)

Change in the Molar Ratio ED/Ti at a Constant Molar Ratio Al/Ti

As presented in the experimental section, two additional series of experiments were carried out where the amount of external donor was allowed to change while the molar ratio Al/Ti remained constant. In the third series of experiments, the molar ratio Al/Ti was kept constant at approximately 70 and the molar ratio $D_2/Ti$ was allowed to change from 0 to 25. The results of this series of experiments are presented in Table 14.

Hydrogen Sensitivity

According to FIG. 50, MFR values decrease when the amount of donor is increased. Further, this catalytic system yields MFR values close to 70 when no external donor is used. After decreasing, MFR stabilises at around 15 when only small amounts of external donor are yet present.

Effect of Donor on TS

The TS value continuously decreased when the amount of external donor was increased. This is apparent in FIG. 51. The figure shows a steep fall in TS values, from 21% to 3–4%. These results, too, indicate the dependence of the catalytic system on the external donor.

Fourth Series of Experiments (Examples H20–H22)

Change in the Molar Ratio ED/Ti at Higher Concentrations of Cocatalyst

In this fourth series of experiments, the molar ratio $D_2/Ti$ was altered from 10 to 25 while the molar ratio Al/Ti was kept constant at approximately 250. The results are presented in Table 15.

TABLE 14

Effect of amount of external donor CMMS (ED) on propene homopolymerisation using the $(MgCl_2)_2TiCl_4DEP$ procatalyst at a constant amount of TEA cocatalyst, i.e. at a molar ratio Al/Ti of 68–76

| Exp. | ED/Ti mol/mol | Al/Ti mol/mol | Al/ED mol/mol | Activity kg PP/g cat | Activity kg PP/g Ti | $MFR_2$ g/10 min | BD kg/m3 | TS % w/w |
|---|---|---|---|---|---|---|---|---|
| H17 | 0 | 70 | infinite | 3.0 | 40 | 69.0 | | 21.6 |
| H18 | 7.6 | 68 | 9 | 2.2 | 29 | 16.3 | | 4.6 |
| H19 | 25.3 | 76 | 3 | 1.6 | 21 | 13.5 | | 2.8 |

TABLE 15

Effect of amount of external donor CMMS (ED) on propene homopolymerisation using the $(MgCl_2)_2TlCl_4DEP$ procatalyst at a constant amount of TEA cocatalyst, i.e. at a molar ratio Al/Ti of 250

| Exp. | ED/Ti mol/mol | Al/Ti mol/mol | Al/ED mol/mol | Activity kg PP/g cat | Activity kg PP/g Ti | $MFR_2$ g/10 min | BD kg/m3 | TS % w/w |
|---|---|---|---|---|---|---|---|---|
| H20 | 10 | 249 | 25 | 4.5 | 59 | 8.0 | 370 | 5.8 |
| H21 | 15.5 | 248 | 16 | 4.4 | 58 | 6.6 | 350 | 4.8 |
| H22 | 24.9 | 249 | 10 | 3.9 | 5.1 | 15.0 | | 3.7 |

Activity

According to common experience, the activity of polymerisation should decrease when the amount of external donor in the polymerisation is increased. The results are presented in FIG. 49. The activity clearly tends to decrease with an increase in donor. Approximately 50% of activity is lost by increasing the molar ratio ED/Ti from 0 to 25.

Activity

A distinct reduction in activity was observed in this series of experiments. This is apparent in FIG. 52 although the decreasing effect of the external donor was largely offset by the large excess amount of cocatalyst. Owing to the higher concentration of cocatalyst, the activity always remained above the level of approximately 4 kg PP/g cat.

MFR

The melt flow rate increased with increasing concentration of external donor. The results are presented in FIG. 53. MFR values increased from the level of 7–8 to the level of 15 when changing over from a low to a high concentration of external donor. These values correspond to those of the first series of experiments.

TS as a Function of the Concentration of External Donor ED

The TS value continuously decreased as the concentration of the external donor increased. This is shown in FIG. 54. The reduction in TS value is almost linear when going over from a molar ratio ED/Ti of 10 to a molar ratio of 25, with TS decreasing from 5.8 to 3.7.

Summary

Examples 10 to 22 investigated the behaviour of the complex $(MgCl_2)_2TiCl_4DEP$ in bulk polymerisation of propene. The study which encompassed four series of experiments showed that:

1. Activity increases with increasing molar ratio Al/Ti.
2. Activity decreases with increasing molar ratio ED/Ti.
3. TS increases with increasing molar ratio Al/Ti.
4. TS decreases with increasing molar ratio ED/Ti.
5. MFR increases with increasing molar ratio Al/Ti.
6. MFR decreases with increasing molar ratio ED/Ti.

EXAMPLES 23 TO 28

Washing of the $(MgCl_2)_x(TiCl_4)_x(DUP)_y(TiCl_3OEt)_z$ Composition with Toluene and the Effect of this on the Catalytic Behaviour of the Composition In Examples 1 to 5 above, we have described the preparation of the title composition. Examples 23 to 28 indicate that part of the ligands $TiCl_4$, DUP and $TiCl_3OEt$ of the title composition can be removed by extraction using a suitable solvent. It was also found that extraction using ordinary aliphatic hydrocarbons was not particularly effective. An aromatic hydrocarbon, such as toluene, was used to find out how the catalytic polymerisation activity of the composition could be improved by making the extraction process more effective.

Experimental Section

Preparation of the $(MgCl_2)_x(TiCl_4)_x(DUP)_y(TiCl_3OEt)_z$ Composition

This series comprised six experiments. The starting composition, i.e. the title composition, was individually prepared for each experiment. The proportions of the chemicals and the phases of the synthesis were the same in all examples, but the absolute chemical amount may have varied.

Approximately 0.05 mol of $MgCl_2.3EtOH$ complex was introduced into a thermostated glass reactor. This complex had been prepared by a method according to Example 2. Approximately 75 ml (0.70 mol) toluene was added to facilitate the dissolution of the final product. Then 200 ml (1.82 mol) titanium tetrachloride, $TiCl_4$, was added. The molar ratio $TiCl_4$/toluene was 2:1, and the molar ratio Ti/Mg was approximately 35. Finally, the inner donor DUP was added. The molar ratio DUP/Mg was 0.5. The temperature was raised to 100° C., and the reaction mixture was held at this temperature until a clear solution formed. The clear solution was allowed to cool to 80° C., and approximately 400 ml heptane was added to the solution. After a short while, a product identified as $(MgCl_2)_x(TiCl_4)_x(DUP)_y(TiCl_3OEt)_z$ was precipitated; see Example 2. The solution containing toluene, free titanium tetrachloride, $TiCl_4$, and free titanium trichloride ethoxide, $TiCl_3OEt$, was removed by decanting, after which the solid product obtained could be washed and possibly dried. Details of the experimental conditions are presented in Table 16.

TABLE 16

Amounts of chemicals used in preparation of the catalytic composition

| Exp. | Mg cpd(* g | Mg cpd(* mol | Tol u-ene ml | Tol u-ene mol | TiCl4 ml | TiCl4 mol | DUP ml | DUP mol | Hep-tane ml | Hep-tane mol | TiCl4 ml | TiCl4 mol | Hep-tane ml | Hep-tane mol |
|---|---|---|---|---|---|---|---|---|---|---|---|---|---|---|
| 23 | 20.0 | 0.080 | 50 | 0.47 | 200 | 1.82 | 20.0 | 0.040 | 500 | 3.40 | 200 | 1.82 | 380 | 2.6 |
| 24 | 11.7 | 0.050 | 100 | 0.94 | 200 | 1.82 | 12.5 | 0.025 | 440 | 3.00 | 330 | 3.0 | 400 | 2.7 |
| 25 | 8.3 | 0.036 | 50 | 0.47 | 100 | 0.91 | 9.28 | 0.019 | 140 | 0.96 | | | | |
| 26 | 50.0 | 0.214 | 50 | 0.47 | 600 | 5.46 | 52.3 | 0.105 | 150 | 1.02 | | | | |
| 27 | 11.7 | 0.050 | 100 | 0.94 | 200 | 1.82 | 12.5 | 0.025 | 400 | 2.70 | | | | |
| 28 | 11.7 | 0.050 | 100 | 0.94 | 200 | 1.82 | 12.5 | 0.025 | 440 | 3.00 | 330 | 3.0 | 400 | 2.7 |

(*cpd = $MgCl_2.3EtOH$)

Washing of the $(MgCl_2)_x(TiCl_4)_x(DUP)_y(TiCl_3OEt)_z$ Composition

In this series of experiments, the catalytic composition was washed using increasing washing power. Thus, the first experiment involved a lower aliphatic hydrocarbon; then washing with a higher aliphatic hydrocarbon was employed; then the above stages were complemented with a stage using an aromatic hydrocarbon; then the stage with the lowest aliphatic hydrocarbon was replaced with an additional wash with a higher aliphatic hydrocarbon; then the number of washes with an aromatic hydrocarbon were increased; finally a stage with a higher aliphatic hydrocarbon was added at the end, and one more wash with an aromatic hydrocarbon was inserted. These washing stages are presented in Table 17.

TABLE 17

Washing stages associated with the synthesis of the catalytic composition in the series of experiments

| Example | Heptane wash | Toluene wash | Heptane wash | Pentane wash |
|---|---|---|---|---|
| 23 | | | | 3 × 300 ml |
| 24 | | | 3 × 400 ml | |
| 25 | | 1 × 140 ml | 4 × 140 ml | 1 × 30 ml |
| 26 | | 1 × 150 ml | 5 × 200 ml | |

TABLE 17-continued

Washing stages associated with the synthesis of the catalytic composition in the series of experiments

| Example | Heptane wash | Toluene wash | Heptane wash | Pentane wash |
|---|---|---|---|---|
| 27 | | 2 × 100 ml | | 1 × 100 ml |
| 28 | 3 × 400 ml | 3 × 140 ml | 2 × 60 ml | |

In the last example, the catalytic composition was washed 5 times with heptane and 3 times with toluene. In this context, washing generally refers to hydrocarbon treatment to remove original molecular components from the title composition. It may involve the removal of molecules present as impurities, molecules bound in complexes, or both. After the final washing solution had been filtered off, the solid product obtained was dried under a stream of nitrogen. The solid product was analysed for titanium, Ti, magnesium, Mg, chlorine, Cl, and the donor DUP. The product was also analysed for ethanol concentration since ethanol was considered in the analysis to be quantitatively derived from the titanium trichloride ethoxide, $TiCl_3 \cdot OEt$, originally contained in the product.

Bulk Homopolymerisation of Propene

Propene was polymerised in a tank reactor fitted with a mixer and having a volume of 5 l. Approximately 0.9 ml triethylaluminium cocatalyst (TEA), approximately 0.5 ml of a 25% vol/vol solution of cyclohexyl dimethoxysilane (CMMS, external donor (ED)) in n-heptane, and 30 ml n-pentane were mixed and reacted for 5 min. Half the mixture obtained was introduced into the polymerisation reactor, and half was mixed with 200 mg of the said catalytic composition. After another 5 min, the catalytic composition/TEA/ED/n-heptane mixture was added to the reactor. The molar ratio Al/Ti was 250, and the molar ratio Al/ED was 10. A 70 mmol amount of hydrogen and 1400 g propene were added to the reactor, and the temperature was raised to 70° C. over 15–30 min. The polymerisation period was 60 min after which the polymer formed was removed from the reactor. The polymer was analysed for $MFR_2$ and TS.

Results

Preparation of the $(MgCl_2)_v(TiCl_4)_x(DUP)_y(TiCl_3OEt)_z$ Composition

The title composition was prepared without difficulty as explained in the experimental section. It was also found that only a small amount of toluene was needed to obtain a completely clear solution. The molar ratio toluene/Mg was above 10 in most examples, but in Example 26 a molar ratio of only 2.1 was used and still a clear solution was obtained without difficulty. When toluene was completely abandoned, the solution of the reaction product did not clear up completely but remained slightly turbid.

The results of the synthesis also indicate that only a small amount of heptane is needed to transform the product to the solid state. Mostly a molar ratio $TiCl_4$/heptane of 2:3 was used, but Example 26 shows that an amount of heptane as small as that corresponding to a $TiCl_4$/heptane ratio of 5:1 functions equally well in precipitation of the catalytic composition.

Redissolution and reprecipitation of the solid composition did not change the proportions of its components. Redissolution and reprecipitation were carried out in Examples 23, 24 and 28.

Washing of the $(MgCl_2)_v(TiCl_4)_x(DUP)_y(TiCl_3OEt)_z$ composition

The washes were done as explained in the experimental section, and they are presented in Table 17. The washing posed no difficulty. The washing power of toluene was assumed to be better than that of aliphatic hydrocarbons since this is already apparent during the preparation of the composition where toluene is added to improve solubility and heptane is added to achieve precipitation. Finally, longer aliphatic hydrocarbons were assumed to be more effective than lower aliphatic hydrocarbons as extraction liquids, which means that heptane was a better extraction agent than pentane.

Results of Analysis of the Washed Compositions

The washed solid compositions were analysed for titanium, magnesium, DUP and EtOH concentrations. The results of analysis are presented in weight units in Table 18. Table 19 presents the corresponding molar concentrations of the compositions. Table 20 presents the same molar proportions in relation to a titanium concentration of 1. In Table 21, the molar proportion of titanium has been calculated on the basis of a molar proportion of magnesium of 2; finally, Table 22 presents the molar ratios Ti/Mg, DUP/Mg and EtOH/Mg.

TABLE 18

Chemical makeup of the catalytic composition

| Example | Ti % w/w | Mg % w/w | EtOH % w/w | DEP % w/w | DUP % w/w |
|---|---|---|---|---|---|
| 23 | 7.9 | 4.7 | 1.14 | 2.7 | 37.1 |
| 24 | 4.3 | 12.0 | | | 34.0 |
| 25 | 3.2 | 12.7 | 1.71 | | 31.7 |
| 26 | 2.9 | 14.8 | 1.14 | | 23.9 |
| 27 | 2.3 | 14.0 | | | |
| 28 | 2.1 | 13.2 | | | 23.0 |

TABLE 19

Stoichiometric proportions of the components of the catalytic composition

| Example | Ti | Mg | EtOH | DEP | DUP |
|---|---|---|---|---|---|
| 23 | 0.165 | 0.193 | 0.025 | 0.012 | 0.078 |
| 24 | 0.090 | 0.494 | ? | | 0.072 |
| 25 | 0.066 | 0.523 | 0.037 | | 0.067 |
| 26 | 0.061 | 0.609 | 0.025 | | 0.050 |
| 27 | 0.048 | 0.576 | ? | | |
| 28 | 0.044 | 0.543 | ? | | 0.048 |

TABLE 20

Proportions of the components with titanium as reference

| Example | Ti | Mg | EtOH | DEP | DUP |
|---|---|---|---|---|---|
| 23 | 1 | 1.17 | 0.15 | 0.07 | 0.47 |
| 24 | 1 | 5.50 | ? | | 0.80 |
| 25 | 1 | 7.82 | 0.56 | | 1.00 |
| 26 | 1 | 10.06 | 0.41 | | 0.83 |
| 27 | 1 | 12.00 | ? | | |
| 28 | 1 | 12.39 | ? | | 1.11 |

TABLE 21

Molar relations of titanium and magnesium with the molar amount of magnesium set at 2

| Example | Mg mol | Ti mol |
|---|---|---|
| 23 | 2 | 1.71 |
| 24 | 2 | 0.36 |
| 25 | 2 | 0.26 |
| 26 | 2 | 0.20 |
| 27 | 2 | 0.17 |
| 28 | 2 | 0.16 |

TABLE 22

Molar ratios Ti/Mg, DUP/Mg and EtOH/Mg in the composition

| Example | Ti/Mg mol/mol | DUP/Mg mol/mol | EtOH/Mg mol/mol |
|---|---|---|---|
| 23 | 0.855 | 0.404 | 0.130 |
| 24 | 0.182 | 0.145 | |
| 25 | 0.126 | 0.128 | 0.071 |
| 26 | 0.100 | 0.082 | 0.041 |
| 27 | | | |
| 28 | 0.081 | 0.088 | |

Titanium and DUP Concentrations of Extracted Compositions

FIG. 55 shows the amount of titanium remaining in the composition as a function of the type of washing. FIG. 56 shows corresponding concentrations of the donor DUP. The results indicate that the concentrations of both titanium and donor continuously decrease in the course of the series of experiments. The concentration of titanium decreases precipitously at the beginning of the series of experiments, indicating that about half the titanium in the composition can be easily removed, and in weak washing conditions at that. Thereafter the reduction in titanium concentration is slower and linear with increasing washing power. The concentration of the donor decreases linearly throughout the series of experiments, indicating that the donor tends to be bound to the composition with a single type of linkage.

Comparison of Extraction of Titanium and Donor

As evidenced by previous experiments, washing of the $(MgCl_2)_v(TiCl_4)_x(DUP)_y(TiCl_3OEt)_z$ composition extracts titanium tetrachloride, $TiCl_4$, and the inner donor, i.e. diundecyl phthalate, DUP, from the composition in such a manner that their final molar ratio approaches 1:1. In FIG. 57, the molar concentration of titanium is compared with that of the donor DUP. The results indicate that the composition contains excess titanium at the beginning of the series of washes, but as the washing power and the number of washes increases, the molar ratio Ti/DUP approaches 1:1.

Changes in the Concentration of Magnesium Chloride in the Composition

In order to monitor the magnesium chloride concentration of the composition after different washing methods, the molar proportion of magnesium in the composition was plotted as a function of washing method. The values for magnesium were obtained from Table 20, and the graph is presented in FIG. 58. An increase in washing power produces an almost linear increase in the proportion of magnesium. Only at the end, when the molar ratio Mg/Ti is approximately 12, does the curve level out slightly. Thus, washing in toluene can be used to prepare an entire series of catalytically adequate compositions with different magnesium concentrations and, thus, different—tailored—catalytic properties. The present invention relates to such tailoring.

Removal of Ethanol, EtOH, by Extraction

The ethanol concentration of all extraction products was determined since any ethanol measured was considered to be quantitatively derived from the titanium trichloride ethoxide, $TiCl_3OEt$, contained in the product. In order to determine to what extent ethanol was present in the final composition in relation to the total amounts of titanium and donor, the curves in FIG. 59 were plotted using the data in Table 22. In the figure, the molar ratios Ti/Mg, DUP/Mg and $TiCl_3OEt/EtOH/Mg$ are presented as functions of increasing washing power. According to the results, the component $TiCl_3OEt$ is removed from the compositions by extraction. According to the results, approximately 50% of the titanium is in the form of the said $TiCl_3OEt$ component. Only in the first series of experiments, where only pentane is used for washing, is the total amount of titanium considerably larger and only some 15% of the titanium is in the form of the $TiCl_3OEt$ component.

Bulk Homopolymerisation of Propene

All the washed compositions were used as catalysts in test polymerisations; the latter have been described in the above experimental section. All the bulk homopolymerisations came out well. The polymers were analysed for MFR and TS. The results are presented in Table 23.

TABLE 23

Polymerisation performances of the catalytic compositions

| Example | Activity kg PP/g cat | Activity kg PP/g Ti | MFR$_2$ g/10 min | TS % | II* % |
|---|---|---|---|---|---|
| 23 | 10.8 | 136 | 12.5 | 7.5 | 92.5 |
| 24 | | | | | |
| 25 | 11.4 | 356 | 8.1 | 2.7 | |
| 26 | 6.6 | 228 | 14.2 | 5.2 | |
| 27 | | | | | |
| 28 | 22.2 | 1057 | 7.1 | 2.1 | 97.7 |

*isotacticity index

Activity

FIG. 60 shows the activities of the washed catalytic compositions as functions of washing power. In three of the examples, activity increases with increasing washing power. With regard to commercial utilisation, it is important to note that, according to the results, a thorough toluene wash produces catalytically active compositions with activities up to 22 kg PP/g cat. If washing is accomplished only with an aliphatic hydrocarbon, such as pentane or heptane, activity remains at approximately 11 kg PP/g cat.

MFRs of Polymers

FIG. 61 shows the MFRs of the polymers as functions of washing power. Again, a distinct systematic trend is seen on the basis of the said three examples, i.e. the higher the washing power, the lower the MFR. At a low washing power, the MFR values were approximately 13, whereas effective toluene washing yielded an MFR value of approximately 7.

TS

FIG. 62 shows TS values as functions of washing power. Gentle washing produced a TS value of approximately 8% while effective toluene washing reduced the TS values to two percent.

Summary

Examples 23 to 28 investigated the effect of washing power on the original soluble $(MgCl_2)_v(TiCl_4)_x(DUP)_y(TiCl_3OEt)_z$ composition. The results can be summed up as follows:

1. Washing of the soluble composition with an aliphatic hydrocarbon results in a new composition with approximately the following molar proportions of components: $(MgCl_2)_6(TiCl_4)_{0.5}(DUP)(TiCl_3OEt)_{0.5}$.
2. Washing of the soluble composition with toluene resulted in approximately the following molar composition: $(MgCl_2)_{12}(TiCl_4)_{0.5}(DUP)(TiCl_3OEt)_{0.5}$
3. Washing with toluene yields a number of compositions with molar compositions ranging from that of the original soluble composition to the above composition with 12 molecules of magnesium chloride.
4. The study also brought the observation of a strong correlation between activity and melt flow rate, i.e. the higher the activity, the lower the melt flow rate.
5. Activity increases with increasing power of toluene washing, the highest activities obtained being approximately 22 kg PP/g cat.
6. When the complex $MgCl_2.3EtOH$ is used as starting material, the washed final product always retains some ethanol derived from the titanium trichloride ethoxide, $TiCl_3OEt$, of the product. The molar proportions of the final, multiply toluene-washed composition are:

$(MgCl_2)_{12}(TiCl_4)_{0.5}(DUP)(TiCl_3OEt)_{0.5}$

This composition appears stable and will not change essentially with continued washing; therefore. it is probably a stoichiometric complex.

What is claimed is:

1. A composition containing magnesium, titanium, halogen, and a carboxylic acid ester, prepared by bringing into contact with each other at a certain temperature and reacting the complex $MgX^1{}_2.nR^1OH$, where $X^1$ is a halogen, $R^1$ is a $C_1$–$C_{20}$ alkyl, and n is in the range 2.0–6.4, a titanium tetrahalide $TiX^2{}_4$, where $X^2$ is a halogen, and a carboxylic acid ester, wherein the said composition is obtained in the liquid state by using:
   (a) as the said carboxylic acid ester, a compound that contains at least 8·j carbon atoms and is compatible with the following formula (I)

$R^2(COOR^3)j$         (I)

where $R^2$ is a j-valent substituted or unsubstituted $C_1$–$C_{34}$ hydrocarbon group, $R^3$ is a $C_6$–$C_{20}$ alkyl group, and j is an integer from 1 to 4;
   (b) a molar ratio $R^2(COOR^3)j/MgX^1{}_2.nR^1OH$ that is $\geq$ approximately 0.8/j;
   (c) a molar ratio $TiX^2{}_4/MgX^1{}_2.nR^1OH$ that is $\geq$ approximately n;
   (d) optionally an organic dissolvent substance S; and
   (e) as the said certain temperature, a value that is in the range 40–200° C.

2. A composition according to Patent claim 1, wherein such a molar ratio $TiX^2{}_4/MgX^1{}_2.nR^1OH$ is used as yields the said reaction product as dissolved in an excess amount of titanium tetrahalide (in respect of the alcohol, $R^1OH$), with the ingredients being brought into contact with each other at a molar ratio $TiX^2{}_4/MgX^1{}_2.nR^1OH$ that is preferably $\geq$ approximately 1.7n, more preferably in the range 10–100 and most preferably in the range 20–50 when n is in the range 2.0–6.4.

3. A composition according to Patent claim 1, wherein such a molar ratio $R^2(COOR^3)_j/MgX^1{}_2.nR^1OH$ is used as yields the said reaction product as dissolved in an excess amount of titanium tetrahalide (in respect of the alcohol, $R^1OH$), with the molar ratio $R^2(COOR^3)_j/MgX^1{}_2.nR^1OH$ being preferably $\geq$ approximately 1/j, most preferably in the range of approximately 1/j–20/j.

4. A composition according to Patent claim 1, wherein such a temperature is used as yields the said reaction product as dissolved in an excess amount of titanium tetrahalide (in respect of the alcohol, $R^1OH$), with the temperature being preferably in the range of approximately 60° C. to approximately 140° C., most preferably in the range 80–120° C.

5. A composition according to Patent claim 1, wherein there are one or two carboxyl ester groups in the carboxylic acid ester, $R^2(COOR^3)_j$, i.e. j is 1 or 2.

6. A composition according to Patent claim 5, wherein the carboxylic acid ester, $R^2(COOR^3)_j$, is a carboxylic acid ester containing at least 12 carbon atoms, preferably an ester of an α,β-unsaturated carboxylic acid, more preferably an ester of an aromatic carboxylic acid, even more preferably a di-$C_6$–$C_{20}$ alkyl ester of phthalic acid, most preferably a di-$C_8$–$C_{14}$ alkyl ester of phthalic acid.

7. A composition according to Patent claim 1, wherein $X^1$ and/or $X^2$ are/is chlorines/chlorine.

8. A composition according to Patent claim 1, wherein the group $R^1$ in the complex $MgX^1{}_2.nR^1OH$ is a $C_1$–$C_{12}$ alkyl, preferably a $C_2$–$C_8$ alkyl.

9. A composition according to Patent claim 1, wherein the said complex, $MgX^1{}_2.nR^1OH$, the said titanium tetrahalide, $TiX^2{}_4$, and the carboxylic acid ester, $R^2(COOR^3)_j$, are brought into contact with an organic substance S capable of dissolving the said reaction product, preferably a chlorinated hydrocarbon and/or aromatic hydrocarbon enhancing the dissolution of the reaction product, most preferably an aromatic hydrocarbon, such as toluene.

10. A composition according Patent claim 9, wherein the molar ratio $TiX^2{}_4/S$ is in the range 0.5–20, preferably in the range 1–6.

11. A composition according to Patent claim 10, wherein a sequence of addition is used where
   the complex $MgX^1{}_2.nR^1OH$, a possible organic dissolvent substance and the titanium tetrahalide, $TiX^2{}_4$, are first added, preferably in this order, and
   then the carboxylic acid ester, $R^2(COOR^3)_j$, is added.

12. A composition according to Patent claim 1, wherein the said liquid composition is recovered in the solid state, preferably by precipitating the said dissolved reaction product.

13. A composition according to Patent claim 12, wherein the composition is recovered in the solid state by cooling the said liquid composition and/or by bringing the dissolved composition into contact with a substance that will precipitate it, preferably an aliphatic $C_5$–$C_{12}$ hydrocarbon, most preferably so that the molar ratio between the aliphatic hydrocarbon and the titanium tetrachloride of the dissolved composition is in the range 0.05–5, preferably in the range 0.1–2.

14. A composition according to Patent claim 12, wherein the composition is recovered in the solid state by bringing the dissolved composition into contact with and making it to react with a second carboxylic acid ester that precipitates it.

15. A composition according to Patent claim 14, wherein the said second carboxylic acid ester is a compound compatible with the following formula (II)

$R^4(COOR^5)_j$         (II)

where $R^4$ is a j-valent substituted or unsubstituted $C_1$–$C_{34}$ hydrocarbon group, $R^5$ is a $C_1$–$C_5$ alkyl group and j is an integer from 1 to 4, and is preferably a $C_1$–$C_5$ alkyl ester of an α,β-unsaturated carboxylic acid, more preferably a $C_1$–$C_5$ alkyl ester of an aromatic carboxylic acid, most preferably a di- $C_1$–$C_5$ alkyl ester of phthalic acid, most preferably of all a di- $C_1$–$C_4$ alkyl ester of phthalic acid.

16. A composition according to Patent claim 14, wherein a molar ratio $R^4(COOR^5)_j/MgX^1_2.nR^1OH$ in the range 0.2/j–4/j, preferably in the range 0.4/j–2/j, is used.

17. A composition according to Patent claim 14, wherein the precipitant second carboxylic acid ester is used as a solution, preferably as a solution in an aromatic hydrocarbon, most preferably as a 15–35% w/w solution in an aromatic hydrocarbon such as toluene.

18. A composition according to Patent claim 12, wherein the composition is recovered in the solid state by filtration and/or decantation.

19. A composition according to Patent claim 12, wherein the solid composition is washed with liquid, preferably with hydrocarbon, preferably at least once.

20. A composition according to Patent claim 12, wherein the solid composition is extracted with a solvent that enriches magnesium into the said product, preferably with an aromatic hydrocarbon such as toluene.

21. A composition according to Patent claim 20, wherein the extraction with a magnesium-enriching solvent is carried out several times, preferably 2 to 10 times, most preferably 3 to 5 times.

22. A composition according to Patent claim 20, wherein the washing/extraction is carried out with both a non-magnesium-enriching and a magnesium-enriching liquid, preferably first with a non-magnesium-enriching liquid at least once, then with a magnesium-enriching solvent several times and finally with a non-magnesium-enriching liquid at least once.

23. A composition according to Patent claims 1, wherein it is prepared a') by bringing the complex $MgCl_2.nR^6OH$, where $R^6$ is a $C_1$–$C_8$ alkyl and n is in the range 2.0–6.4, into contact with titanium tetrachloride, $TiCl_4$, at a molar ratio $TiCl_4/MgCl_2.nR^6OH$ that is in the range 20–60, with a di- $C_8$–$C_{14}$ alkyl ester of phthalic acid ($D^1$) at a molar ratio $D^1/Mg$ that is in the range of approximately 0.5–10, and preferably with toluene at a molar ratio $TiCl_4$/toluene that is in the range 1–6, and by heating the mixture to 80–120° C., to yield in dissolved form a composition of the said complex, titanium tetrachloride and a di- $C_8$–$C_{14}$ alkyl ester of phthalic acid.

24. A composition according to Patent claim 23, wherein phase a') is followed by b') recovery of the said dissolved reaction product as the first solid composition by bringing it into contact with an essentially inert substance, preferably an aliphatic $C_5$–$C_{12}$ hydrocarbon, that precipitates it c') and separation of the first solid composition from the liquid and possibly washing of it.

25. A composition according to Patent claim 23, wherein phase a') is followed by b'') bringing of the said dissolved composition into contact with and making it to react with a di- $C_1$–$C_6$ alkyl ester of phthalic acid ($D^2$) at a molar ratio $D^2/MgCl_2.nR^6OH$ that is in the range 0.2–1 to yield in the liquid a second solid composition containing the said di- $C_1$–$C_6$ alkyl ester of phthalic acid ($D^2$) and c'') separation of the said second solid composition from the liquid and preferably washing of it.

26. A composition according to Patent claim 24, wherein phase c') is followed by d') extraction of the said first solid composition with a magnesium-enriching solvent, such as toluene, to yield a third solid composition with a magnesium concentration higher than that in the first solid composition, and possibly washing of the third solid composition.

27. A composition containing magnesium, titanium, halogen and an electron donor, wherein it is soluble at least in liquid titanium tetrahalide, in a mixture of liquid titanium tetrahalide and a dissolvent organic substance $S^1$, or in a dissolvent organic substance $S^1$ and that it is a composition compatible with the following empirical formula (III):

$$(MgX^3{}_2)_v(TiX^4{}_4)_x(D^3)_y(TiX^4{}_3OR^7)_z \qquad (III)$$

where $X^3$ is a halogen, $X^4$ is a halogen, $R^7$ is a $C_1$–$C_{20}$ alkyl, the inner electron donor $D^3$ is a di- $C_6$–$C_{20}$ alkyl ester of phthalic acid, x+z is basically approximately 1, v is 1 to 8, x is 0 to 1, and y is 0.2 to 2.

28. A composition according to Patent claim 27, wherein the liquid titanium tetrahalide is titanium tetrachloride.

29. A composition according to Patent claim 27, wherein the dissolvent organic substance $S^1$ is an aromatic hydrocarbon, preferably toluene.

30. A composition according to Patent claim 27, wherein it is soluble at least in warm liquid titanium tetrahalide, in a mixture of liquid titanium tetrahalide and the dissolvent substance $S^1$, or in the dissolvent substance $S^1$, preferably at 60° C. to approximately 140° C., most preferably at 80–120° C.

31. A composition according to Patent claim 27, wherein $X^3$ is chlorine and that, independently of the former, $X^4$ is chlorine.

32. A composition according to Patent claim 27, wherein the inner electron donor $D^3$ is a di- $C_7$–$C_{16}$ alkyl ester of phthalic acid.

33. A composition according to Patent claim 27, wherein $R^7$ is a $C_2$–$C_8$ alkyl.

34. A composition according to Patent claim 27, wherein v is 2 to 8, preferably 3 to 8; x is 0.2 to approximately 1.0, preferably 0.4 to approximately 1.0, and y is 0.6 to 1.4, preferably 0.8 to 1.2.

35. A composition according to Patent claim 27, wherein it is prepared by a method according to any of Patent claims 12, 13 or 24.

36. A composition containing magnesium, titanium, halogen and an electron donor, wherein it is a composition compatible with the following empirical formula (IV):

$$(MgX^5{}_2)_{v'}(TiX^6{}_4)_{x'}(D^4)_{y'}(TiX^6{}_3OR^8)_{z'} \qquad (IV)$$

where $X^5$ is a halogen, $X^6$ is a halogen, $R^8$ is a $C_1$–$C_{20}$ alkyl, the inner electron donor $D^4$ is a di- $C_6$–$C_{20}$ alkyl ester of phthalic acid, x'+z' is basically approximately 1, v' is 9 to 16, x' is 0.2 to 1, and y' is 0.2 to approximately 1.

37. A composition according to Patent claim 36, wherein that $X^5$ is chlorine, $X^6$ is chlorine, v' is 7 to 14, x' is 0.4 to 0.8, and y' is approximately 0.8 to 1.2, whereby it is preferably a composition compatible with the approximate formula (V):

$$(MgCl_2)_{12}(TiCl_4)_{0.5}D^4(TiCl_3OEt)_{0.5} \qquad (V)$$

where $D^4$ is the same as above.

38. A composition according to Patent claim 36, wherein it is prepared by a method according to Patent claim 20.

39. A composition containing magnesium, titanium, halogen and an electron donor, wherein it is a composition compatible with the following empirical formula (VI):

$$(MgX^7{}_2)_{v''}(TiX^8{}_4)_{x''}(D^5)_{y''}(TiX^8{}_3OR^9)_{z''} \quad (VI)$$

where $X^7$ is a halogen, $X^8$ is a halogen, $R^9$ is a $C_1$–$C_{20}$ alkyl, the inner electron donor $D^5$ is a di- $C_1$–$C_6$ alkyl ester of phthalic acid, x"+z" is basically approximately 1.2, v" is 1.5 to 10.5, x" is 0.2 to 1.2, and y" is 0.2 to 1.2.

40. A composition according to Patent claim 39, wherein $X^7$ is chlorine, $X^8$ is chlorine, the inner electron donor $D^5$ is a di- $C_1$–$C_4$ alkyl ester of phthalic acid, v" is 1.6 to 2.4, x" is 0.8 to 1.2, and y" is 0.8 to 1.2, whereby it is preferably a complex composition compatible with the approximate formula (VII):

$$(MgCl_2)_2TiCl_4D^5 \quad (VII).$$

41. A composition according to Patent claim 39, wherein it is prepared by a method according to Patent claim 14.

42. A method described by Patent claim 1 for the preparation of a composition containing magnesium, titanium, halogen and an electron donor.

43. A method for polymerisation of α-olefins by bringing into contact with each other and reacting a procatalyst, which is a composition containing magnesium, titanium, halogen and an inner electron donor ED, a cocatalyst, which is an organometallic compound of a metal belonging to one of groups 1, 2 or 13 of the periodic system, preferably an external donor with at least one ligand atom capable of donating electrons, and one or more α-olefins, wherein a composition according to Patent claim 1 is used as procatalyst.

44. A method according to Patent claim 43, wherein the α-olefin used is propene, either alone or together with another α-olefin, such as ethene.

45. A method according to Patent claim 43, wherein the cocatalyst used is an organoaluminium compound, preferably a compound according to formula (VIII)

$$(R^{10}{}_mAlX^9{}_{3-m})_p \quad (VIII)$$

where $R^{10}$ is a $C_1$–$C_{10}$ alkyl, $X^9$ is an atom or organic group containing a free electron pair, preferably a halogen such as chlorine, m is 2 or 3, and p is 1 or 2.

46. A method according to Patent claim 45, wherein the molar ratio Al/Ti between the aluminium of the cocatalyst and the titanium of the said composition is in the range 50–500, preferably in the range 200–350.

47. A method according to Patent claim 43, wherein the external donor ED is a silane, preferably a compound compatible with the formula (IX)

$$R^{11}{}_qSi(OR^{12})_{4-q} \quad (IX)$$

where group $R^{11}$ is one type or several types of $C_1$–$C_{20}$ alkyl or $C_6$–$C_{32}$ aryl, group $R^{12}$ is one type or several types of $C_1$–$C_{10}$ alkyl, and q is 1, 2 or 3.

48. A method according to Patent claim 45, wherein the molar ratio Al/ED between aluminium and the external donor ED is in the range 5–20, preferably in the range 6–15.

49. A method according to Patent claim 45, wherein the molar ratio ED/Ti between the external donor and the titanium of the said composition is in the range 5–50, more preferably in the range 10–40, most preferably in the range 20–30.

* * * * *